(12) United States Patent
Parr et al.

(10) Patent No.: US 8,008,008 B2
(45) Date of Patent: *Aug. 30, 2011

(54) MITOCHONDRIAL MUTATIONS AND REARRANGEMENTS AS A DIAGNOSTIC TOOL FOR THE DETECTION OF SUN EXPOSURE, PROSTATE CANCER AND OTHER CANCERS

(75) Inventors: Ryan Parr, Thunder Bay (CA); Robert Thayer, Thunder Bay (CA); Gabriel Dakubo, Thunder Bay (CA); Jennifer Maki, Thunder Bay (CA); Kerry Robinson, Thunder Bay (CA); Andrea Maggrah, Thunder Bay (CA); Brian Reguly, Thunder Bay (CA); Andrew Harbottle, Newcastle Upon Tyne (GB); Mark Birch-Machin, Newcastle Upon Tyne (GB)

(73) Assignee: Mitomics Inc., Thunder Bay, Ontario (CA)

( * ) Notice: Subject to any disclaimer, the term of this patent is extended or adjusted under 35 U.S.C. 154(b) by 739 days.

This patent is subject to a terminal disclaimer.

(21) Appl. No.: 11/975,390

(22) Filed: Oct. 18, 2007

(65) Prior Publication Data

US 2009/0192047 A1 Jul. 30, 2009

Related U.S. Application Data

(60) Provisional application No. 60/789,872, filed on Apr. 7, 2006, provisional application No. 60/721,522, filed on Sep. 29, 2005, provisional application No. 60/672,016, filed on Apr. 18, 2005.

(30) Foreign Application Priority Data

Apr. 18, 2006 (CA) ................ PCT/CA2006/000652

(51) Int. Cl.
*C12Q 1/68* (2006.01)
(52) U.S. Cl. ........................................ 435/6
(58) Field of Classification Search ............ None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 5,565,323 A | 10/1996 | Parker et al. |
| 6,344,322 B1 | 2/2002 | Polyak et al. |
| 2002/0155438 A1 | 10/2002 | Simpson et al. |
| 2003/0092019 A1 | 5/2003 | Meyer et al. |
| 2004/0191769 A1 | 9/2004 | Marino et al. |
| 2005/0026167 A1 | 2/2005 | Birch-Machin et al. |
| 2005/0244851 A1 | 11/2005 | Blume et al. |

FOREIGN PATENT DOCUMENTS

| | | |
|---|---|---|
| CA | 2356536 | 2/2003 |
| EP | 0812922 | 12/1997 |
| EP | 1 266 970 | 12/2002 |
| JP | 11-113597 | 4/1999 |
| WO | WO 98/23632 | 6/1998 |
| WO | WO 00/63441 | 10/2000 |
| WO | WO 01/68923 | 9/2001 |
| WO | WO 02/22873 | 3/2002 |
| WO | WO 02/101086 | 12/2002 |
| WO | WO 03/078661 | 9/2003 |

OTHER PUBLICATIONS

Cormier-Daire et al., Mitochondrial DNA rearrangements with onset as chronic diarrhea with villous atrophy, The Journal of Pediatrics, Jan. 1994, vol. 124, No. 1, pp. 63-70.

Petros, John A. et al., mtDNA mutations increase tumorigenicity in prostate cancer, PNAS, Jan. 18, 2005, vol. 102, No. 3, pp. 719-724.

Zhu, Weizhu, M.D. et al., Large-scale mitochondrial DNA deletion mutations and nuclear genome instability in human breast cancer, Cancer Detection and Prevention, 28, pp. 119-126 © 2004 International Society for Preventive Oncology.

Linnane, Anthony W. et al., Mitochondrial Gene Mutation: The Ageing Process and Degenerative Diseases, 22 Biochemistry International. pp. 1067-1076 (1990).

Modica-Napolitano, Josephine S. et al., Mitochondria as Targets for Detection and Treatment of Cancer, 4 Expert Reviews in Molecular Medicine. pp. 1-19 (2002).

Taanman, J.W. et al., Molecular Mechanisms in Mitochondrial DNA Depletion Syndrome, 6 Human Molecular Genetics. pp. 935-942 (1997).

Ward, R.H. et al., Genetic and Linguistic Differentiation in the Americas, 90 Proceedings of the National Academy of Sciences. pp. 10663-10667 (1993).

Armstrong, B.K. (2004). How sun exposure causes skin cancer: an epidemiological perspective. Prevention of Skin Cancer, Hill, D., Elwood, J.M. & English, D.J. (eds), vol. 3. pp. 89-116. Cancer Prevention—Cancer Causes. Kluwer Acedemic Publishers.

Armstrong, B.K. & Kricker, A. (2001). The epidemiology of UV induced skin cancer. J Photochem Photobiol B, 63, 8-18.

Berneburg, M., Gattermann, N., Stege, H., Grewe, M., Vogelsang, K., Ruzicka, T. & Krutmann, J. (1997). Chronically ultraviolet-exposed human skin shows a higher mutation frequency of mitochondrial DNA as compared to unexposed skin and the hematopoietic system. Photochem Photobiol, 66, 271-5.

Berneburg, M., Plettenberg, H., Medve-Konig, K., Pfahlberg, A., Gers-Barlag, H., Gefeller, O. & Krutmann, J. (2004). Induction of the photoaging-associated mitochondrial common deletion in vivo in normal human skin. J Invest Dermatol, 122, 1277-83.

(Continued)

Primary Examiner — James Martinell
(74) Attorney, Agent, or Firm — Simpson & Simpson, PLLC

(57) ABSTRACT

Mitochondrial DNA deletions useful for the detection of cancers and sun exposure are provided. In particular, methods and kits for detecting mitochondrial DNA deletions for the early detection, diagnosis and progression of prostate cancer, sun exposure and non-melanoma skin cancer are provided.

17 Claims, 15 Drawing Sheets

OTHER PUBLICATIONS

Boukamp, P., Petrussevska, R.T., Breitkreutz, D., Hornung, J., Markham, A. & Fusenig, N.E. (1988). Normal keratinization in a spontaneously immortalized aneuploid human keratinocyte cell line. J Cell Biol, 106, 761-71.

Croteau, D.L. & Bohr, V.A. (1997). Repair of oxidative damage to nuclear and mitochondrial DNA in mammalian cells. JBiol Chem, 272, 25409-12.

Degoul, F., Nelson, I., Amselem, S., Romero, N., Obermaier-Kusser, B., Ponsot, G., Marsac, C. & Lestienne, P. (1991). Different mechanisms inferred from sequences of human mitochondrial DNA deletions in ocular myopathies. Nucleic Acids Res, 19, 493-6.

Durham, S.E., Krishnan, K.J., Betts, J. & Birch-Machin, M.A. (2003). Mitochondrial DNA damage in non-melanoma skin cancer. Br J Cancer, 88, 90-5.

Koch, H., Wittern, K.P. & Bergemann, J. (2001). In human keratinocytes the Common Deletion reflects donor variabilities rather than chronologic aging and can be induced by ultraviolet A irradiation. J Invest Dermatol, 117, 892-7.

Ledoux, S.P., Patton, N.J., Avery, L.J. & Wilson, G.L. (1993). Repair of N-methylpurines in the mitochondrial DNA of *Xeroderma pigmentosum* complementation group D cells. Carcinogenesis, 14, 913-7.

Mita, S., Rizzuto, R., Moraes, C.T., Shanske, S., Arnaudo, E., Fabrizi, G.M., Koga, Y., Dimauro, S. & Schon, E.A. (1990). Recombination via flanking direct repeats is a major cause of large-scale deletions of human mitochondrial DNA. Nucleic Acids Res, 18, 561-7.

Moraes, C.T., Ricci, E., Petruzzella, V., Shanske, S., Dimauro, S., Schon, E.A. & Bonilla, E. (1992). Molecular analysis of the muscle pathology associated with mitochondrial DNA deletions. Nat Genet, 1, 359-67.

Moraes, C.T., Sciacco, M., Ricci, E., Tengan, C.H., Hao, H., Bonilla, E., Schon, E.A. & Dimauro, S. (1995). Phenotype-genotype correlations in skeletal muscle of patients with mtDNA deletions. Muscle & Nerve, 3, S 150-3.

Schon, E.A., Rizzuto, R., Moraes, C.T., Nakase, H., Zeviani, M. & Dimauro, S. (1989). A direct repeat is a hotspot for large-scale deletion of human mitochondrial DNA. Science, 244, 346-9.

Sciacco, M., Bonilla, E., Schon, E.A., Dimauro, S. & Moraes, C.T. (1994). Distribution of wild-type and common deletion forms of mtDNA in normal and respiration-deficient muscle fibers from patients with mitochondrial myopathy. Hum Mol Genet, 3, 13-9.

Shoffner, J.M., Lott, M.T., Voljavec, A.S., Soueidan, S.A., Costigan, D.A. & Wallace, D.C. (1989). Spontaneous Kearns-Sayre/chronic external ophthalmoplegia plus syndrome associated with a mitochondrial DNA deletion: a slip-replication model and metabolic therapy. Proc Natl Acad Sci USA, 86, 7952-6.

Alonso, A. C Alves, M.P. Suarez-Mier, C Albarran, L Pereira, L Fernandez De Simon, P. Martin, O Garcia, L Gusmao, M Sancho, A Amorim 2005. J Clin Pathology 58: 83-86.

Anderson S, et al., Sequence and Organization of the human mitochondrial genome. Nature 290:457-464, 1981.

Andrews RM, et al., Reanalysis and revision of the Cambridge reference sequence for human mitochondrial DNA. Nature Genetics 23(2):147, 1999.

Berneburg M, et al., Singlet oxygen mediates the UVA-induced generation of the photoaging-associated mitochondrial common deletion. J. Biol. Chem. 274(22):15345-15349, 1999.

Berthon P, Valeri A, Cohen-Akenine A, Drelon E, Paiss T, Wohr G, Latil A et al., Predisposing gene for early-onset prostate cancer, localized on chromosome 1q42.2-43. Am. J. Hum. Genet., 62: 1416-1424, 1998.

Birch-Machin MA, et al., Study of skeletal muscle mitochondrial dysfunction. Methods in Toxicology, vol. 2, 51-69,1993.

Birch-Machin MA, et al., Mitochondrial DNA deletions in human skin reflect photo rather than chronologic aging. J. Invest.Dermatol., 110:149-152 1998.

Birch-Machin MA, Taylor RW, Cochran B, Ackrell BAC, Turnbull DM. Late-onset optic atrophy, ataxia, and myopathy associated with a mutation of a complex II gene. Ann Neurol 48: No. 3; 330-335, 2000(b).

Birch-Machin MA, Mitochondria and skin disease. Clin. Exp. Dermatol,. 25(2), 141-146, 2000 (c).

Birch-Machin MA and Krishnan K. Abstracts—Mitrochondria 2001 Meeting, San Diego, CA, Feb. 28-Mar. 2, 2001, Mitochondrion, p. 46 (2001).

Birch-Machin MA, Lindsey J. Lusher M and Krishnan K. Mitochondrion1 (Suppl) 1, S30 (2001). 101.

Bogliolo, M, et al., Detection of the '4977 bp' mitochondrial DNA deletion in human atherosclerotic lesions. Mutagenesis, 14: 77-82, 1999.

Brierley EJ, Johnson MA, Lightowlers RN, James O, Turnbull DM., Role of mitochondrial DNA mutations in human aging: Implications for the central nervous system and muscle. Ann Neurol 43(2):217-223, 1998.

Brockington, et al., A tandem duplication in the D-loop of human mitochondrial DNA is associated with deletions in mitochondrial myopathies. Nature Genet 4:67-71, 1993.

Brown, M.D., et al., Clustering of Caucasian Leber hereditary optic neuropathy patients containing the 11778 or 14484 mutations on an mtDNA lineage. Am J. Humn Genet, 60: 381-387, 1997.

Buttyan R, Sawczuk IS, Benson MC, Siegal JD, Olsson CA., Enhanced expression of the c-myc protooncogene in high grade human prostate cancers. Prostate 11:327-337, 1987.

Cairns P, Okami K, Halachmi S, Halachmi N, Esteller M, Herman JG, Jen J et al., Frequent inactivation of PTEN/MMAC1 in primary prostate cancer. Cancer Res 57:4997-5000, 1997.

Chinnery PF, Howel N, Andrews, R.M., Turnbull DM. Clinical mitochondrial genetics. J.Med.Genet.; 36: 425-436, 1999.

Chinnery PF and Turnbull DM., Mitochondrial DNA and disease. Lancet 354 (supplement 1): 17-21, 1999.

Chomyn A, et al., Melas mutation in mtDNA binding-site for transcription termination factor causes defects in protein-synthesis and in respiration but no change in levels upstream and downstream mature transcripts. Proc. Natl. Acad. Sci. USA 89(10):4221-4225, 1992.

Corral-Debrinski et al., Association of Mitochondrial-DNA Damage With Aging and Coronary Atherosclerotic Heart-Disease. Mutat Res, 275: 169-180, 1992.

Cortopassi G. A. and Arnheim, N. Detection of a specific mitochondiral DNA deletion in tissues of older humans, Nucleic Acids Research. 18, 6927-6933 1990.

Cortopassi G, Wang E., Modelling the Effects of Age-Related mtDNA Mutation Accumulation—Complex-I Deficiency, Superoxide and Cell-Death. Biochim Biophys Acta 1271(1):171-176,1995.

Croteau DL, Stierum RH, Bohr VA, Mitochondrial DNA repair pathways. Mutat Res 434(3):137-148, 1999.

Easton RD, Merriwether AD, Crews DE, and Ferrell RE., mtDNA variation in the Yanomami: Evidence for additional New World founding lineages. Am. J. Hum. Genet. 59:213-225, 1996.

Fahn H, Wang L, Hseih R, Chang S, Kao S, Huang M, and Wei Y. Age-related 4977 bp Deletion in Human Lung Mitochondrial DNA. American Journal of Respiratory Critical Care Medicine, 154:1141-1145, 1996.

Finegold D., Diagnosis:The Promise of DNA Analysis in Understanding Mitochondrial Disease; Mitochondrial and Metabolic Disorders, p. 12.

Flanagan N, et al., Pleiotropic effects of the melanocortin 1 receptor (MC1R) gene on human pigmentation. Hum Mol Genet 9 (17):2531-2537, 2000.

Flanagan N, Ray AJ, Todd C, Birch-Machin MA and Rees JL. The relation between melanocortin 1 receptor genotype and experimentally assessed ultraviolet radiation sensitivity. J Invest. Dermatol (2001) 117 (5) 1314-1317.

Gattermann, N, Berneburg, M, Heinisch, J, Aul, C, Schneider, W., Detection of the ageing-associated 5-kb common deletion of mitochondrial-DNA in blood and bone-marrow of hematologycally normal adults—absence of the deletion in clonal bone-marrow disorders. Leukemia 9(10): 1704-10, 1995.

Habano W, Nakamura S, Sugai T., Microsatellite instability in the mitochondrial DNA of colorectal carcinomas: Evidence for mismatch repair systems in mitochondrial genome. Oncogene 17 (15):1931-1937, 1998.

Harding RM, et al., Evidence for variable selective pressures at MC1R. Am. J. Hum. Genet. 66, 1351-1361, 2000.

Hattori, DR., et al, Age-dependent increase in deleted mitochondrial DNA in the human heart: possible contributory factor to presbycardia, Am. Heart J., 121, 1735-1742, 1991.

Hayashi J, Ohta S, Kikuchi A, Takemitsu M, Goto Y, Nonaka I., Introduction of Disease-Related Mitochondrial-DNA Deletions Into Hela-Cells Lacking Mitochondrial-DNA Results in Mitochondrial Dysfunction. Proc Natl Aced Sci USA 88 (23):10614-10618, 1991.

Hayward SW, Grossfeld GD, Tlsty TD, Cunha GR., Genetic and epigenetic influences in prostatic carcinogenesis—(Review). Int J Oncol 13:35-47, 1998.

Healy E, Birch-Machin MA, Rees JL. The Human Melanocortin-1 Receptor Gene. In the Melanocortin Receptors (Cone Rd (ed)). Humana Press Inc. New Jersey, USA, 1999 p. 341.

Healy E, et al., Melanocortin-1-receptor gene and sun sensitivity in individuals without red hair. Lancet 355.9209, 1072-1073, 2000.

Hsieh, RH, et al., Age-Dependent Respiratory Function Decline and DNA Deletions in Human Muscle Mitrochondria, Biochemistry and Molecular Biology Int'l, vol. 32, No. 6, Apr. 1994, pp. 1009-1022.

Ikebe et al., Increase of deleted mitochondrial DNA in the striatum in Parkinson's disease and senescence, Biochem. Biophys. Res. Commun. 170, 1044-1048, 1990.

Katayama et al., Deleted mitochondrial DNA in the skeletal muscle of aged individuals, Biochem. Int., 25, 47-56 1991.

Kleinle S, et al., Detection and characterization of mitochondrial DNA rearrangements in Pearson and Kearns-Sayre syndromes by long PCR. Human Genet. 100:643-650, 1997.

Konishi N, Cho M, Yamamoto K, Hiasa Y. Genetic changes in prostate cancer. Pathol. Int. 47:735-747, 1997.

Krishnan K and Birch-Machin MA. British Society for Investigative Dermatology Annual Meeting. British Journal of Dermatology (2002), 146, (p. 723).

Ledoux SP, et al. Repair of alkylation and oxidative damage in mitochondrial DNA. Mutat Res 434(3):149-159, 1999.

Lee HC, et al. Ageing-associated tandem duplications in the D-loop of mitochondrial DNA of human muscle. FEBS Letters 354:79-83, 1994.

Lee HC, Lu CY, Fahn HJ, Wei YHu. Aging-and smoking-associated alteration in the relative content of mitochondrial DNA in human lung. Federation of European Biochemical Societies, 441:292-296, 1998.

Lee HC, et al. Concurrent increase of oxidative DNA damage and lipid peroxidation together with mitochondrial DNA mutation in human lung tissues during aging—Smoking enhances oxidative stress on the aged tissues. Arch. Biochem. Biophys. 362(2): 309-16, 1999.

Liu CS, Kao SH, Wei YH. Smoking-Associated Mitochondrial DNA Mutations in Human Hair Follicles. Environ. Mol. Mutagen 30(1): 47-55, 1997.

Lopez, J.V. et al. (1994) Numt, a recent transfer and tandem amplification of mitochondrial DNA to the nuclear genome of the domestic cat. J. Mol. Evol. 39, 174-190.

Lowes S, Krishnan K, Lindsey J and Brich-Machin MA. British Society for Investigative Dermatology Annual Meeting. British Journal of Dermatology (2002), 146, 736.

Meibner C, Von Wurmb N, Oehmichen M., Detection of the age-dependent 4977 bp deletion of mitochondrial DNA; a pilot study, Int. J. Legal Med. 110: 288-291, 1997.

Michikawa Y, Mazzucchelli F, Bresolin N, Scarlato G, Attardi G., Aging-Dependent Large Accumulation of Point Mutations in the Human mtDNA Control Region for Replication. Science 286: 774-779, 1999.

Miquel J, De Juan E, Sevila I. Oxygen-induced mitochondrial damage and aging. EXS 62:47-57, 1992.

Nachman MW, Brown WM, Stoneking M, Aquardo CF., Nonneutral Mitochondrial DNA Variation in Humans and Chimpanzees. Genetics 142:953-963, 1996.

Naviaux, RK., Mitochondrial Disease- Primary Care Physican's Guide. Psy-Ed. Corp D/B/A Exceptional Parents Guide: 3-10, 1997.

Yu, B, et al.; DNA mutation detection using denaturing high-performance liquid chromatography (DHPLC). Current protocols in human genetics 19, 7.10.1-14, 1998.

Ozen M, et al, Telomeric DNA Marker for Human Prostate Cancer Development?. Prostate 36:264-271, 1998.

Pang et al, Human Skin Mitochondrial DNA Deletions Associated with Light Exposure. Arch. Biochem.Biophys. 312:(2), 534-538, 1994.

Parsons TJ, et al., A high observed substitution rate in the human mitochondrial DNA control region. Nature Genet. 15 (4):363-368, 1997.

Pascucci B, et al., DNA repair of UV photoproducts and mutagenesis in human mitochondrial DNA. J.Mol.Biol. 273 (2):417-427, 1997.

Penta JS, Johnson FM, Wachsman JT, Copeland, W.C., Mitochondrial DNA in human malignancy, Mut. Res. 488, 119-133, 2001.

Polyak K, et al., Somatic mutations of the mitochondrial genome in human colorectal tumours. Nature Genet. 20 (3):291-293, 1998.

Harman, K.E. et al., Defining Target Antigens in Linear IgA Disease Using Skin From Patients With Inherited Genodermatoses as Substrates for Indirect Immunofluorescence Microscopy; Br. J. of Derm. 138, p. 733(1998).

Ray AJ, et al.Abstract of the British Society for Investigative Dermatology, Annual Meeting—Cardiff, Apr. 7-9, 1999, Brit.J.Dermato1. 140:788, 1999.

Ray AJ, Turner R, Nikaido O, Rees JL, Birch-Machin MA., The spectrum of mitochondrial DNA deletions is a ubiquitous marker of ultraviolet radiation exposure in human skin. J. Invest. Dermatol 115(4):674-679, 2000.

Rees JL, Skin cancer [Gorlin's Syndrome], In:The Genetic Basis of Human Cancer, eds Vogelstein B, Kinzler K. New York: McGraw-Hill, pp. 527-536, 1998.

Rehman I, Quinn AJ, Healy E, Rees JL. High-Frequency of Loss of Heterozygosity in Actinic Keratoses, A Usually Benign Disease. Lancet 344: 788-789, 1994.

Rehman I, Takata M, Wu YY, Rees JL. Genetic change in actinic keratoses. Oncogene 12: 2483-2490, 1996.

SAS Enterprise Mining Users Guide, SAS Inc., 2000.

Sawyer E, Van Houten B., Repair of DNA damage in mitochondria. Mutation Res: 434(3):161-176, 1999.

Schurr TG, Ballinger SW, Gan Y, Hodge JA, Merriwether DA, Lawrence DN, Knowler WC, Weiss KM, and Wallace DC., Amerindian Mitochondial DNAs Have Rare Asian Mutations at high Frequencies, Suggesting They Derived from Four Primary Maternal Lineages. Am. J. Hum. Genet. 46:613-623, 1990.

Seidman, M.D. et al., Mitochondrial DNA deletions associated with aging and presbyacusis. Arch. Otolaryngol Head Neck Surg., 123: 1039-1045, 1997.

Shankey TV, Jin JK, Dougherty S, Flanigan RC, Graham S, Pyle JM., DNA-Ploidy and Proliferation Heterogeneity in Human Prostate Cancers. Cytometry 21:30-39, 1995.

Shay JW, Werbin H., Are Mitochondrial DNA Mutations Involved in the Carcinogenic Process?. Mutat. Res:186: p. 149-160, 1987.

Sherrat EJ, Thomas AW, Alcolado. Mitochondrial DNA defects: A widening clinical spectrum of disorders. JC., Clin. Sci. 92:225-235, 1997.

Shoffner JM, Brown MD, Torroni A, Lott MT, Cabell MF, Mirra SS, Beal MF, Yang C, Gearing M, Salvo R, Watts RL, Juncos JL, Hansen LA, Crain BJ, Fayad M, Reckford CL, and Wallace DC., Mitochondrial DNA Variants Observed in Alzheimer Disease and Parkinson Disease Patients, Genomics 17: 171-184, 1993.

Smith DG, Malhi RS, Eshleman J, Lorenz JG and Kaestle FA., Distribution of mtDNA haplogroup X among Native North Americans. Am. J. Hum. Genet. 110:271-284, 1999.

Smith R, Birch-Machin MA, Rees JL. Melanocortin 1 receptor variants in an Irish population. J. Invest. Dermatol. 111: (1) Jul. 1998, 101-104.

Tamura S, et al. Mutations in mitochondrial control region DNA in gastric tumours of Japanese patients. Eur.J.Cancer [A] 35 (2):316-319, 1999.

Tanaka, M. et al, 1996, Automated sequencing of mtDNA, Methods Enzymol. 264: 407-421.

Taniike, M. et al., Mitochondrial Transfer Rnaile Mutation in Fatal Cardiomyopathy. BioChem BioPhys Res Comun, 186: 47-53, 1992.

Taylor RW, Birch-Machin MA, Bartlett K, Turnbull DM., The Control of Mitoch. Oxidations by Complex-III in Rat Muscle and Liver-Mitochondria—Implications for Our Understanding of Mitochondrial Cytopathies in Man. J Biol Chem, 269, 3523-3528 1994.

Tori K. et al., Aging-associated deletions of human diaphragmatic mitochondrial DNA, Am. J. Respir. Cel.l Mol. Biol. in press 1992, p. 543-549.

Valnot, Isabelle, et al., A mitochondrial cytochrome b mutation but no mutations of nuclearly encoded subunits in ubiquinol cytochrome c reductase (complex III) deficiency, Human Genetics (1999) 104: 460-466.

Van Den Bosch BJC, et al., Mutation analysis of the entire mitochondrial genome using denaturing high performance liquid chromatography. Nucleic Acids Res. 28: 89, 2000.

Von Wurmb, N, Oehmichen, M, Meissner, C., Demonstration of the 4977 bp deletion in human mitochondrial DNA from intravital and postmortem blood. Mutat Res. 422:247-254, 1998.

Wallace DC., Diseases of the Mitochondrial-DNA. Annu Rev Biochem, 61: 1176-1212, 1992.

Wallace DC. Mitochondrial-DNA Sequence Variation in Human-Evolution and Disease. Proc. Natl. Acad. Sci. USA 91: 8739-8746, 1994.

Wallace, D.C., Mitochondrial Diseases in man and Mouse. Science, 5(283): 1482-1497, 1999.

Wallace et al., Mitochondiral DNA Mutation Associated with Leber's Hereditary Optic Neuropathy, Science, 1427-1429; 1988.

Walsh PC, Partin, AW, Family history facilitates the early diagnosis of prostate carcinoma.. Cancer 80:Nov. 1, 1997, vol. 80, No. 9; pp. 1871-1874.

Ward RH, Frazier BL, Dew-Jager K, Paabo S., Extensive Mitochondrial Diversity Within a Single Amerindian Tribe. Proc. Natl. Acad. Sci. USA 88:8720-8724, 1991.

Wei YH, Pang C, You B, Lee H., Tandem Duplications and Large-Scale Deletions of Mitochondrial DNA Are Early Molecular Events of Human Aging Process, Annals NY Acad. of Sciences 786:82-101, 1996.

Wei YH. Mitochondrial DNA Mutations and Oxidative Damage in Aging and Diseases: An Emerging Paradigm of Gerontology and Medicine; Proc. of the Nat. Sci. Council of the ROC, vol. 22(2):1998, pp. 55-67; 1997.

Weinstock MA: Epidemiology of ultraviolet radiation. In: JJ Stern RS, MacKie RM and Weinstock MA, Grob (eds) Epidemiology, Blackwell (UK). pp. 121-128, 1998.

Wu & Wallace The Ligation Amplification Reaction (LAR)—Amplification of Specific DNA-Sequences Using Sequential Rounds of Template-Dependent Ligation. Genomics, 4:560, 1989.

Xu J, et al., Evidence for a prostate cancer susceptibility locus on the X chromosome. Nature Genet 20: 175-179,1998.

Yamaguchi KT, et al., Measurement of Free-Radicals From Smoke-Inhalation and Oxygen Exposure by Spin Trapping and ESR Spectroscopy. Free Radical Res. Commun. 16(3):167-74, 1992.

Yeh, J.J., et al., Somatic mitochondrial DNA (mtDNA) mutations in papillary thyroid carcinomas and differential mtDNA sequence variants in cases with thyroid tumours. Oncogene Journal, 19: 2060-2066, 2000.

Yen et al., Ageing-associated 5kb deletion in human liver mitochondrial DNA, Biochem., Biophys., Res. Commun., 178, 124-131 1991.

Yen et al., Age-dependent 6 kb deletion in human liver mitochondrial DNA, Biochem. Int. 26, 457-468 1992.

Zeviani M, et al. Nucleus-driven Multiple Large-Scale Deletions of the Human Mitochondrial Genome: A New Autosomal Dominant Disease. Am. J. Hum. Genet. 47:904-914, 1990.

Zhang et al., Multiple mitochondiral DNA deletions in an elderly human individual, FEBS Lett, 297, 34-38 1992.

Zhang, C., et al., Occurrence of a Particular Base Substitution (3243 A to G) in Mitochondrial DNA of Tissues of Ageing Humans. BioChem. BioPhys. Res. Comun., 195: 1104-1110, 1993.

Jessie B et al., "Accumulation of mitochondrial DNA deletions in the aging prostate." Proceedings of the American Association for Cancer Research Annual, vol. 42, Mar. 2001, pp. 862-863, XP001153110.

92ND Annual Meeting of the American Association for Cancer Research; New Orleans, LA, USA; Mar. 24-28, 2001. ISSN: 0197-016X.

Thayer R et al., "Mitochondrial DNA mutations and/or deletions in prostate cancers," Proceedings of the American Association for Cancer Research Annual, vol. 42, Mar. 2001, pp. 532-533, XP001153105. 92nd Annual Meeting of the American Association for Cancer Research, New Orleans, LA, USA; Mar. 24-28, 2001. ISSN: 0197-016X.

Petros JA. et al., "Mitochondrial DNA point mutations are common in prostate cancer and enhance malignant phenotype," Proceedings of the American Association for Cancer Research Annual, vol. 42, Mar. 2001, p. 517, XP001153111. 92nd Annual Meeting of the American Association for Cancer Research, New Orleans, LA, USA; Mar. 24-28, 2001. ISSN: 0197-016X.

Jeronimo C. et al., "Mitochondrial mutations in early stage prostate cancer and bodily fluids," Proceedings of the American Association for Cancer Research Annual, vol. 42, Mar. 2001, p. 63, XP001153112. 92nd Annual Meeting of the American Association for Cancer Research, New Orleans, LA, USA; Mar. 24-28, 2001. ISSN: 0197-016X.

Eshaghian A. et al., "Alterations of mitochondrial DNA in aging skin and in non-melanoma skin cancers," Proceedings of the American Association for Cancer Research Annual, vol. 43, Mar. 2002, pp. 304-305, XP001153120, 93rd Annual Meeting of the American Association for Cancer Research, San Francisco, California, USA, Apr. 6-10, 2002, ISSN: 0197-016X.

Hardy et al. Ethnic Differences and Disease Phenotypes. Science 2003 vol. 300, p. 737-781.

Hirschorn et al. A comprehensive review of genetic association studies. 2002 Genetics in Medicine p. 45-61.

Lucentini, J., Gene association studies typically wrong, reproducible gene-disease associations are few and far between, The Scientist, Dec. 20, 2004, p. 20.

Ioannidis J. et al, Replication validity of genetic association studies. Nature Genetics 2001 vol. 29 p. 306-309.

Buzzi et al. mtDNA A3243G MELAS mutation is not associated with multigenerational female migraine. Neurology 2000 vol. 54 p. 1005-1007.

Kogelnik Andreas M et al., "MITOMAP: a human mitochondrial genome database—1998 update," Nucleic Acids Research, Oxford University Press, Surrey, GB, vol. 26, No. 1, 1998, pp. 112-115, XP002966479, ISSN: 0305-1048.

Bandelt Hans-Jurgen et al., "What is 'novel' mtDNA mutation—and does 'novelty' really matter?" Journal of Human Genetics 2006, vol. 51, No. 12, 2006, pp. 1073-1082, XP002450142, ISSN: 1434-5161.

Croation Medical Journal, vol. 42, No. 3, 2001, Thomas J. Parsons et al., "Increasing the forensic discrimination of mitochondrial DNA testing through analysis of the entire mitochondrial DNA genomes", pp. 304-309.

Nature, vol. 408, Dec. 2000, Max Ingman et al., "Mitochondrial genome variation and the origin of modern humans," pp. 708-713.

Genomics, vol. 55, 1999, Barbara C. Levin et al., "A human mitochondrial DNA standard reference material for quality control in forensic identification, medical diagnosis, and mutation detection," pp. 135-146.

Biotechniques, vol. 32, No. 1, Jan. 2002, H. Andreasson et al: "Mitochondrial Sequence Analysis for Forensic Identification Using Pyrosequencing Technology," pp. 124-133.

Harbottle et al., Implications of Using the ND1 Gene as a Control Region for Real-Time PCR Analysis of Mitochondrial DNA Deletions in Human Skin. The Journal of Investigative Dermatology: 1518-1521, 2004.

Maitra, A. et al. The Human MitoChip: A High-Throughput Sequencing Microarray for Mitochondrial Mutation Detection. Genome Res. May 2004, vol. 14, No. 5, pp. 812-819 (plus cover page), ISSN 1088-9051.

Krishnan, K.J. et al. The Use of a 3895 bp Mitochondrial DNA Deletion as a Marker for Sunlight Exposure in Human Skin. J. Invest. Dermatol. Dec. 2004, vol. 123, No. 6, pp. 1020-1024. ISSN 0022-202X.

Prithivirajsingh, S. et al. Accumulation of Common Mitochondrial DNA Deletion Induced by Ionizing Radiation. FEBS Lett. Aug. 2004, vol. 571, pp. 227-232. ISSN 0014-5793.

Chabi, B. et al., Quantification of Mitochondrial DNA Deletion, Depletion,and Overreplication: Application to Diagnosis. Clin. Chem. Aug. 2003, vol. 49, No. 8, pp. 1309-1317. ISSN 0009-9147.

Mutation Research, 2000, vol. 468, pp. 35-43. CC to TT mutation in the mitochondrial DNA of normal skin: relationship to ultraviolet light exposure, Kawasaki et al.

Nucleic Acids Res., 1998, vol. 26, No. 6, pp. 1396-1400. Denaturing high performance liquid chromatography (DHPLC) used in the detection of germline and somatic mutations, Liu et al.

Parrella P. et al., Detection of Mitochondrial DNA Mutations in Primary Breast Cancer and Fine-Needle Aspirates, Cancer Research, 61, 7623-7626, 2001.

Chen, J. et al., Extensive Somatic Mitochondrial Mutations in Primary Prostate Cancer Using Laser Capture Microdissection, Cancer Research, 62, 6470-6474, 2002.

Fliss, M. et al., Facile Detection of Mitochondrial DNA Mutations in Tumors and Bodily Fluids, Science, 287, 2017-2019, 2000.

Jeronimo, C. et al., Mitochondrial mutations in early stage prostrate cancer and bodily fluids, Oncogene, 20, 5195-5198, 2001.

Chen, J. et al., Simultaneous generation of multiple mitochondrial DNA mutations in human prostrate tumors suggests mitochondrial hyper-mutagenesis, Carcinogenesis, vol. 24, No. 9, pp. 1481-1487, 2003.

Burgart, L. et al, Somatic Mitochondrial Mutation in Gastric Cancer, American Journal of Pathology, 147, 1105-1111, 1995.

Jessie, B. et al., Accumulation of mitochondrial DNA deletions in the malignant prostate of patients of different ages, Experimental Gerontology 37: 169-174 (2001).

Harbottle and Ma Birch-Machin A. "Real-time PCR analysis of a 3895 bp mitochondrial DNA deletion in nonmelanoma skin cancer and its use as a quantitative marker for sunlight exposure in human skin," British Journal of Cancer, Nature Publishing Group, London, GB, vol. 94, No. 12, Jan. 1, 2006, pp. 1887-1893.

MITOCHONDRIAL MUTATIONS AND REARRANGEMENTS AS A DIAGNOSTIC TOOL FOR THE DETECTION OF SUN EXPOSURE, PROSTATE CANCER AND OTHER CANCERS

CROSS-REFERENCE TO RELATED APPLICATIONS

This application is a Continuation of International Application PCT/CA2006/000652, filed 18 Apr. 2006, which claims priority from U.S. Provisional applications 60/789,872, filed 7 Apr. 2006; 60/721,522, filed 29 Sep. 2005; and 60/672,016, filed 18 Apr. 2005.

TECHNICAL FIELD OF THE INVENTION

This invention is related to the field of mitochondrial genomics. In particular it is related to mutations and rearrangements in the mitochondrial genome and their utility as an indicator of sun exposure, aging, and the genesis or existence of disease, for example detecting the presence of pre-neoplasia, neoplasia and progression towards potential malignancy before common clinical symptoms are evident.

BACKGROUND OF THE INVENTION

The current mega-trend in the biological sciences is the human genome project, and commercial exploitation of the data. However, there is an exceptional limitation to the use and implementation of this information as the data is not specific at the level of the individual. Incredibly the data is from only a few individuals, hardly representative of the variation present in human populations, rendering the data useful in general applications only. The staggering complexity of the human genome makes application on an individual basis impractical. To sequence completely one human nuclear genome the U.S. Department of Energy and the National Institute of Health have invested 2.5 billion dollars since 1988 (http://www.oml.gov/hgmis/project/budget.html).

Mitochondrial Genome

The mitochondrial genome is a compact yet critical sequence of nucleic acid. The mitochondrial genome codes for enzyme subunits necessary for cellular respiration. Mitochondrial DNA, or "mtDNA", is a minuscule genome of nucleic acid at 16,569 base pairs (bp) Anderson et al., 1981; Andrews et al., 1999) in contrast to the immense nuclear genome of 3.3 billion bp. Its genetic complement is astronomically smaller than that of its nuclear cell mate (0.0005%). However, individual cells carry anywhere from $10^3$ to $10^4$ mitochondria depending on specific cellular function (Singh and Modica-Napolitano 2002). Communication or chemical signalling, routinely occur between the nuclear and mitochondrial genomes (Sherratt et al., 1997). Moreover, specific nuclear components are responsible for maintenance and integrity of mitochondrial sequence (Croteau et al., 1999). When these nuclear areas are rendered non-functional by nuclear rearrangements indicative of potential disease, then mutations begin to appear in mtDNA sequences. In addition, specific mitochondria may be identified for intracellular destruction by deletions prompted by somatic mutations in the mitochondrial genome. This theoretical mechanism may serve as an indication of impending disease as well. About 3,000 genes are required to make a mitochondrion, with only thirty-seven of these coded by the mitochondrial genome, indicating heavy mitochondrial dependence on nuclear loci (Naviaux, 1997).

All mitochondrial DNA (mtDNA) genomes in a given individual are identical given the clonal expansion of mitochondria within the ovum, once fertilization has occurred. The essential role of mtDNA is the generation of the cellular fuel, adenosine triphosphate (ATP), which fires cellular metabolism. Significantly, the mitochondrial genome is dependent on seventy nuclear encoded proteins to accomplish the oxidation and reduction reactions necessary to this vital function, in addition to the thirteen polypeptides supplied by the mitochondrial genome (Leonard and Shapira, 1997). Different tissues and organs depend on oxidative phosphorylation to a varied extent. Diseases related to defective oxidative phosphorylation (OXPHOS) appear to be closely linked to mtDNA mutations (Byrne, 1992). Consequently as OXPHOS diminishes due to increased severity of mtDNA mutations, organ specific energetic thresholds are exceeded which give rise to a variety of clinical phenotypes. Moreover, mutations in the mitochondrial genome are associated with a variety of chronic, degenerative diseases (Gattermann et al. 1995). It is well known that aging and specific types of pathology can alter, or mutate mtDNA compromising the energy production capacity of the cell. This often results in over-expression of defective mitochondria, and/or the cell supplementing the lack of ATP by becoming more glycolytic (Carew and Huang, 2002); therefore, changes or mutations, in the mitochondrial genome can be used as markers for disease genesis and/or disease progression, when monitored at successive intervals.

Recently, Fliss et al. (2000) found, in primary tumors from lung and bladder cancer, a high frequency of mtDNA mutations which were predominantly homoplasmic in nature, indicating that the mutant mtDNA was dominant in the malignant cells. Point mutations and deletions would appear to be the non-programmed but unavoidable side effect of oxygen free radical damage to the membrane and genome of mitochondria (Miquel et al. 1992). This theory is plausible because not only is the mitochondrial genome lacking protective histones, but also is vulnerable to oxidative damage being found near the oxygen generating inner mitochondrial membrane. Moreover, as mtDNA has a compact genome and lacks introns, deleterious events are thus likely to affect a coding sequence resulting in a biochemical dysfunction. This dysfunction will further increase cellular oxidative stress which will lead to nuclear as well as mtDNA damage, thereby increasing the potential for a cell to enter into the cancer process (Penta et al., 2001). In this respect, research indicates that with increasing age there is an increase in mtDNA damage (Coitopassi & Wang 1995) and a subsequent decline in respiratory function (Miquel et al. 1992) leading to eventual cell death.

MtDNA as a Diagnostic Tool

MtDNA sequence dynamics are important diagnostic tools. Mutations in mtDNA are often preliminary indicators of developing disease, often associated with nuclear mutations, and act as biomarkers specifically related to disease, such as but not limited to: tissue damage and cancer from smoking and exposure to second hand tobacco smoke (Lee et al., 1998; Wei, 1998); longevity, based on accumulation of mitochondrial genome mutations beginning around 20 years of age and increasing thereafter (von Wurmb, 1998); metastatic disease caused by mutation or exposure to carcinogens, mutagens, ultraviolet radiation (Birch-Machin, 2000); osteoarthritis; cardiovascular, Alzheimer, Parkinson disease (Shoffner et al., 1993; Sherratt et al., 1997; Zhang et al, 1998); age associated hearing loss (Seidman et al., 1997); optic nerve degeneration and cardiac dysrhythmia (Brown et al., 1997; Wallace et al., 1988); chronic progressive external exopthalmoplegia (Taniike et al., 1992); atherosclerosis (Bogliolo et al., 1999); papillary thyroid carcinomas and thyroid tumours (Yeh et al., 2000); as well as others (e.g. Naviaux, 1997; Chinnery and Turnbull, 1999;).

Mutations at specific sites of the mitochondrial genome can be associated with certain diseases. For example, mutations at 4216, 4217 and 4917 are associated with Leber's Hereditary Optic Neuropathy (LHON) (Mitochondrial Research Society; Huoponen (2001); MitoMap). A mutation at 15452 was found in 5/5 patients to be associated with ubiquinol cytochrome c reductase (complex III) deficiency (Valnot et al. 1999). However, mutations at these sites were not found to be associated with prostate cancer.

Specifically, these alterations include point mutations (transitions, transversions), deletions (one base to thousands of bases), inversions, duplications, (one base to thousands of bases), recombinations and insertions (one base to thousands of bases). In addition, specific base pair alterations, deletions, or combinations of are associated with early onset of prostate, skin, and lung cancer, as well as aging (e.g. Polyak et al., 1998), premature aging, exposure to carcinogens (Lee et al., 1998), etc.

Since mtDNA is passed to offspring exclusively through the ovum, it is imperative to understand mitochondrial sequences through this means of inheritance. The sequence of mtDNA varies widely between maternal lineages (Ward et al., 1991), hence mutations associated with disease must be clearly understood in comparison to this variation. For example, a specific T to C transition noted in the sequence of several individuals, associated with a specific cancer, could in reality be natural variation in a maternal lineage widespread in a given particular geographical area or associated with ethnicity. For example, Native North Americans express an unusually high frequency of adult onset diabetes. In addition, all North American Natives are genetically characterized by five basic maternal lineages designated A, B, C, D, and X (Schurr et al., 1990; Stone and Stoneking, 1993; Smith et al., 1999). Lineage A is distinguished by a simple point mutation resulting in a Hae III site at bp 663 in the mitochondrial genome, yet there is no causative relationship between this mutation and the adult onset of diabetes. In addition, even within lineage clusters there is sequence variation.

Outside of the specific markers associated with a particular lineage there is more intrapopulation variation than interpopulation sequence variation (Easton et al., 1996; Ward et al., 1991, 1993;) This divergence must be understood for optimal identification of disease associated mutations, hence a maternal line study approach (Parsons et al., 1997), mimicking the strengths of a longitudinal design (i.e. subject tracking over a substantial period of time), must be used to identify mutations directly associated with disease, as opposed to mutations without disease association. Moreover, particular substances, such as second hand tobacco smoke, low levels of asbestos, lead, all known mutagens and at low levels in many environments, may be the cause of specific point mutations, but not necessarily a disease specific marker. Hence, a substantial mtDNA sequence database is a clear prerequisite to accurate forecasting of potential disease as a natural process, or through exposure to causative agents. Furthermore, the entire molecule must be sequenced for its full information content. The entire suite of point mutations (transitions, transversions), deletions (one base to thousands of bases), inversions, duplications, (one base to thousands of bases), recombinations and insertions (one base to thousands of bases) must be characterized as a whole over the entire mitochondrial genome. This ensures that all possible information available in the mitochondrial genome is captured. Although the genome of cytoplasmic mitochondria (16,569 bp) has been sequenced at an individual level, like its nuclear counterpart, the mitochondrial genome has not been sequenced at a population level for use as a diagnostic tool.

Recently mitochondria have been implicated in the carcinogenic process because of their role in apoptosis and other aspects of tumour biology (Green & Reed, 1998, Penta et al., 2001), in particular somatic mutations of mtDNA (mtDNA) have been observed in a number of human tumours (Habano et al. 1998; Polyak et al. 1998; Tamura et al. 1999; Fliss, et al. 2000). These latter findings were made more interesting by the claims that the particular mtDNA mutations appeared to be homoplasmic (Habano et al. 1998; Polyak et al. 1998; Fliss, et al. 2000). Additionally researchers have found that ultraviolet radiation (UV) is important in the development and pathogenesis of non-melanoma skin cancer (NMSC) (Weinstock 1998; Rees, 1998) and UV induces mtDNA damage in human skin (Birch-Machin, 2000a).

Moreover, through time, mitochondrial sequence loses integrity. For example, the 4977 bp deletion increases in frequency with age (Fahn et al., 1996). Beginning at age 20, this deletion begins to occur in small numbers of mitochondria. By age 80, a substantial number of molecules have been deleted. This deletion characterizes the normal aging process, and as such serves as a biomarker for this process. Quantification of this aging process may allow medical or other interventions to slow the process.

This application of mitochondrial genomics to medicine has been overlooked because mtDNA has been used primarily as a tool in population genetics and more recently in forensics; however, it is becoming increasingly evident that the information content of mtDNA has substantial application in the field of medical diagnostics. Moreover, sequencing the entire complement of mtDNA was a laborious task before the recent advent of high capacity, high-throughput robotic DNA sequencing systems. In addition, population geneticists were able to gather significant data from two highly variable areas in the control region; however, these small regions represent a small portion of the overall genome, less than 10%, meaning that 90% of the discriminating power of the data is left unused. Significantly, many disease associated alterations are outside of the control region. The character of the entire genome should be considered to include all sequence information for accurate and highly discriminating diagnostics.

Non-Melanoma Skin Cancer

Human non-melanoma skin cancer (NMSC) is the commonest cancer in many Caucasian populations (Weinstock, 1998; Rees, 1998). The majority of these tumours are basal cell carcinoma (BCC) and squamous cell carcinoma (SCC). BCCs are locally invasive and can cause significant morbidity but rarely metastasis. SCCs show significant metastatic potential and the occurrence of multiple NMSCs in patients with immunosuppression causes significant management problems (Rees, 1998). While there are no clinically identified pre-malignant lesions for BCC, some SCCs are thought to arise from precursor lesions, namely actinic keratoses (AKs) or areas of Bowen's disease (in situ carcinoma)(Rees, 1998).

SCCs show loss of heterozygosity affecting several chromosomes which suggests the involvement of several tumour suppressor genes in their development. Interestingly, in AKs, an equal or greater degree of genetic loss is observed in these precursor lesions compared to SCCs (Rehman et al. 1994; Rehman et al. 1996). This is important for the proposed invention because it suggests that other mechanisms, in addition to inactivation of tumour suppressor genes, are likely to be involved in the development of SCCs.

A role for mitochondria in tumourigenesis was originally hypothesised when tumour cells were found to have an impaired respiratory system and high glycolytic activity (Shay & Werbin, 1987). Recent findings elucidating the role of mitochondria in apoptosis (Green & Reed, 1998) together with the high incidence of homoplasmic mtDNA mutations in colon cancer (Habano et al. 1998; Polyak et al. 1998, reviewed in Penta et al., 2001), primary tumours of the bladder, neck and lung (Fliss et al. 2000), and gastric tumours (Tamura et al. 1999), further support this hypothesis. Furthermore, it has been proposed that these mitochondrial mutations may affect the levels of reactive oxygen species (ROS) which have been shown to be highly mitogenic (Polyak et al. 1998; Li et al. 1997).

Previous studies by the inventors and others have shown that mutations in mtDNA and the associated mitochondrial dysfunction is an important contributor to human degenerative diseases (Birch-Machin et al. 1993; Chinnery et al. 1999; Birch-Machin et al. 2000b). This is because the mitochondrial genome is particularly susceptible to mutations due to the high amounts of ROS produced in this organelle coupled with the lack of protective histones and a low rate of mtDNA repair (Pascucci et al. 1997; Sawyer & van Houten; LeDoux et al. 1999) compared to the nucleus. Indeed, the mutation rate for mtDNA is around ten times higher than that of nuclear DNA (Wallace, 1994). Most of the mtDNA mutations identified in the recent human tumour studies have indicated possible exposure to ROS derived mutagens. This is important for the investigation of mtDNA mutations in NMSC because there is recent evidence for the direct involvement of UV induced ROS in the generation of mtDNA deletions in human skin cells (Berneburg et al. 1999, Lowes et al., 2002). In addition, the major determinant of NMSC in individuals without protective pigmentation or genetic predisposition is UV (Weinstock, 1998). The putative precursor lesions of SCCs are also found predominantly on constant sun-exposed sites. This is important because work by the Birch-Machin laboratory has shown distinct differences between the incidence of mitochondrial DNA damage in skin taken from different sun-exposed body sites. The vast majority of the damage is found on constant sun-exposed sites (Krishanan et al., 2002).

One of the inventors was the first to quantitatively show that UV exposure induces mtDNA damage (Birch-Machin et al. 1998). MtDNA as a molecular marker was used to study the relation between chronological aging and photo aging in human skin. A 3-primer quantitative PCR (qPCR) method was used to study the changes in the ratio of the 4977 bp-deleted to wild type mtDNA in relation to sun exposure and chronological age of human skin. There was a significant increase in the incidence of high levels (i.e. >1%) of the 4977 bp-deleted mtDNA in sun-exposed (27%, [27/100]) compared with sun-protected sites (1.1% [1/90]) (Fishers exact test, P<0.0001). Deletions or mutations of mtDNA may therefore be useful as a marker of cumulative ultraviolet radiation exposure Furthermore, a study using a South-Western Blot approach involving monoclonal antibodies against thymine dimers, provided direct evidence for the presence of UV-induced damage in purified mtDNA (Ray et al. 1998).

Recent work from the inventors' research group has used a long extension PCR (LX-PCR) technique to amplify the entire mitochondrial genome in order to determine the whole deletion spectrum of mtDNA secondary to UV exposure (Ray et al. 2000). Long PCR analysis of 71 split skin samples, where the epidermis is separated from the underlying dermis, was performed in relation to sun exposure. There was a significant increase in the number of deletions with increasing UV exposure in the epidermis (Kruskal-Wallis test, p=0.0015). The findings in the epidermis are not confounded by any age-dependent increases in mtDNA deletions also detected by the long PCR technique. The large spectrum of identified deletions highlights the ubiquitous nature and the high mutational load of mtDNA associated with UV exposure. Compared to the detection of single deletions using competitive PCR, the study shows that long PCR is a sensitive technique and may therefore provide a more comprehensive, although not quantitative, index of overall mtDNA damage in skin. The studies by one of the inventors described above clearly show that mtDNA is a significant target of UV and this together with the role of mitochondrial in skin disease has been recently reviewed (Birch-Machin, 2000).

The pigmentation of human hair and skin which is the major co-variant of UV sensitivity and human skin cancer has been investigated. These investigations have centred on the association of variants of the melanocortin 1-receptor gene and sun-sensitivity of individuals and populations (Smith et al. 1998; Healy et al. 1999; Flanagan et al. 2000; Healy et al. 2000; Harding et al. 2000; Flanagan et al., 2002) relating to skin cancer susceptibility. However, these studies have not addressed population-level variation in mtDNA sequences in association with particular skin types and/or hair colour.

One of the questions which remains largely unanswered by the recent studies of mtDNA mutations in human tumours is the incidence of deletions of the mitochondrial genome in relationship to these tumours. This is an important question to answer because a preliminary study of a single patient in human skin has shown differences in the incidence of the common mtDNA deletion between several tumours (AKs and SCCs) and normal skin (Pang et al. 1994). As well, the inventors' own preliminary data shows an increased number of mtDNA deletions in tumours compared to normal skin. Finally, Birch-Machin and others have shown that the incidence of mtDNA deletions, as well as duplications, increases with increasing UV exposure (Berneburg et al. 1999; Birch-Machin et al. 1998; Ray et al. 1998; Ray et al. 1999; Ray et al. 2000), Lindsey et al., 2001; Birch-Machin et al., 2001; Lowes et al., 2002, Krishnan et al., 2002).

Apart from the questions relating to tumour progression other vital questions remain largely unanswered by the recent studies of mtDNA in human tumours (Habano et al. 1998; Fiiss et al. 2000). Firstly, due to technical limitations, it is not clear whether the mtDNA mutations are truly homoplasmic, as varying levels of heteroplasmy may indicate important disease transitions as well (Habano et al. 1998; Polyak et al. 1998; Fliss, et al. 2000); secondly, apart from one study (Tamura et al. 1999) the incidence of mtDNA deletions and their role as potential biomarkers for NMSC was not investigated. Researchers have looked at the common deletion and ignored the rest of the 100 or so deletions. As well, investigators have been focused on identification of mutations, rather than their quantification. It is important to assess accurately in a quantitative manner the incidence of deletions because of the threshold effect of mtDNA damage on ATP production and consequently cell function. In addition, deletions are difficult to characterize.

Long PCR is typically used which produces a ladder of deletions which then have to be characterized.

Current diagnosis of NMSC is pathological evaluation of excised tissue. Accordingly, there is a need for an early marker of UV-induced DNA damage which predisposes an individual to NMSC. There is also a need for a genetic-based diagnostic tool which allows for early detection and is diagnostically accurate.

Prostate Cancer

Prostate cancer is a frequently diagnosed solid tumour that most likely originates in the prostate epithelium (Huang et al. 1999). In 1997, nearly 10 million American men were screened for prostate specific antigen (PSA), the presence of which suggests prostate cancer (Woodwell, 1999). Indeed, this indicates an even higher number of men screened by an initial digital rectal exam (DRE). In the same year, 31 million men had a DRE (Woodwell, 1999). Moreover, the annual number of newly diagnosed cases of prostate cancer in the United States is estimated at 179,000 (Landis et al., 1999). It is the second most commonly diagnosed cancer and second leading cause of cancer mortality in Canadian men. In 1997 prostate cancer accounted for 19,800 of newly diagnosed cancers in Canadian men (28%) (National Cancer Institute of Canada). It is estimated that 30% to 40% of all men over the age of forty-nine (49) have some cancerous prostate cells, yet only 20% to 25% of these men have a clinically significant form of prostate cancer (SpringNet—CE Connection, internet, www.springnet.com/ce/j803a.htm). Prostate cancer exhibits a wide variety of histological behaviour involving both erogenous and exogenous factors, i.e. socio-economic situations, diet, geography, hormonal imbalance, family history and genetic constitution (Konishi et al. 1997; Hayward et al. 1998).

From a risk standpoint familial and hereditary prostate cancers are not considered synonymous terms. Familial cancers refer to the incidences within a family, but are not inherited. This form accounts for up to 25% of prostate cancers (Walsh & Partin, 1997). Hereditary refers to a subtype of prostate cancer with a Mendelian inheritance of a predisposing gene(s) and accounts for approximately 9% of reported cases. A positive family history of prostate cancer for this disease suggests that these predisposing gene(s) play an important role in prostate cancer development and progression. Recently, susceptibility genes on chromosomes 1 and X have been identified as predisposing men to prostate cancer, providing greater insight into the etiology of hereditary cancer (Berthon et al. 1998; Xu et al. 1998).

Prostate cancer prognosis mainly depends on the tumour stage and grade at diagnosis. Only localized prostate cancer can be cured by radical treatment. Standard detection still relies on digital rectal examination, PSA testing and histopathologic examination of prostatic biopsied tissues. Biopsy of a mass is used to confirm malignancy, it is not an early detection technique. Unfortunately, some early tumours are impossible to identify during rectal exams. PSA tests have a specificity of 60 to 70% and a sensitivity of 70 to 80% (personal communication, Dr. Sunil Gulavita, Northwestern Ontario Cancer Centre). A newer technique which refines diagnosis for tumours of common histologic grade is ploidy-DNA analysis employing flow cytometry (Shankey et al. 1995); however, this technique measures chromosomal changes that are only apparent in later stages of cancer development and is not sufficiently sensitive for the detection of minor alterations in DNA structure or chromosomal inversions, or reciprocal trans-locations in early cancers. The invention focuses on early detection since prognosis is heavily dependent on the stage of disease at diagnosis.

Our understanding of genetic abnormalities in prostate cancers is scanty. Research into prostate cancer has focussed on the development of knowledge in the following areas: 1) proto-oncogenes (Buttyan et al. 1987); 2) tumour suppressor genes (p53, p73, KAI1 and MMAC1/PTEN; Dong et al. 1995; Cairns et al. 1997) and 3) telomere/telomerase activity in metastasis. Up-regulation of telomerase and amplification of telomeric DNA in prostate cells may provide effective markers for diagnosis. Moreover, telomeres may serve as a site for therapy (Ozen et al. 1998). A number of groups have provided evidence for a "prostate cancer gene" in the short arm of chromosome 1 (Berthon et al. 1998). More work is needed to identify the specific locus within this region. It has been suggested that this marker is only one of several possible genes predisposing men to familial prostate cancer. Other studies have shown possible marker loci on the X chromosome (Xu et al. 1998). If some prostate cancers are polygenic, then mtDNA becomes an important diagnostic tool since it may be difficult to identify and understand the interplay between all associated nuclear genes in such cases.

Certainly, a key issue in prostate cancer research is to identify molecular markers that can effectively determine and distinguish tumour progression. Molecular markers may be able to discriminate between those cases of prostate neoplasmy which will proceed rapidly to metastatic disease and those with little chance of resulting in tumour development. Comparison of molecular markers or mutations can determine whether the tumor pathway is latent or aggressive. Up to the present research has focused primarily on the secrets hidden within the nuclear genome; however, the much smaller mtDNA genome seems to act as a barometer for events in the nucleus and as such provides a means for the early detection of human prostate cancer (Zeviani et al. 1990). Importantly, in this respect, mitochondria have been implicated in the carcinogenic process because of their role in apoptosis and other aspects of tumour biology (Green & Reed 1998). In particular, somatic mutations of mtDNA have been observed in a number of human tumours (Polyak et al. 1998, Tamura et al. 1999, Fliss et al. 2000). However, previous studies have been exclusively cross-sectional as they have not considered the clonal nature of mtDNA in maternal lines. These limited cross-sectional studies merely show the mutation at one time point. This may or may not give an accurate link between a mutation and the corresponding disease state. Cross-sectional studies employing a maternal line have the advantage of tracking a mutation in mtDNA over time and thus mimic the strength of a longitudinal design. Mutations which are common population variants, as opposed to mutations associated with disease can both be identified.

Aging

Aging consists of an accumulation of changes with time both at the molecular and cellular levels; however, the specific molecular mechanisms underlying the aging process remain to be elucidated. In an attempt to explain the aging process, mitochondrial genomes in older subjects are compared to the genomes of younger subjects from the same maternal lineage. One deletion associated with aging is known as the common deletion, or 4977-bp deletion. Aging research has been limited to this common deletion and polymorphisms in the control region. For a clear understanding of these mutations, the entire genome must be analyzed. Other deletions are seen in Table 1 adapted from Wei, 1992.

TABLE 1

| Deletions size (bp) | References |
|---|---|
| 4977 | Cortopassi and Arnheim, 1990; Ikebe et al., 1990; Linnane et al., 1990; Corral-Debrinski et al., 1991; Yen et al., 1991; Torri et al., 1992; Zhang et al., 1992 |

TABLE 1-continued

| Deletions size (bp) | References |
|---|---|
| 7436 | Corral-Debrinski et al., 1991; Hattori et al., 1991 Hsieh and Wei, 1992 |
| 3610 | Katayama et al., 1991 |
| 6063 | Hsieh and Wei, 1992 Yen et al., 1992 |
| 5827 | Zhang et al., 1992 |
| 6335 | Zhang et al., 1992 |
| 7635 | Zhang et al., 1992 |
| 7737 | Zhang et al., 1992 |
| 7856 | Zhang et al., 1992 |
| 8041 | Zhang et al., 1992 |
| 8044 | Zhang et al., 1992 |
| 5756 | Zhang et al., 1992 |

Oxygen free radicals, a normal by product of ATP production, are a probable cause of this deletion, which increases in frequency with age. Existing literature demonstrates a strong association between mtDNA (mtDNA) mutations, chronological age, and the overall aging process in postmitotic tissues such as muscle and brain; however, comparative maternal line studies are needed to discriminate between aging associated mutational events and those mutations without an aging association.

In recent years a variety of chronic degenerative diseases have been shown to result from mutations in mtDNA (Gatterman et al. 1995). Diseases related to defective OXPHOS appear to be closely linked to mtDNA mutations (Byrne, 1992). Furthermore, it has been shown that these myopathies are often associated with the common deletion of 4977-bp of the mitochondrial genome (Liu et al. 1997). This large deletion has also been found, at heteroplasmic levels, in various tissues of normal aging persons and is consistent with the Mitochondrial Theory of Aging (Harman, 1981). This is manifest through an increase in the deletion frequency (Cortopassi & Wang, 1995) and a subsequent decline in respiratory function (Miquel et al. 1992) resulting in eventual cell death in old age. The early detection of a predisposition to a disease or disorder presents the best opportunity for medical intervention, as early genetic diagnosis may improve the prognosis for a patient.

Previous studies employing a cross-sectional design have established an association or cause and effect relationship between mtDNA mutations, deletions, and/or combinations of such and aging; however, in order to obtain accurate data the age specific deletion and/or mutation rate must be determined concisely. Attributing mutations to the aging process as opposed to a particular disease at the population level is vital. This information is imperative to an understanding of how mtDNA damage accrues over time. Moreover, the consequences of these particular mutations, their frequencies, and associations in the temporal aspects of aging must be known in order to forecast and eventually slow aging at the molecular level. Researchers have not yet determined this rate, which requires evaluation of population data through maternal lines. Accordingly, there is a need for a biomarker which tracks the aging process.

Accordingly, there is a need for a simple, straightforward system of monitoring the mitochondrial genome for mutations which indicate early stage cancer, aging or other human diseases with a DNA component. There is also a need for a simple diagnostic system for sun exposure, non-melanoma skin cancer, prostate cancer, lung cancer and aging linked to defects in the mitochondrial genome. There is a need for a diagnostic system which differentiates between mutations in mtDNA which cause disease, and those which simply represent variation within and between populations.

REFERENCE TO COMPUTER PROGRAM LISTING/TABLE APPENDIX

The present application includes a sequence listing appendix on compact disc. Two duplicate compact discs are provided herewith. The sequence listings on each disc are identical and are hereby incorporated by reference in their entirety. Each compact disc contains an ASCII text file of the computer program listing as follows:
Filename: BCGP112US_sequence listing (2).txt
Size: 808 KB
Date Created Feb. 9, 2009

SUMMARY OF THE INVENTION

Aspects of the present invention are listed in the claims.

For example, an of the invention is to provide a method for detecting a predisposition to cancer, early detection of cancer, genesis of cancer, presence of cancer, progression of cancer, absence of cancer, or sun exposure in a biological sample having mtDNA, comprising (a) providing a biological sample comprising mtDNA and (b) detecting a deletion in the mtDNA.

Another aspect of the invention is to provide an array comprising a plurality of nucleic acid members, and a solid substrate, wherein each of the nucleic acid members is associated with at least one deletion associated with predisposition to cancer, early detection of cancer, genesis of cancer, presence of cancer, progression of cancer, absence of cancer, sun exposure or aging, and is chosen from mitochondrial DNA, RNA transcribed from mitochondrial DNA, and cDNA, wherein each nucleic acid member has a unique position on said array and is stably associated with the solid substrate.

Another aspect of the invention is to provide a kit for diagnosing a predisposition to cancer, early detection of cancer, genesis of cancer, presence of cancer, progression of cancer, absence of cancer or sun exposure comprising at least one member selected from the group consisting of: solid support, the array describe above, means for holding the solid support, means for extraction of mitochondrial DNA, means for access to a database of mitochondrial DNA sequences, primers, reagents and instructions Another aspect of the invention is to provide a database containing mitochondrial DNA sequences chosen from normal control sequences associated with non-disease states, sequences associated with interpopulation variations, sequences associated with intrapopulation variations, or sequences associated with a predisposition to cancer, early detection of cancer, genesis of cancer, presence of cancer, progression of cancer, absence of cancer, sun exposure or aging.

Another aspect of the invention is to provide a method of detecting a deletion spanning approximately nucleotides 10744 to 14124 of the mtDNA genome, wherein said deletion is associated with prostate cancer, in a subject having mtDNA, comprising (a) providing a biological sample from the subject and (b) detecting the presence of the deletion in the mtDNA. The deletion may be in the range of 3000 to 4000 bp. The deletion may be approximately 3379 bp. The deletion may deletes all or part of base pairs between 10744 and 14124, comprising substantially genes encoding NADH dehydrogenase subunit 4L, NADH dehydrogenase subunit 4, NADH dehydrogenase subunit 5, tRNA histidine, tRNAserine2, and tRNA leucine2.

Another aspect of the invention is to provide a nucleic acid primer 3.4 forward comprising TAG ACT ACG TAC ATA CTA ACC CTA CTC CTA (SEQ ID NO: 139) and a nucleic acid primer 3.4 reverse comprising GAG GTA GGA TTG GTG CTG T (SEQ ID NO: 140).

Another aspect of the invention is to provide an array comprising a plurality of nucleic acid members, and a solid substrate, wherein one of the nucleic acid members is associated with the mtDNA deletion at approximately 10744 to 14124, wherein the nucleic acid member has a unique position on said array and is stably associated with the solid substrate.

Another aspect of the invention is to provide a kit for diagnosing skin cancer comprising at least one member selected from the group consisting of: a disposable chip, an array, means for holding the disposable chip, means for extraction of mtDNA, primers, reagents and instructions.

Another aspect of the invention is to provide a method of monitoring a person for the progression toward prostate cancer or progression of prostate cancer, in a biological sample from a subject, comprising: providing a biological sample from the subject; extracting DNA from the biological sample; detecting the absence or presence of deletions of the mtDNA; determining whether the deletions are associated with normal interpopulation or intrapopulation variations, or whether the deletions are associated with the absence or presence of a predisposition to prostate cancer, progression toward prostate cancer, prostate cancer or progression of prostate cancer, and; repeating the steps.

Another aspect of the invention is to provide a use of a deletion between approximately 10744 and 14124 of the mtDNA comprising all or part of NADH dehydrogenase subunit 4L, NADH dehydrogenase subunit 4, NADH dehydrogenase subunit 5, tRNA histidine, tRNAserine2, and tRNA leucine2 to detect a predisposition to prostate cancer, early detection of prostate cancer, genesis of prostate cancer, presence of prostate cancer, or progression of prostate cancer in a subject having mtDNA.

Another aspect of the invention is to provide a method for confirming or refuting a prostate cancer biopsy test from a biopsy sample, comprising: obtaining normal tissue from a biopsy sample; and detecting the absence or presence of a mtDNA deletion of approximately 3379 bp in the normal tissue.

Another aspect of the invention is to provide a method for three-dimensional prostate tumour mapping, comprising: obtaining sextant needle biopsy samples; and detecting the absence or presence of a mtDNA deletion of approximately 3379 bp in each of the sextant samples.

Another aspect of the invention is to provide a method for the collection of a patient sample for use in diagnosing prostate cancer sun exposure by using a deletion spanning approximately nucleotides 10744 to 14124 of the mtDNA genome, comprising: providing a biological sample from the subject.

Another aspect of the invention is to provide a mitochondrial deletion spanning approximately nucleotides 10744 to 14124 of the mtDNA genome for use in diagnosing prostate cancer.

Another aspect of the invention is to provide a method for detecting sun exposure or non-melanoma skin cancer.

Another aspect of the invention is to provide a method of detecting a deletion spanning approximately nucleotides 547 to 4443 in the minor arc of the mtDNA genome, wherein said deletion is associated with skin cancer and/or sun exposure, in a subject having mtDNA, comprising: providing a biological sample from the subject; and detecting the presence of the deletion in the mtDNA. Another aspect of the invention is to provide a method for determining the cumulative UV exposure, in a subject having mtDNA, comprising: providing a biological sample from the subject; and detecting the presence of the deletion in the mtDNA. A similar method may also be used of monitoring the long term safety of clinical UV phototherapy regimes. The deletion may be in the range of 3500 to 4000 bp. The deletion may be approximately 3895 bp, comprising a span of mtDNA from approximately mtTF1 binding site in the D-loop to tRNA methionine. The deletion may delete all or part of base pairs between 547 to 4443 in the minor arc of the mtDNA genome, comprising substantially a 12s rRNA gene, a 16s rRNA gene, a ND1 gene and promoters for transcription of H and L strands.

Another aspect of the invention is to provide a nucleic acid primer L404 comprising CTT TTG GCG GTA TGC ACT TT (SEQ ID NO: 145) and a nucleic acid primer H4676 comprising GAT TAT GGA TGC GGT TGC TT (SEQ ID NO: 146).

Another aspect of the invention is to provide a nucleic acid probe, 3895-probe, comprising TGC TAA CCC CAT ACC CCG AAA ATG TTG G Tamra (SEQ ID NO: 153).

Another aspect of the invention is to provide an array comprising a plurality of nucleic acid members, and a solid substrate, wherein one of the nucleic acid members is associated with the mtDNA deletion at approximately 547 to 4443, wherein the nucleic acid member has a unique position on said array and is stably associated with the solid substrate.

Another aspect of the invention is to provide a kit for diagnosing skin cancer comprising a disposable chip, the array described above, means for holding the disposable chip, and means for extraction of mtDNA.

Another aspect of the invention is to provide a method of monitoring a person for sun exposure and non-melanoma skin cancer, in a biological sample from a subject, comprising: providing a biological sample from the subject; extracting DNA from the biological sample; detecting the absence or presence of deletions of the mtDNA; determining whether the deletions are associated with normal interpopulation or intrapopulation variations or whether the deletions are associated with sun exposure, and; repeating the steps.

Another aspect of the invention is to provide a use of a deletion between approximately 547 to 4443 in the minor arc of the mtDNA genome in a subject having mtDNA to detect sun exposure or non-melanoma skin cancer.

Another aspect of the invention is to provide a method for the collection of a patient sample for use in diagnosing skin cancer by using a deletion spanning approximately nucleotides 547 to 4443 in the minor arc of the mtDNA genome, comprising: providing a biological sample from the subject.

Another aspect of the invention is to provide a mitochondrial deletion spanning approximately nucleotides 547 to 4443 of the minor arc of the mtDNA genome for use in diagnosing sun exposure or skin cancer.

Another aspect of the invention is to provide a use of the deletion junction sequence of SEQ ID NO: 147 to confirm the presence of the 3895 bp mtDNA deletion associated with sun exposure or NMSC.

Another aspect of the invention is to provide a method for a sensitive detection of a rearrangement in a DNA sample, wherein the rearrangement creates a newly formed junction in the DNA sequence of a sample, comprising: providing a DNA sample comprising or suspected of comprising a rearrangement; providing a primer or a probe which spans the newly formed junction created by the rearrangement; detecting the rearrangement by amplifying or probing the junction. The rearrangement may be in mtDNA. The rearrangement may be a deletion.

A BRIEF DESCRIPTION OF THE DRAWINGS

FIG. 8a) is a representative ethidium bromide stained agarose gel showing a greater frequency of the 3895 by deletion in usually sun exposed skin compared with occasionally sun-exposed skin.

FIG. 8b) is a histogram of the frequency of the 3895 by deletion in 104 split skin samples taken from different sun exposed body sites.

Figure 9:

FIG. 9 is a gel showing the UV-inducible increase of the 3895 by deletion observed after 17 repetitive doses of UVR.

Figure 10:
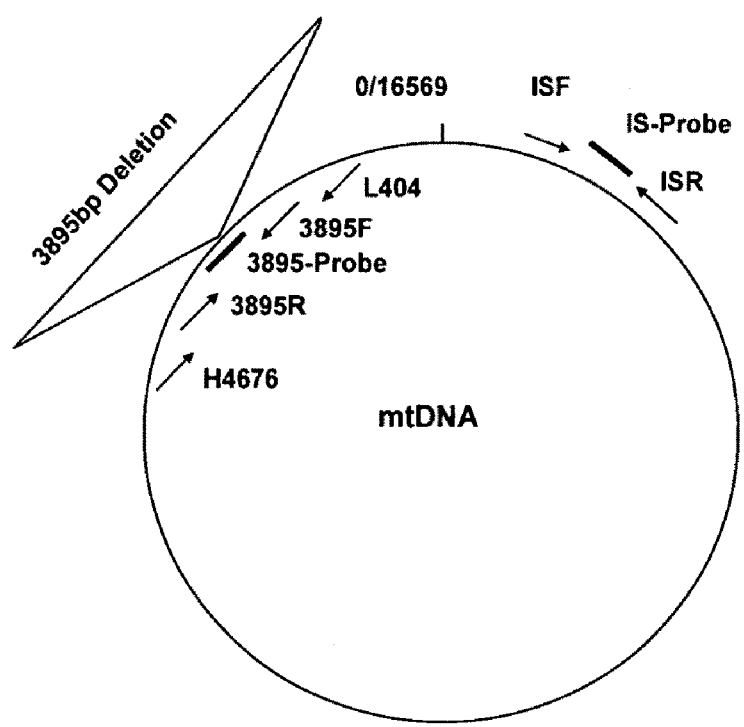

FIG. 10 is a schematic representation of the localisation of PCR primers and TaqMan probes on mtDNA used in Example 14 to detect the 3895 by deletion.

Figure 11:
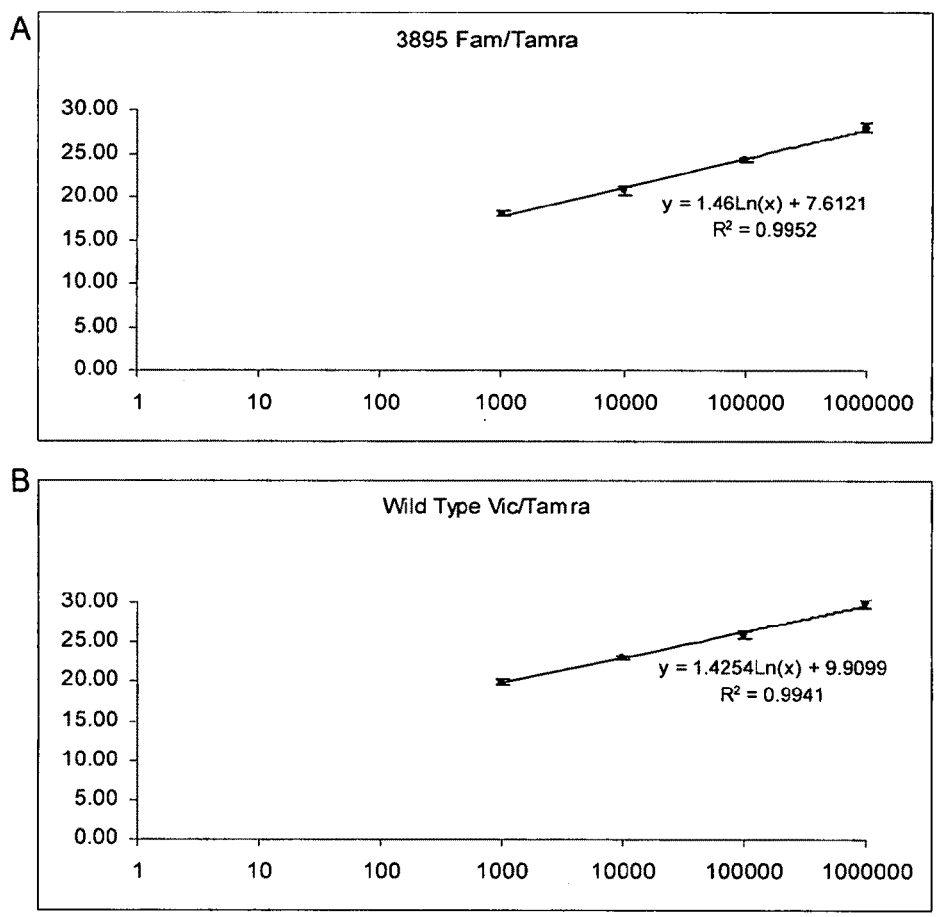

FIG. 11 is two graphs showing the linear relationship between template concentration and the threshold cycle number (CT) for the 3895 by deletion (A) and wildtype internal standard (B).

Figure 12:
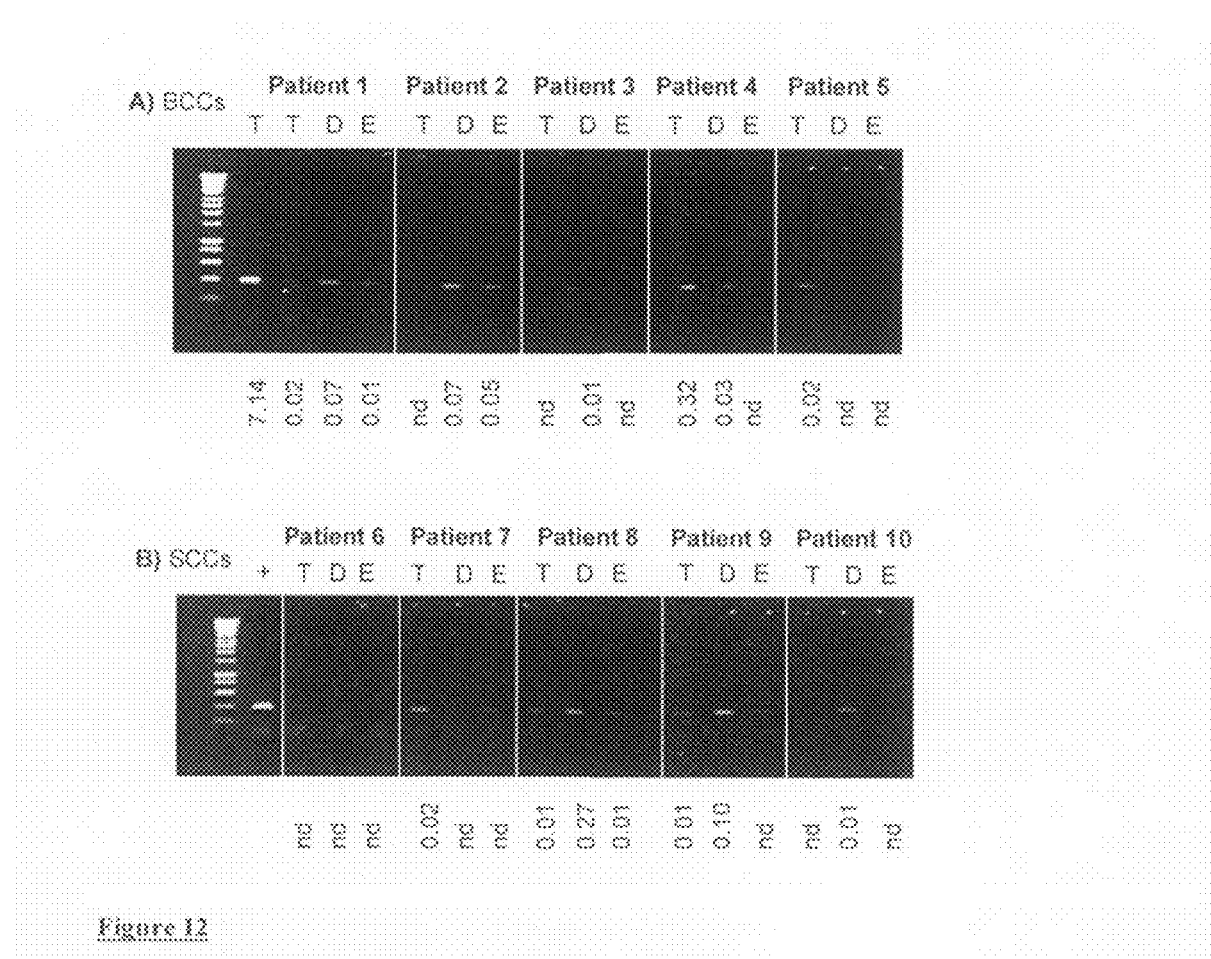

FIG. 12 is a photograph of an ethidium bromide stained agarose gel showing the incidence of the 3895 by deletion in tumour (T) and histologically normal perilesional dermis (D) and epidermis(E) from both BCCs (FIG. 12A) and SCCs (FIG. 12B).

Figure 13:
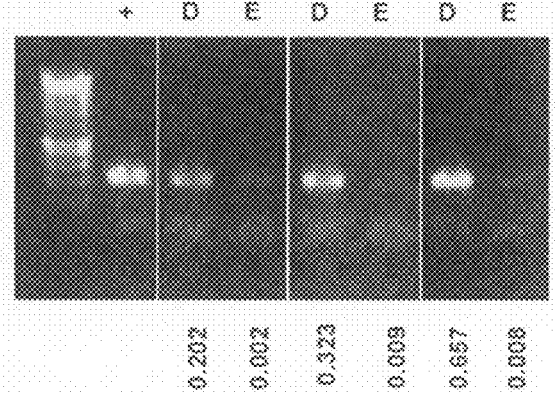
Figure 13:
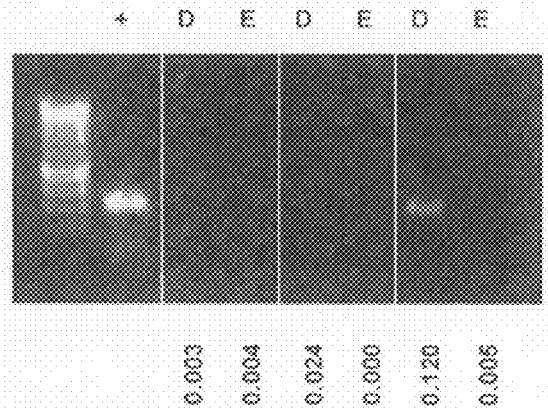

FIG. 13 is a photograph of representative ethidium bromide agarose gels showing typical examples of their corresponding level of 3895 deletion as detected by realtime PCR of three pairs of sun exposed samples (FIG. 13a) and three pairs of sun intermittent samples (FIG. 13B).

Figure 14:
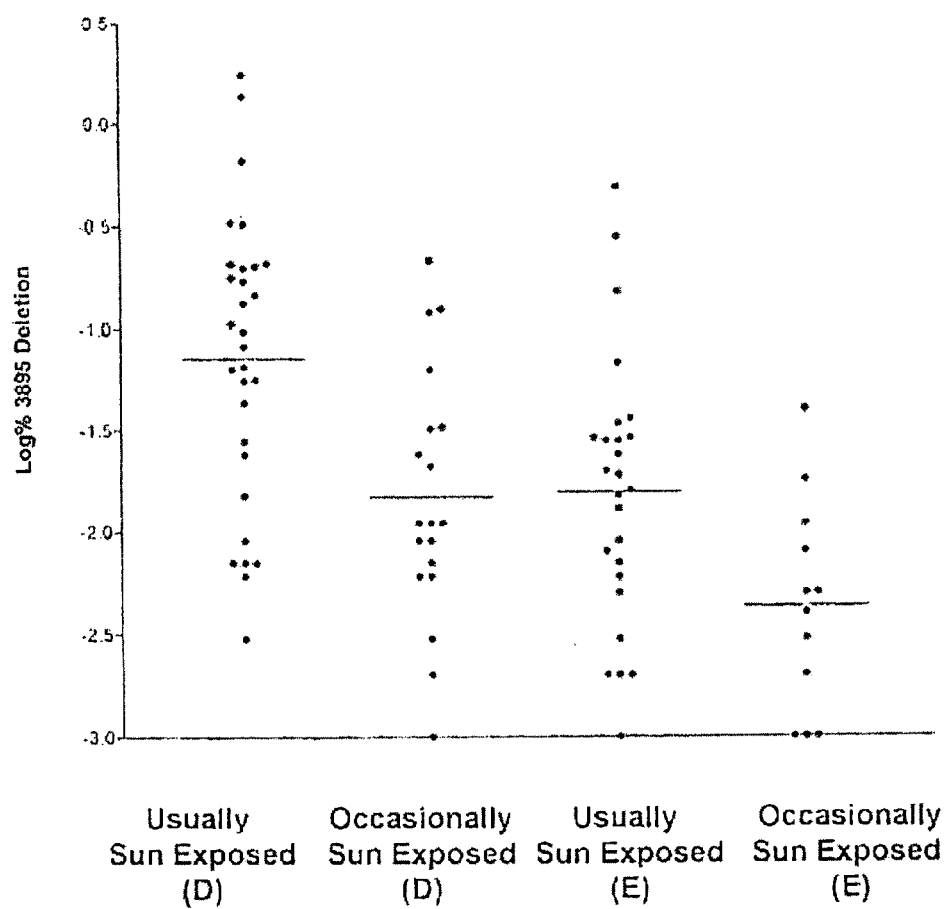

FIG. 14 is a scatter plot showing the levels of the 3895 by deletion expressed as a percentage in sun exposed and sun intermittent dermis and epidermis as determined by realtime PCR.

Figure 15:
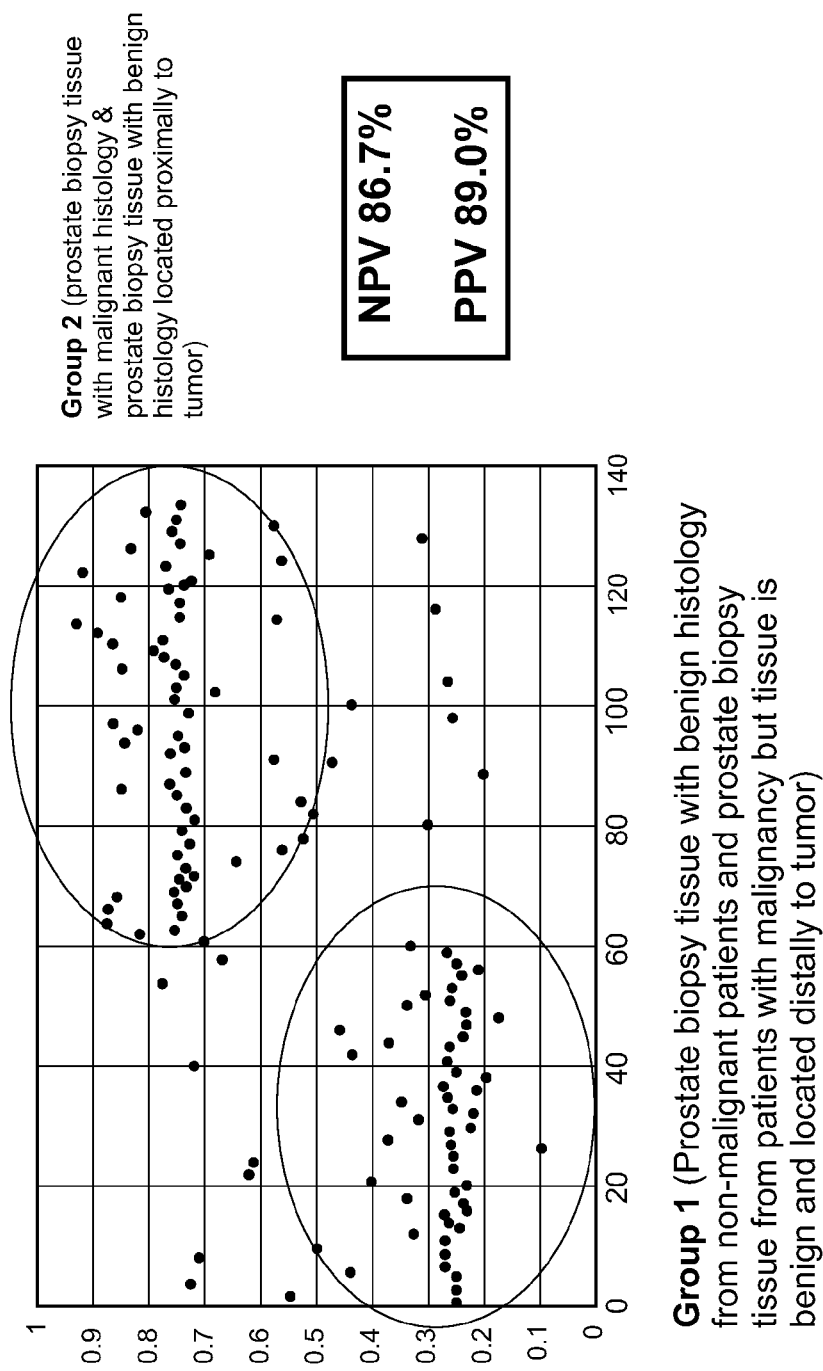

FIG. 15 is a diagram showing the relationship between biopsy results and mtDNA analysis in diagnosing prostate tumour.

BRIEF DESCRIPTION OF THE TABLES

Table 1 is a summary of mutations associated with aging.

Table 1a is a principal component analysis of mutations in mtDNA of seven protein coding regions in control, distant benign, adjacent benign and malignant tissue.

Table 1b is a neural network analysis of mutations in mtDNA of seven protein coding regions in control, distant benign, adjacent benign and malignant tissue.

Table 1c is a summary of the synonymous and non-synonymous mutations found in ND1, ND2, COXI and CYTB regions of the mitochondria of 31 patients having prostate cancer from distant benign, adjacent benign and malignant prostate tissue.

Table 1d is a Chi square analysis of mutations in mitochondrial DNA in distant benign tissue from malignant glands versus prostate tissue from symptomatic but not malignant subjects.

Table 2 is a summary of the mean number of deletions is epidermal tumours and adjacent normal tissues.

Table 3 is summary of the standard method of DHPLC.

Table 4 is a summary of mitochondrial mutations (including D-loop) from prostate needle biopsies and complete genome mutations from malignant, adjacent and distant benign prostate glands from patients with prostate cancer.

Table 5 is a list of primers used for complete mitochondrial genome amplification for formalin fixed and normal tissues from blood.

Table 6 is a list of amplification primers for use with Example 12.

Table 7 is qPCR Components of Example 12.

Table 8 shows the cycling parameters for Example 12.

Table 9 is a list of probes used in Example 14.

DETAILED DESCRIPTION OF THE INVENTION

The method of the present invention can be used to diagnose diseases linked to mtDNA. The method of the present invention provides for analysis of the mitochondrial genome of an individual from a biological sample, for example by amplification of the mitochondrial genome, sequencing a portion of the mitochondrial genome, preferably the entire mitochondrial genome of the individual using any known means. Denaturing high performance liquid chromatography (DHPLC) may also be used to rapidly screen many samples. DHPLC can focus on hotspots of mutations. DHPLC is more sensitive than automated sequencing in terms of detecting mutations, and can even detect 2% heteroplasmy, compared with 20-25% for ordinary sequencing. Methods for detecting lower levels of heteroplasmy (<2%) may also be developed.

As used herein, "actinic kerotoses" means proposed precursor epidermal lesion of a squamous cell carcinoma.

As used herein, "aging" refers to an accumulation of changes with time, both at the molecular and cellular levels.

As used herein, "alleles" means one of several alternative forms of a given DNA sequence occupying a specific place on a chromosome.

As used herein, "artificial neural network (ANN)" means a virtual device in which several interconnected elements process information simultaneously, adapting and learning from past patterns.

As used herein, "attaching" or "spotting" refers to a process of depositing a nucleic acid onto a solid substrate to form a nucleic acid array such that the nucleic acid is irreversibly bound to the solid substrate via covalent bonds, hydrogen bonds or ionic interactions.

As used herein, "atypical" or "abnormal" means cellular appearance which is not normal, but also does not appear to be malignant.

As used herein, "basal cell carcinoma" means a type of cancer of skin cells.

As used herein, "benign" means of no danger to health; not recurrent or progressive; not malignant.

As used herein, "benign prostatic disease" can include, but is not limited to, hyperplasia, inflammation, atrophy, prostatis, metaplasia, and prostatic intraepithelial neoplasia.

As used herein, "Bowen's disease" means in situ epidermal carcinoma.

As used herein, "cycle threshold" ($C_T$) is the point at which target amplification rises above background, as indicated by a signal such as a fluorescence signal.

As used herein, "diagnostic" or "diagnosing" means using the presence or absence of a mutation or combination of mutations as a factor in disease diagnosis or management. The detection of the mutation(s) can be a step in the disease state diagnosis.

As used herein, "disease" includes a disorder or other abnormal physical state.

As used herein, "disease associated mitochondiral genomes" means genomes containing mutations indicative or otherwise associated with a particular disease.

As used herein, "database" means an electronic storage system (computer based using standard industry software) which will have the capacity to store and provide retrievable information that will enable researchers to rapidly determine the structure of the nucleotide sequences. The database will also store descriptive information about those individuals who provide the biological samples. This descriptive information will include health status and other pertinent indices which may be correlated to the biological sample.

As used herein, "deletions" means removal of a region of DNA from a contiguous sequence of nucleic acids, where once a deletion has occurred, the gap is repaired by rejoining of the ends. Deletions can range in size from one base to thousands of bases or larger.

As used herein, "duplications" means when a specific sequence of DNA is copied and inserted behind or forward of the original copy one or more times or elsewhere in the genome.

As used herein, "heteroplasmy" is defined by the ratio of mutations in the mitochondrial sequences within one organ or cell. Heteroplasmic mutations are those mutations which occur in some, but not all of the copies of the mitochondrial genome.

As used herein, "homoplasmy" means all mitochondrial sequences are identical.

As used herein, "hyper-mutation" means accelerated mutation rate which cannot be explained by normal cellular processes or standard evolutionary principles.

As used herein, "inversions" refers to when a length of DNA is excised and reinserted in reverse orientation.

As used herein, "maternal inheritance" means mitochondria which are inherited through the cytoplasm of the ovum.

As used herein, "maternal line" refers to the clonal sequence of mitochondrial DNA as passed down through successive generations from the mother.

As used herein, "mitochondria" means a eukaryotic cytoplasmic organelle that generates ATP for cellular processes.

As used herein, "mutation" encompasses any modification or change in a DNA or RNA sequence from the wild type sequence, including without limitation point mutations, transitions, insertions, transversions, translocations, deletions, inversions, duplications, recombinations or combinations thereof. The modification or change of the sequence can extend from a single base change to the addition or elimination of an entire DNA or RNA fragment.

As used herein, "mutation load" refers to an increase in mutations in mtDNA which may eventually lead to compromised function of the involved gene or the entire genome or may accumulate in non-coding regions.

As used herein, "neoplasia" means a pathological process which may result in transformation to malignant status.

As used herein, "non-involved tissue" means tissue from a part of the body which is not associated with the disease in question.

As used herein, a "non-synonymous" mutation of a polynucleotide is a mutation which results in a different encoded amino acid.

As used herein, "normal tissue" means tissue with no visible manifestations of disease as determined by histology.

As defined herein, a "nucleic acid array" refers to a plurality of unique nucleic acids attached to one surface of a solid support at a density exceeding 20 different nucleic acids/cm$^2$ wherein each of the nucleic acids is attached to the surface of the solid support in a non-identical preselected region. In one embodiment, the nucleic acid attached to the surface of the solid support is DNA. In a preferred embodiment, the nucleic acid attached to the surface of the solid support is cDNA. In another preferred embodiment, the nucleic acid attached to the surface of the solid support is cDNA synthesized by polymerase chain reaction (PCR). Preferably, a nucleic acid array according to the invention, comprises nucleic acids of at least 150 nucleotides in length. Preferably, a nucleic acid array comprises nucleic acids of less than 6,000 nucleotides in length. More preferably, a nucleic acid array comprises nucleic acids of less than 500 nucleotides in length. In one embodiment, the array comprises at least 500 different nucleic acids attached to one surface of the solid support. In another embodiment, the array comprises at least 10 different nucleic acids attached to one surface of the solid support. In yet another embodiment, the array comprises at least 10,000 different nucleic acids attached to one surface of the solid support. The term "nucleic acid", as used herein, is interchangeable with the term "polynucleotide".

As used herein, a "nucleic acid target" or "a target nucleic acid" is defined as a nucleic acid capable of binding to a nucleic acid member of complementary sequence through one or more types of chemical bonds, usually through complementary base pairing, usually through hydrogen bond formation. As used herein, a nucleic acid target may include natural (i.e., A, G, C, or T) or modified bases (7-deazaguanosine, inosine, etc.). In addition, the bases in nucleic acid probe may be joined by a linkage other than a phosphodiester bond, so long as it does not interfere with hybridization. Thus, nucleic acid targets may be peptide nucleic acids in which the constituent bases are joined by peptide bonds rather than phosphodiester linkages. Preferably, the nucleic acid targets are derived from human tissue or fluid extracts. More preferably, the nucleic acid targets are single- or double-stranded DNA, RNA, or DNA-RNA hybrids synthesized from human tissue of fluid extracts.

As used herein, "nucleus" means the most conspicuous organelle in the eucaryotic cell, contains all of the chromasomal DNA.

As used herein, NPV (Negative Predictive Value) means the percent of patients with negative tests that do not have the disease or condition being tested for. It assesses the reliability of a negative test result. The calculation is NPV=(True negative)/(true and false negatives).

As used herein, "occasionally sun exposed skin" means skin that is occasionally or sometimes exposed in an individual. For example, depending on the individual, it may include shoulders, back and chest.

As used herein, PPV (Positive Predictive Value) means the percent of patients with positive test result having the disease or condition tested for. It assesses the reliability of a positive test result. The calculation is PPV=(True positive)/(True+False positives)

As used herein, "PSA Test" means prostate-specific antigen test; an antigen found in blood that may be indicative of cancer of the prostate.

As used herein, "point mutation" means the change of a single nucleotide in DNA.

As used herein, "polymorphism" means sequence variation in a population of alleles or mtDNA genomes.

As used herein, "precursor lesions" means a DNA mutation, or combinations thereof, indicating potential disease association.

As used herein, "predisposed to a disease" or a "predisposition to a disease" means that individuals are at higher risk for developing the disease or disorder or are at higher risk for early onset of the disease or disorder than the average individual, due to the presence or absence of mutations which are associated with the disease or disorder.

As used herein, "pre-neoplasia" means indications at the cellular or DNA level that a cell may be on the threshold of becoming neoplastic.

As used herein, "preselected region", "predefined region", or "unique position" refers to a localized area on a substrate which is, was, or is intended to be used for the deposit of a nucleic acid and is otherwise referred to herein in the alternative as a "selected region" or simply a "region." The preselected region may have any convenient shape, e.g., circular, rectangular, elliptical, wedge-shaped, etc. In some embodiments, a preselected region is smaller than about 1 $cm^2$, more preferably less than 1 $mm^2$, still more preferably less than 0.5 $mm^2$, and in some embodiments about 0.125 to 0.5 $mm^2$.

As used herein, the "presence" of a mutation in mtDNA includes heteroplasmic mutations and, therefore, it is contemplated that there may be additionally the presence of some normal mtDNA in a sample in which the mutated DNA is present.

As used herein, "rarely sun exposed skin" means skin that is rarely or hardly ever exposed in an individual. For example, depending on the individual, it may include buttocks and heel. This may also be called 'sun-protected' skin.

As used herein, "realtime PCR Cycle threshold $C_T$" is the point (cycle) at which the fluorescence crosses the threshold line.

As used herein, "somatic mutation" means a change in DNA sequence after fertilization.

As used herein, "solid substrate" or "solid support" refers to a material having a rigid or semi-rigid surface. The terms "substrate" and "support" are used interchangeable herein with the terms "solid substrate" and "solid support". The solid support may be biological, non-biological, organic, inorganic, or a combination of any of these, existing as particles, strands, precipitates, gels, sheets, tubing, spheres, containers, capillaries, pads, slices, films, plates, slides, etc. Often, the substrate is a silicon or glass surface, (poly)tetrafluoroethylene, (poly)vinylidendifluoride, polystyrene, polycarbonate, a charged membrane, such as nylon 66 or nitrocellulose, or combinations thereof. In a preferred embodiment, the solid support is glass. Preferably, at least one surface of the substrate will be substantially flat. Preferably, the surface of the solid support will contain reactive groups, including, but not limited to, carboxyl, amino, hydroxyl, thiol, or the like. In one embodiment, the surface is optically transparent.

As used herein, "sun exposed skin" means skin that is "usually" or "occasionally" exposed to the sun.

As used herein, "sun protected skin" means skin that is rarely exposed to the sun.

As used herein, "squamous cell carcinoma" means a type of cancer of skin cells.

As used herein, "stably associated" refers to a nucleic acid that is irreversibly bound to a solid substrate to form an array via covalent bonds, hydrogen bonds or ionic interactions such that the nucleic acid retains its unique preselected position relative to all other nucleic acids that are stably associated with an array, or to all other preselected regions on the solid substrate under conditions wherein an array is analyzed (i.e., hybridization and scanning).

A "statistically significant" number of mitochondrial DNA sequences is determined by or through the use of standard chi-square statistical algorithms using or determining observed versus expected scores.

As used herein, "subtle mutation" means low level of mutation at the threshold of detection.

As used herein, "symptomatic benign" means patients who exhibit one or more symptoms associated with prostate malignancy, including but not limited to elevated PSA, abnormal digital rectal examination (DRE) score, difficult urination, blood and/or pus in the urine, lower back, pelvic and upper thigh pain, or painful ejaculation, but have been diagnosed as benign by examination of biopsy tissue by a qualified pathologist.

As used herein, a "synonymous" mutation is a mutation in a polynucleotide which does not, have an affect on the encoded amino acid.

As used herein, "transitions" means substitution of like nitrogenous bases, pyrimidine to pyrimidine, purine to purine. A mutation in which one pyrimidine is substituted by the other, or in which one purine is substituted by the other.

As used herein, "transversions" means substitution of unlike nitrogenous bases, purine to pyrimidine, pyrimidine to purine. A mutation in which a purine is substituted or replaced by a pyrimidine or vice versa.

As used herein, "usually sun exposed skin" means skin that is usually or often exposed in an individual. For example, depending on the individual, it may include scalp, face, neck and ears.

MtDNA and Diagnosis of Specific Diseases

In an embodiment of the present invention, methods are provided for monitoring aging, sun exposure, and diagnosing specific diseases such as prostate cancer and non-melanoma skin cancer through comparisons of mtDNA sequences. Diagnosing diseases such as prostate cancer with mtDNA, rather than nuclear DNA has several advantages. Firstly, mtDNA, a less complex genome, is easily understood at an individual and population level, hence a large mtDNA database with normal and disease associated genomes renders individual diagnosis extremely accurate. Accordingly, variation, in relationship to disease, is understood. Secondly, mtDNA has a 10-fold higher mutation rate than nuclear DNA (Wallace 1992). Nuclear rearrangements, suggestive of preliminary disease, are rapidly communicated to mitochondria, where they appear as somatic mutations. Thirdly, mtDNA has a maternal inheritance pattern, and is essentially clonal in that all mitochondria begin with the same mtDNA sequence, hence variation from this clonal condition is easily detected. Additionally, mtDNA does not show convincing evidence of recombination, thus any alterations in sequence are a somatic event. Any one mitochondrion harboring a mutation(s) is in a sense 'recessive' as a consequence of there being many mitochondrial genomes (2-10 copies) per mitochondrion, and many mitochondria per cell (500-2,000). Moreover, mitochondrial genomes can tolerate very high levels (up to 90%) of mitochondria with damaged genomes. This happens through complementation by the remaining wild type mtDNA (Chomyn et al. 1992). However, mutated genomes have a replicative advantage over wild type genomes because they are usually smaller (Hayashi et al. 1991), hence there is clonal expansion of mutated mtDNA (Brierley et al. 1998), suggesting that unlike nuclear genes, there is little or no selection against cells harboring mtDNA mutations. Because of this elevated mutation rate, mutations and/or deletions that appear in mtDNA are maintained through the life span of the cell and may serve as a record of exposures to various mutagens. The integrity of mtDNA is maintained by nuclear repair mechanisms, and a defect at these loci has been suggested to result in an autosomal dominant disorder associated with multiple mitochondrial deletions (Zeviani et al. 1990). Consequently, mtDNA may function as an early warning sentinel of early nuclear events related to a variety of cancers or other diseases. Finally, the mitochondrial genome can be sequenced and monitored for mutations on an individual basis.

The methods and products of the present invention detect both heteroplasmic as well as homoplasmic mutations. In fact, heteroplasmic mutations may be key to the detection of the early genesis of disease, disorder or aging. In addition, although specific mutation sites may indicate a particular disease state, disorder or aging process, the total mutation load is also important in determining the genesis, presence and progression of a disease, a disorder or aging.

The present invention allows for the ability to examine benign or normal tissue or bodily fluids to determine the effects of sun exposure, the genesis and/or presence of disease, disorder or aging. For example, the present invention allows for the ability to examine benign tissue or bodily fluids for the presence of pre-neoplasia, neoplasia, progression toward malignancy and malignancy.

The mitochondrial mutations detected by the methods of the invention are compared to inter and intrapopulation variations in mitochondrial DNA, and may include comparison with mitochondrial DNA from non-involved tissue from the subject, or with mitochondrial DNA from a maternal relative. It is not necessary to analyze the entire mitochondrial genome. For example, it is not necessary to sequence the entire mitochondrial genome, only a select portion of it. Accordingly, a sample of mitochondrial DNA can provide a diagnosis.

Detection of Sun Exposure

In one embodiment of the invention, a system for early detection of mitochondrial DNA mutations and rearrangements, for example deletions, as a result of sun exposure is provided. The particular changes, such as the common deletion, the 3895 bp deletion identified in examples 13 and 14, associated mutations, and the incidence of as yet uncharacterised deletions in mtDNA serve as reliable bio-markers of sun exposure.

Diagnosis of Skin Cancer

In a preferred embodiment of the invention, a system for early diagnosis of mtDNA changes in non-melanoma skin cancer (NMSC) and melanoma skin cancer, and their precursor lesions indicative of solid tumour development is provided. The particular changes, such as the common deletion, the 3895 bp deletion identified in examples 13 and 14, associated mutations, and the incidence of as yet uncharacterised deletions in mtDNA serve as reliable bio-markers of sun exposure, and associated skin cancer. Non-melanoma skin cancer in particular is associated with chronic life long sun exposure. Melanoma skin cancer seems to be more related to acute burning episodes. The mutation fingerprint of the entire mtDNA genome in human NMSC and its precursor lesions is determined. Thus mtDNA changes are established as an early bio-marker of human skin cancer and its precursor lesions. Denaturing HPLC can then be used to assess low levels of heteroplasmy at the sequences of interest. This approach can also provide an insight into the development of early changes in other human tumours.

Diagnosis of Prostate Cancer

In another embodiment of the invention, a system for diagnosis of prostate cancer is provided. Age related accumulation of mtDNA defects might predispose an individual to the appearance of certain clinical disorders such as prostate cancer which is prevalent in middle age and older men. In a preferred embodiment, routine prostate cancer screening takes place through mitochondrial genome sequencing from prostate massage fluid. The presence of epithelial cells transformed into cancer cells, can be determined through amplification of mtDNA from prostate massage fluid, eclipsing current diagnostic techniques such as digital rectal examination and PSA. Recently Fliss et al. (2000) identified mutated mtDNA in urine samples of patients with bladder cancer. Similar findings in prostate massage fluid provide a non-invasive early detection method for prostate cancer. Different types of prostate cancer can be diagnosed, as well as differentiating between aggressive, fast growing cells in patients in contrast to prostate cancer as a whole. For example, the 3.4 kb deletion identified in the applicant's teachings, can be used as an indication of prostate cancer.

Early Detection and Monitoring of Prostate Cancer Progression

The system and method of the present invention may be used to detect cancer, and in particular prostate cancer, at an early stage, and before any histological abnormalities. For example, the system and method of the present invention may be used to detect pre-neoplasia in prostate tissue. The system can be used to detect the genesis and progression of prostate cancer. Mutations, including both subtle and hyper-mutation (Chen et al. 2002; Chen et al. 2003) in mitochondrial DNA from human prostate tissue, or fluid associated with the prostate (for example prostate massage fluid or urine), can be tested for the presence of neoplasia, and retested at intervals to follow cancer transformation, diagnose malignancy, or confirm continued benign status.

These mutations may be determined by comparison to mitochondria extracted from non-involved tissue such as, but not limited to: blood, urine, hair and buccal swabs. This direct comparison eliminates polymorphisms, maternal background or normal haplotype variation unassociated with disease. The mutations can also be compared to mitochondrial sequences associated with inter and intrapopulation variations. One or more mutations from fluid or tissue of the organ or body system in question, indicates possible disease genesis. The person is then monitored, at successive intervals, for an increase in mutations at other sites, and/or an increase in the number of mutated mitochondrial genomes, indicating disease progression. Benign tissue from the prostate cannot always be considered non-involved. In fact, as can be seen in Example 9, below, what appears to be benign tissue may contain mitochondrial mutations associated with pre-neoplasia, neoplasia, progression toward malignancy or malignancy. In addition, mutation load rather than specific mutations may be instrumental in determining disease and progression of disease. The system and method of the present invention detects heteroplasmic as well as homoplasmic mutations.

The prostate gland is monitored for mutations in the mitochondrial genome through prostate massage fluid (PMF) taken during an initial digital rectal examination (DRE) of the prostate. Cells within the PMF are concentrated, smeared on a slide and stained with PSA immunoperoxidase for identification of prostate epithelial cells. These prostate cells are selectively recovered through laser capture micro-dissection. The mitochondrial DNA from these cells is analyzed and compared to mitochondrial DNA from non-involved tissue, and/or to sequences of inter and intrapopulation variations. For example, the DNA analysis can comprise sequencing of the mtDNA. Total DNA is extracted from these cells and mitochondrial specific primers, designed for use with biopsy material treated with formalin (Table 5), are used to amplify the entire mtDNA genome with overlapping amplicons. These PCR products are then sequenced by methods well known to those in the art, including DNA resequencing arrays. Sequencing results are screened for heteroplasmies and mutations and compared to a database of known mtDNA mutations associated with malignant and benign prostate tissues. Based on these comparisons a designation is returned as to the condition of the prostate in regards to, but not limited to: benign (no mutations); pre-neoplasia or neoplasia (low level of mutations); or malignancy (high level of mutations). In the situation of benign, pre-neoplasia and neoplasia, the prostate can be monitored for progression through regular PMF screenings as described.

Alternatively, biopsy material which has been diagnosed as benign, atypical, abnormal can undergo similar testing by either laser capture micro-dissection of the biopsy, or the tissue can be scraped off the slides, or mounted tissue sections can be used, followed by DNA extraction, amplification, sequence analysis and database comparison.

As an alternative to sequencing, and comparison to a database, micro-array technology could be used to identify a specific pattern of mutations, or mutation load based on any number, or combination of the mutations listed in Table 4, through the construction of oligonucleotides, or a specific set of oligonucleotides.

Disease progression can be monitored by comparing mtDNA mutations at successive intervals to a database of mutations in mitochondrial genomes associated with pre-neoplasia, neoplasia and prostate cancer, including calculation of total mutation load. Prostate biopsy tissue can be tested for pre-neoplasia, neoplasia and/or malignant progression in cells described clinically as benign, normal, atypical or abnormal by common histological/pathological, or other clinical methods.

Similarly, the DNA may be analyzed for specific deletions that are known to be associated with disease, for example prostate cancer. This can be done by using PCR based technologies to screen for such deletions.

Assessment of Mutations Associated with Aging

The system and method of the present invention may be used to assess aging, based on the increasing frequency of mutations such as the "common deletion" of 4977-bp and other mutations of the mitochondrial genome (Liu et al. 1997). This information, in conjunction with health survey data, allows crucial statistical discrimination between separate causes resulting in the same mutation/deletion. Fortunately mtDNA is inherited exclusively through the ovum and is essentially clonal in nature (Van De Graaff & Fox, 1995). This permits carefully controlled studies of mutations/deletions within maternal lines through several generations to determine a reliable age related deletion frequency. This information may be used to develop treatment methods which slow the aging process.

Collection of Samples

Biological samples can be collected by any known means, whether for the purpose of constructing a mtDNA sequence database, or performing a diagnostic test on an individual. Samples destined for database generation include, but are not limited to: tumour banks, maternal lineage studies involving affected and unaffected individuals from the same maternal lineage, as well as maternal lineage studies from groups or populations with high frequencies of specific disease such as, but not limited to: skin and prostate cancer, assessment of health status and aging. For example, FTA® Gene Cards® may be used to collect and archive biological samples. Suitable samples include any tissue or body fluid derived from mesothelium, epithelium, or endothelium. Such tissues and fluids include, but are not limited to blood, sputum, buccal cells, saliva, prostate massage fluid, sweat, bone, hair, lymph tissue, cervical smears, breast aspirate, fecal matter, ejaculate, menstrual flow, urine and biopsy tissue. Preferably, approximately 100 µl of blood, 100 µg to 25 mg of solid tissue is sampled. In the case of suspected skin cancer, skin cells or tissue, (from normal, NMSC and precursor lesions) is taken from skin biopsy or a routine suction blistering technique. Where a disease is suspected, primary care physicians, oncologists or other practitioners, may extract both normal and suspected disease tissue from the patient. For the purpose of analyzing sun exposure, tissue may be taken from the dermis or epidermis, or a combination of both.

For samples of tumours such as prostate or skin, replicate cross-sections (5 microns) of micro-dissected paraffin embedded tissues are de-paraffinized prior to one slide being stained with hematoxylin and eosin (HE), with the replicate stained with methyl green (MG), as is standard in the art. HE stains are graded by a pathologist for normal, precursor, and applicable grades of tumour progression. Replicate MG slides are used for laser capture, according to manufacturers recommendations (Arcturus) of graded cells.

Extraction of mtDNA

Extraction of DNA may take place using any method known in the art, followed by amplification of all or a region of the mitochondrial genome, and may include sequencing of the mitochondrial genome, as described in Current Protocols in Molecular Biology.

Analyzing mtDNA

The step of detecting the presence of mutations in the mtDNA can be selected from any technique as is known to those skilled in the art. For example, analyzing mtDNA can comprise sequencing the mtDNA, amplifying mtDNA by PCR, Southern, Northern, Western South-Western blot hybridizations, denaturing HPLC, hybridization to microarrays, biochips or gene chips, molecular marker analysis, biosensors, melting temperature profiling or a combination of any of the above. In addition, statistical techniques such as Inductive Rule Extraction, and Neural Networking can be used.

Sequencing of MtDNA

PCR

Polynucleotide sequences of the invention can be amplified by the polymerase chain reaction (PCR). PCR methods are well-known to those skilled in the art. PCR requires the presence of a nucleic acid to be amplified, two single stranded oligonucleotide primers flanking the sequence to be amplified, a DNA polymerase, deoxyribonucleoside triphosphates, a buffer and salts. The method of PCR is well known in the art. PCR is performed as described in Mullis and Faloona, 1987, *Methods Enzymol.*, 155: 335, herein incorporated by reference.

In general, PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of 10×PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 μl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 40° C. and 72° C. is used. In general, initial denaturation of the template molecules normally occurs at between 92° C. and 99° C. for 4 minutes, followed by 20-40 cycles consisting of denaturation (94-99° C. for 15 seconds to 1 minute/kb), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

DNA Sequencing

Any known means to sequence the mitochondrial genome may be used. Preferably, mtDNA is amplified by PCR prior to sequencing. PCR products can be sequenced directly or cloned into a vector which is then placed into a bacterial host. Examples of DNA sequencing methods are found in Brumley, R. L. Jr. and Smith, L. M., 1991, Rapid DNA sequencing by horizontal ultrathin gel electrophoresis, Nucleic Acids Res. 19:4121-4126 and Luckey, J. A., et al, 1993, High speed DNA sequencing by capillary gel electrophoresis, Methods Enzymol. 218: 154-172. The combined use of PCR and sequencing of mtDNA is described in Hopgood, R., et al, 1992, Strategies for automated sequencing of human mtDNA directly from PCR products, Biotechniques 13:82-92 and Tanaka, M. et al, 1996, Automated sequencing of mtDNA, Methods Enzymol. 264: 407-421

Deletion Analysis and Detection

A preferable approach is the long extension PCR (LX-PCR) technique using the Expand Long Template PCR system (Boehringer Mannheim). Using the LX-PCR technique, which has been established and validated in the Birch-Machin laboratory (Ray et al. 2000), there is the opportunity to rapidly screen for the whole spectrum of mtDNA deletions as opposed to the incidence of a single deletion.

A semi-quantitative PCR method (Corral-Debrinski et al 1991) can be used to estimate the proportion of the mtDNA$^{4977}$ deletion in the total mtDNA.

In addition, Southern Blot and probing technology labeled with isotopes or any other technique as is standard in the art may be used for deletion detection as well.

Quantitative PCR can be used to quantify the amount of any specific deletion target using a primer that bridges the newly formed sequence junction. The quantity of deleted mtDNA molecules may be compared with the quantity of wild-type mt DNA to determine the proportion of deleted mtDNA molecules.

Sequencing of PCR Products

Any known means may be used to sequence the PCR products. Preferably, the entire DNA sequence is characterized by di-deoxy sequencing using ABI Big Dye Terminator™ technology and a series of 72 overlapping primers each for heavy and light strands. Sequencing occurs on one, several, or a combination of ABI platforms such as the 310, 3100, or 3700. Sequencing reactions are performed according to manufacturer's recommendation.

Mutational Analysis of the Mitochondrial Genome Using Denaturing High Performance Liquid Chromatography (DHPLC)

Prior to sequencing of the mitochondrial genome and identification of mutational hotspots, DHPLC can be used to rapidly screen for mutations in many samples. This technique provides greater sensitivity in identification of low levels of heteroplasmy. It cannot detect homoplasmic changes but will complement traditional sequencing. Apart from the homoplasmic mutations recently identified in tumours, the vast majority of reported mtDNA mutations are heteroplasmic (Chinnery et al. 1999). These heteroplasmic mtDNA changes result in the formation of heteroduplexes after PCR amplification of the mtDNA. Rapid screening for heteroplasmic mtDNA mutations is determined using the relatively new technique of denaturing high performance liquid chromatography (DHPLC) (Oefner & Underhill, 1998). This technique has recently been used to rapidly screen and identify whole mtDNA genomes for heteroplasmic point mutations down to levels <5% (Van den Bosch et al. 2000).

The DHPLC may be performed on the WAVE™ DNA Fragment Analysis System (Transgenomic, Omaha, USA) which provides a fully automated screening procedure. The same technology can be used to screen for mtDNA heteroplasmic mutations. Preferably, the entire mtDNA genome is amplified by PCR in 13 overlapping fragments using two different PCR conditions as described by van den Bosch et al. (2000). The 1-2 kb PCR products are digested into fragments of 90-600 bp and resolved at their optimal melting temperature. Mutations are represented as two peaks and mutations with low percentages, such as <2% heteroplasmy as a 'shoulder' in the peak.

DNA sequencing can also take place using a microarray, as is known in the art (Chee et al. 1996).

Data Analysis

Once sequenced, normal and disease associated mtDNA sequences are archived for comparison in a database. Resequencing devices, micro-array technology, integrated microfluidic amplification and analysis systems, high-speed, high-throughput, mutation detection, and other methods may all be used with the methods of the present invention.

Data obtained from the sequencing of the individual mitochondrial genome is compared to population level data. The data is obtained through obtaining samples and sequencing mtDNA as described above. Preferably, the database contains information from maternal line studies. The population level data is maintained in a database. Any suitable database can be used.

Preferably, a multidimensional evaluation research database of clinical and biological data is used, which provides the bio-informatics infrastructure necessary for the collection, processing and dissemination of information amassed by the laboratories involved in this venture. The database is a centralized electronic system which links networks resulting in a dynamic and powerful resource.

The database may be accessed through any known means, and preferably through a secure Internet pathway. Preferably, the database is developed using an e-commerce algorithm, built on a server and deployed using an application server which supports a high volume of concurrent users through optimized performance and scalability features. A separate "web" server can provide the foundation of the web-site architecture since it can serve as the central point through which all content, applications, and transactions must flow before reaching users.

Data mining algorithms known in the art are used to discover patterns, clusters and models from data (SAS 2000).

Moreover, intelligent algorithms and methods will be developed for: occurrence of mutation and mutation rates, patterns of mutations for disease detection, information retrieval, and other complex sequence analysis software.

Nucleic Acid Members and Probes

The invention provides for nucleic acid members and probes that bind specifically to a target nucleic acid sequence. The target nucleic acid sequence is a nucleic acid or a region of a nucleic acid that is to be detected, as indicative of disease such as prostate cancer, non-melanoma skin cancer and the like. The target nucleic acid sequences to be analyzed using a microarray of the invention are preferably derived from human tissue or fluid samples. The invention provides for target nucleic acid sequences comprising RNA or nucleic acid corresponding to RNA, (i.e., cDNA), or DNA. Nucleic acid members are stably associated with a solid support to comprise an array according to the invention. The nucleic acid members may be single or double stranded, and may be a PCR fragment amplified from cDNA.

The invention also provides for polynucleotide sequences comprising a probe. As used herein, the term "probe" refers to an oligonucleotide which forms a duplex structure with a sequence in the target nucleic acid, due to complementarity of at least one sequence in the probe with a sequence in the target region. The probe may be labeled, according to methods known in the art. A probe according to the invention may be single or double stranded.

Diagnostic Devices

The invention includes diagnostic devices such as biochips, gene chips or microarrays used to diagnose specific diseases or identify specific mutations. All sequenced mitochondrial genomes are assessed to create a consensus structure of the base pair arrangement and are assigned a prohibiting index for proportion of base pair deletions and mutations associated with a particular disease or disorder. The diagnostic arrangement is then used to create biochips, gene chips, or microarrays.

Once sequences associated with particular diseases, disease states or disorders are identified, hybridization of mtDNA to an array of oligonucleotides can be used to identify particular mutations. Any known method of hybridization may be used. Preferably, an array is used, which has oligonucleotide probes matching the wild type or mutated region, and a control probe. Commercially available arrays such as microarrays or gene chips are suitable. These arrays contain thousands of matched and control pairs of probes on a slide or microchip, and are capable of sequencing the entire genome very quickly. Review articles describing the use of microarrays in genome and DNA sequence analysis is available at www.gene-chips.com.

Microarray

Polynucleotide arrays provide a high throughput technique that can assay a large number of polynucleotides in a sample comprising one or more target nucleic acid sequences. The arrays of the invention are useful for gene expression analysis, diagnosis of disease and prognosis of disease (e.g., monitoring a patient's response to therapy, drug screening, and the like).

Any combination of the polynucleotide sequences of mtDNA indicative of disease, aging, or other health related mutations are used for the construction of a microarray.

The target nucleic acid samples to be analyzed using a microarray are derived from any human tissue or fluid which contains adequate amounts of mtDNA, as previously described, preferably prostate massage fluid, solid tumours, benign tissue, blood, or urine. The target nucleic acid samples are contacted with polynucleotide members under hybridization conditions sufficient to produce a hybridization pattern of complementary nucleic acid members/target complexes.

Construction of a Microarray

The microarray comprises a plurality of unique polynucleotides attached to one surface of a solid support, wherein each of the polynucleotides is attached to the surface of the solid support in a non-identical preselected region. Each associated sample on the array comprises a polynucleotide composition, of known identity, usually of known sequence, as described in greater detail below. Any conceivable substrate may be employed in the invention.

The array is constructed using any known means. The nucleic acid members may be produced using established techniques such as polymerase chain reaction (PCR) and reverse transcription (RT). These methods are similar to those currently known in the art (see e.g. PCR Strategies, Michael A. Innis (Editor), et al. (1995) and PCR: Introduction to Biotechniques Series, C. R. Newton, A. Graham (1997)). Amplified polynucleotides are purified by methods well known in the art (e.g., column purification). A polynucleotide is considered pure when it has been isolated so as to be substantially free of primers and incomplete products produced during the synthesis of the desired polynucleotide. Preferably, a purified polynucleotide will also be substantially free of contaminants which may hinder or otherwise mask the binding activity of the molecule.

In the arrays of the invention, the polynucleotide compositions are stably associated with the surface of a solid support, wherein the support may be a flexible or rigid solid support.

Any solid support to which a nucleic acid member may be attached may be used in the invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Due to their flat surface, probe and hybridization reagents are minimized using glass slides. Slides also enable the targeted application of reagents, are easy to keep at a constant temperature, are easy to wash and facilitate the direct visualization of RNA and/or DNA immobilized on the solid support. Removal of RNA and/or DNA immobilized on the solid support is also facilitated using slides.

The particular material selected as the solid support is not essential to the invention, as long as it provides the described function. Normally, those who make or use the invention will select the best commercially available material based upon the economics of cost and availability, the expected application requirements of the final product, and the demands of the overall manufacturing process.

Numerous methods are used for attachment of the nucleic acid members of the invention to the substrate (a process referred as spotting). For example, polynucleotides are attached using the techniques of, for example U.S. Pat. No. 5,807,522, which is incorporated herein by reference for teaching methods of polymer attachment. Alternatively, spotting is carried out using contact printing technology.

The amount of polynucleotide present in each composition will be sufficient to provide for adequate hybridization and detection of target polynucleotide sequences during the assay in which the array is employed. Generally, the amount of each nucleic acid member stably associated with the solid support of the array is at least about 0.1 ng, preferably at least about 0.5 ng and more preferably at least about 1 ng, where the amount may be as high as 1000 ng or higher, but will usually not exceed about 20 ng. Where the nucleic acid member is "spotted" onto the solid support in a spot comprising an overall circular dimension, the diameter of the "spot" will generally range from about 10 to 5,000 µm, usually from about 20 to 2,000 µm and more usually from about 50 to 1000 µm.

Control polynucleotides may be spotted on the array and used as target expression control polynucleotides and mismatch control nucleotides to monitor non-specific binding or cross-hybridization to a polynucleotide in the sample other than the target to which the probe is directed. Mismatch probes thus indicate whether a hybridization is specific or not. For example, if the target is present the perfectly matched probes should be consistently brighter than the mismatched probes. In addition, if all central mismatches are present, the mismatch probes are used to detect a mutation.

Target Preparation

The targets for the microarrays, are derived from human fluid or tissue samples. It may be desirable to amplify the target nucleic acid sample prior to hybridization. One of skill in the art will appreciate that whatever amplification method is used, if a quantitative result is desired, care must be taken to use a method that maintains or controls for the relative frequencies of the amplified polynucleotides. Methods of "quantitative" amplification are well known to those of skill in the art. For example, quantitative PCR involves simultaneously co-amplifying a known quantity of a control sequence using the sane primers. This provides an internal standard that may be used to calibrate the PCR reaction. The high density array may then include probes specific to the internal standard for quantification of the amplified polynucleotide. Detailed protocols for quantitative PCR are provided in PCR Protocols, A Guide to Methods and Applications, Innis et al., Academic Press, Inc. N.Y., (1990). Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

The invention provides for labeled target or labeled probe. Any analytically detectable marker that is attached to or incorporated into a molecule may be used in the invention. An analytically detectable marker refers to any molecule, moiety or atom which is analytically detected and quantified. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, 35S, $^{14}$C, or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. However, in a preferred embodiment, the label is simultaneously incorporated during the amplification step in the preparation of the sample polynucleotides. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed polynucleotides. Alternatively, a label may be added directly to the original polynucleotide sample (e.g., mRNA, polyA mRNA, cDNA, etc.) or to the amplification product after the amplification is completed. Means of attaching labels to polynucleotides are well known to those of skill in the art and include, for example nick translation or end-labeling (e.g. with a labeled RNA) by kinasing of the polynucleotide and subsequent attachment (ligation) of a polynucleotide linker joining the sample polynucleotide to a label (e.g., a fluorophore).

In a preferred embodiment, the target will include one or more control molecules which hybridize to control probes on the microarray to normalize signals generated from the microarray. Labeled normalization targets are polynucleotide sequences that are perfectly complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays.

Hybridization Conditions

Polynucleotide hybridization involves providing a denatured probe or target nucleic acid member and target polynucleotide under conditions where the probe or target nucleic acid member and its complementary target can form stable hybrid duplexes through complementary base pairing. The polynucleotides that do not form hybrid duplexes are then washed away leaving the hybridized polynucleotides to be detected, typically through detection of an attached detectable label. It is generally recognized that polynucleotides are denatured by increasing the temperature or decreasing the salt concentration of the buffer containing the polynucleotides. Under low stringency conditions (e.g., low temperature and/or high salt) hybrid duplexes (e.g., DNA:DNA, RNA:RNA, RNA:DNA, cDNA:RNA and cDNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. Methods of optimizing hybridization conditions are well known to those of skill in the art (see, e.g., Laboratory Techniques in Biochemistry and Molecular Biology, Vol. 24: Hybridization With Polynucleotide Probes, P. Tijssen, ed. Elsevier, N.Y., (1993)).

Following hybridization, non-hybridized labeled or unlabeled polynucleotide is removed from the support surface, conveniently by washing, thereby generating a pattern of hybridized target polynucleotide on the substrate surface. A variety of wash solutions are known to those of skill in the art and may be used. The resultant hybridization patterns of labeled, hybridized oligonucleotides and/or polynucleotides may be visualized or detected in a variety of ways, with the particular manner of detection being chosen based on the particular label of the test polynucleotide, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled target polynucleotides to obtain a count or absolute value of the copy number of each end-labeled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test polynucleotides from the remaining data. The resulting data is displayed as an image with the intensity in each region varying according to the binding affinity between associated oligonucleotides and/or polynucleotides and the test polynucleotides.

Following detection or visualization, the hybridization pattern is used to determine quantitative information about the genetic profile of the labeled target polynucleotide sample that was contacted with the array to generate the hybridization pattern, as well as the physiological source from which the labeled target polynucleotide sample was derived. By genetic profile is meant information regarding the types of polynucleotides present in the sample, e.g. in terms of the types of genes to which they are complementary, as well as the copy number of each particular polynucleotide in the sample.

Diagnostic or Prognostic Tests

The invention provides for diagnostic tests for detecting diseases. The invention also provides for prognostic tests for monitoring a patient's response to therapy. According to the method of the invention, the presence of disease or the patient's response to therapy is detected by obtaining a fluid or tissue sample from a patient. A sample comprising nucleic acid is prepared from the fluid or tissue sample. The nucleic acid extracted from the sample is hybridized to an array comprising a solid substrate and a plurality of nucleic acid members, wherein each member is indicative of the presence of disease or a predisposition to a disease or disorder. According to this diagnostic test, hybridization of the sample comprising nucleic acid to one or more nucleic acid members on the array is indicative of disease, a predisposition to a disease or disorder, or in the case of a prognostic test, indicative of a patient's response to therapy.

Kits

Kits containing reagents and instructions to carry out the methods of the present invention are provided. For example, the kit may comprise reagents and instructions for detecting mitochondrial deletions, mutations, heteroplasmies, homoplasmies in tissue specific samples and tissue associated fluids. The kits may also comprise one or more primers which hybridize to the mitochondrial genome for making a primer extension product. Kits may also include a solid support such as a disposable chip, means for holding the solid support, means for extraction of mtDNA and means for access to a database of mtDNA sequences.

For example, a kit to detect a mtDNA deletion associated with prostate cancer may include the forward and reverse 3.4 primers, reagents, and instructions.

Similarly, a kit to detect a mtDNA deletion associated with sun exposure or NMSC may include L404 primer, H4676 primer, the 3895 probe, reagents and instructions.

Other utilities for the present invention, such as that described above and in the following examples, will be readily apparent to those skilled in the art.

The present invention is more particularly described in the following examples which are intended as illustrative only since numerous modifications and variations will be apparent to those skilled in the art.

Example 1

Prostate Tumours

Following acquisition of prostate fluid or surgery to remove prostate tumours, biopsy slides are prepared to identify transforming or cancerous cells. Laser Capture Microdissection (LCM) microscopy is used to isolate cells that are either normal, benign, or malignant from the tissue section. Procurement of diseased cells of interest, such as precancerous cells or invading groups of cancer cells is possible from among the surrounding heterogeneous cells.

Total DNA extraction from each of these cells was purified according to a modification of the protocol outlined by Arcturus Engineering Inc. DNA was extracted from cells with a 50 µl volume of 1 mg/ml proteinase K (PK), in 10 mM Tris pH 8.0, 0.1 mM EDTA pH 8.0, and 0.1% Tween 20, at 42° C. overnight. Following incubation overnight at 42° C. the tubes were removed from the incubation oven. The samples were microcentrifuged for 5 min at 640O rpm (2000×g). The CapSure™ was removed from the tube and discarded. The tube was incubated at 95° C. for 10 minutes (PK is inactivated) and then cooled to room temperature. 5-50 µl of the sample was used for PCR amplification.

Following purification, individual samples are amplified, by LX-PCR using the appropriate primers for hypervariable region 1 (HV1), hypervariable region 2 (HV2) and the entire 12S region. These PCR products are then sequenced using high throughput methods as is well known in the art.

Alternatively, full length mitochondrial genomes may be amplified using the primers in Table 5. Specific capture and amplification of DNA derived from malignant tumour cells of any Geason Grade, cells from an adjacent benign gland and cells from a "distant" benign gland may be amplified. Other prostate tissues which could and are amplified includes: prostatic intraepithelial neoplasia (PIN), benign prostatic hyperplasia (BPH), hyperplasia of various types, stroma, and cells with undetermined changes. This work was done on prostate tissues from 31 individuals electing to have a prostatectomy because of a prostate cancer diagnosis. Three tissue types were captured: malignant, adjacent benign and distant benign from each individual. Blood from each patient was used as a positive, non-diseased tissue control. Amplification and sequencing of these samples resulted in the novel mutations seen in Table 4. The mutations of Table 4 are also provided in SEQ ID No: 102 which lists the substitutions, SEQ ID NOs: 103 to 109 which lists the deletions, and SEQ ID No: 110 to 138 which lists the insertions. Polymorphisms and mutation positions were determined by comparison to the Revised Cambridge Reference Sequence (2001), however the historical numbering has been maintained such that the deletion at position 3106 is denoted as a gap and the rare polymorphism 750A has been retained. A subset of this data (7 protein coding regions) was then subjected to principal component analysis, as is standard in the art, with the following results as shown in Table 1a:

TABLE 1a

| Blood | distant benign | adjacent benign | malignant | Unknown |
|---|---|---|---|---|
| 100.00% | 0.00% | 0.00% | 0.00% | 0.00% |
| 16.13% | 35.48% | 9.68% | 29.03% | 16.13% |
| 12.9% | 12.90% | 45.16% | 3.22% | 25.81% |
| 3.22% | 0.00% | 0.00% | 96.78% | 0.00% |

The results demonstrate a clear pattern of malignant transformation. Normal tissue (blood) and malignant tissue display high clustering frequencies (1.00 and 0.967). Interestingly, adjacent and distant benign, both of which appear normal in a histological and pathological sense, show levels of transformation with over 50% of the samples falling outside the distant benign and adjacent benign intercepts. Moreover, the same data was analyzed by a neural network, as is standard in the art, with the following results as shown in Table 1b:

TABLE 1b

| Blood | distant benign | adjacent benign | Malignant |
|---|---|---|---|
| 100.00% | 0.00% | 0.00% | 0.00% |
| 6.45% | 0.00% | 0.00% | 93.55% |
| 19.35% | 0.00% | 0.00% | 77.14% |
| 3.22% | 0.00% | 0.00% | 96.78% |

This table shows that, in the presence of tumour, all prostate tissue is considered malignant at the molecular level, even though anatomical appearance of the tissue may be "normal."

TABLE 1c

MUTATION REGIONS - ND1, ND2, COX1 and CYTB

| | distant benign | adjacent benign | malignant |
|---|---|---|---|
| 1. | 105DB - 6037 | 105AB - 4655 | 105ML - 4655, 4917, 7407 |
| 2. | 208DB | 208AB - 4917, 5174, 5985, 6776 | 208ML - 4722, 6553, 7028 |
| 3. | 349DB | 349AB | 349ML - 6548 |
| 4. | 377DB - 4735, 5984, 6912 | 377AB | 377ML - 4917, 6686, 7028, 7407, 15452, 15607 |
| 5. | 378DB | 378AB - 6776, 15043 | 378ML - 4703 |
| 6. | 380DB - 3469, 3507, 15218, | 380AB - 4917, 4951, 5440, 6059 | 380ML - 15218 |
| 7. | 382DB - 6307, 7028, 7407, 15452, 15527, 15607 | 382AB - 4716, 5312, 5371, 15162, 15323, 15324 | 382ML - 6147, 6691, 7178, 15523 |
| 8. | 384DB - 4733, 7028 | 384AB - 6219, 15452, 15607 | 384ML - 4733, 7028 |
| 9. | 386DB - 15677 | 386AB - 15244, 15301, 15452, 15607, 15670 | 386ML |
| 10. | 416DB - 4561, 15326, 15525 | 416AB | 416ML - 4864 |
| 11. | 417DB | 417AB | 417ML - 4917 |
| 12. | 418DB | 418AB - 7159 | 418ML - 7028, 7407 |
| 13. | 426DB | 426AB | 426ML - 4892, 5102, 5213 |
| 14. | 449DB - 4646, 4917, 5999, 6047, 7407 | 449AB | 449ML |
| 15. | 450DB - 15323 | 450AB - 4917, 5300, 15323 | 450ML - 3398, 5147, 6009, 15323 |
| 16. | 451DB | 451AB - 4217 | 451ML |
| 17. | 452DB - 4018, 6557, 15286 | 452AB - 3308, 3480, 3594, 3666, 3693, 5036, 5046, 5393, 5984, 6548, 6827, 6989, 7055, 7146, 7256, 7389, 15115 | 452ML - 3480, 4591, 5268, 7159, 7407 |
| 18. | 455DB - 7160 | 455AB | 455ML |
| 19. | 456DB - 3589, 4216, 5312, | 456AB - 4216, 4787, 4917, | 456ML - 4787, 6579, 7059, |

TABLE 1c-continued

MUTATION REGIONS - ND1, ND2, COX1 and CYTB

| | distant benign | adjacent benign | malignant |
|---|---|---|---|
| | 5424, 6041, 7013, 7407, 15384, 15452 | 7407, 15343, 15452, 15607 | 15302 |
| 20. | 457DB | 457AB | 457ML |
| 21. | 458DB - 5198, 7407 | 458AB | 458ML |
| 22. | 460DB - 5147 | 460AB | 460ML |
| 23. | 461DB - 7028, 7184 | 461AB - 3394, 7184, 14899 | 461ML - 7184 |
| 24. | 463DB - 14903 | 463AB - 14903 | 463ML - 14903 |
| 25. | 464DB | 464AB | 464ML - 6314, 6643, 6667, 7028, 7066, 7407, 15265 |
| 26. | 466DB - 3507, 7028 | 466AB - 3908, 3969, 3992, 4017, 4185, 4239, 7028 | 466ML - 6382, 6776, 15527 |
| 27. | 467DB | 467AB - 4917, 5147 | 467ML |
| 28. | 498DB - 14903, 14918, 15355 | 498AB - 14918 | 498ML |
| 29. | 501DB - 4580, 4826, 6224, 7007 | 501AB - 4580, 6776 | 501ML - 3966, 4569, 4580, 4917, 15379 |
| 30. | 504DB - 3507 | 504AB | 504ML |
| 31. | 505DB - 15307, 15526 | 505AB - 4216, 4917, 5456, 6776, 6953, 7028, 7407, 15452 | 505ML |

Cluster Analysis

Figure 2:
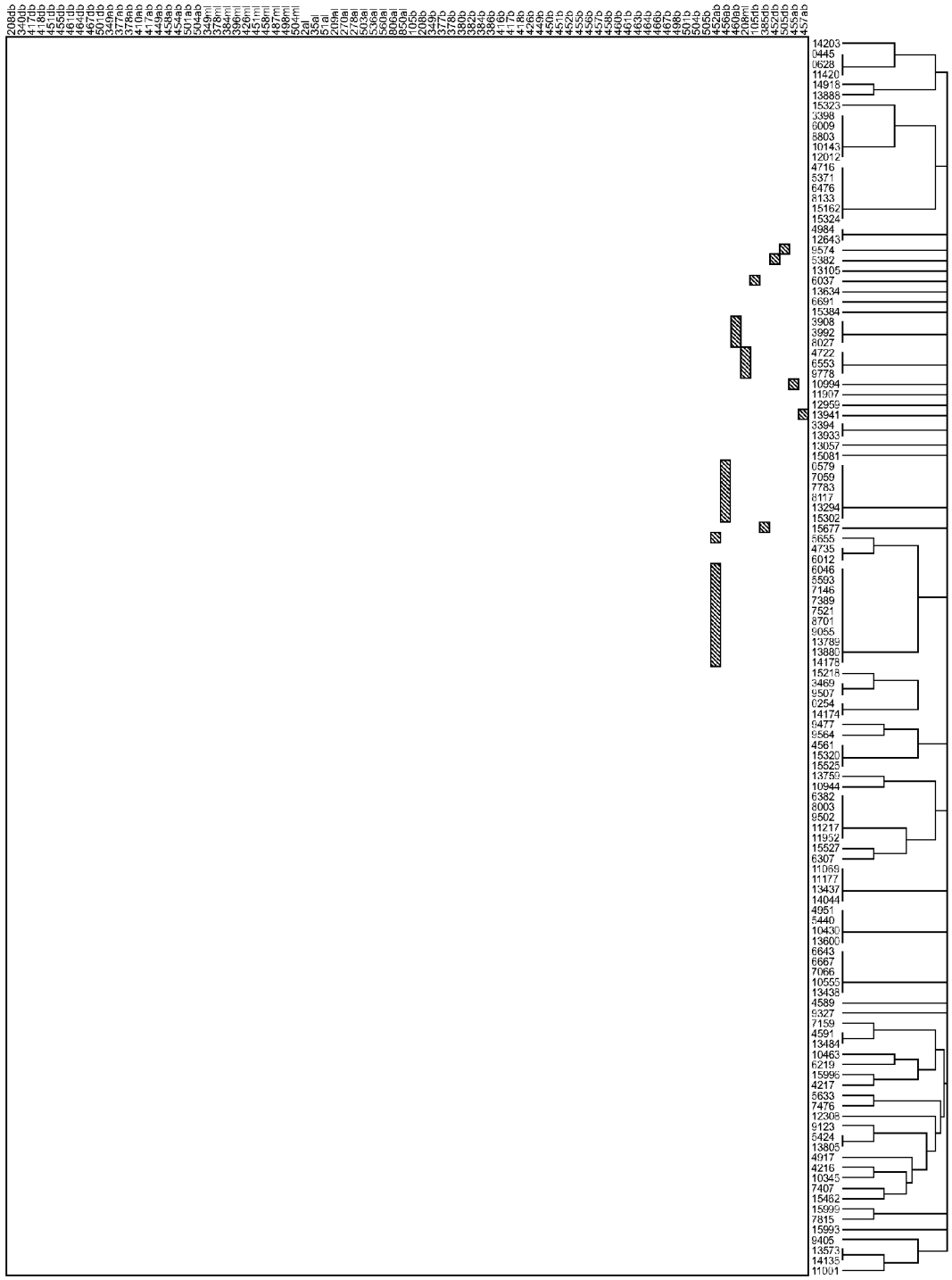
FIG. 2 shows the first half of the non-synonymous clusters produced using Hierarchal Clustering Explorer (HCE).
Figure 3:
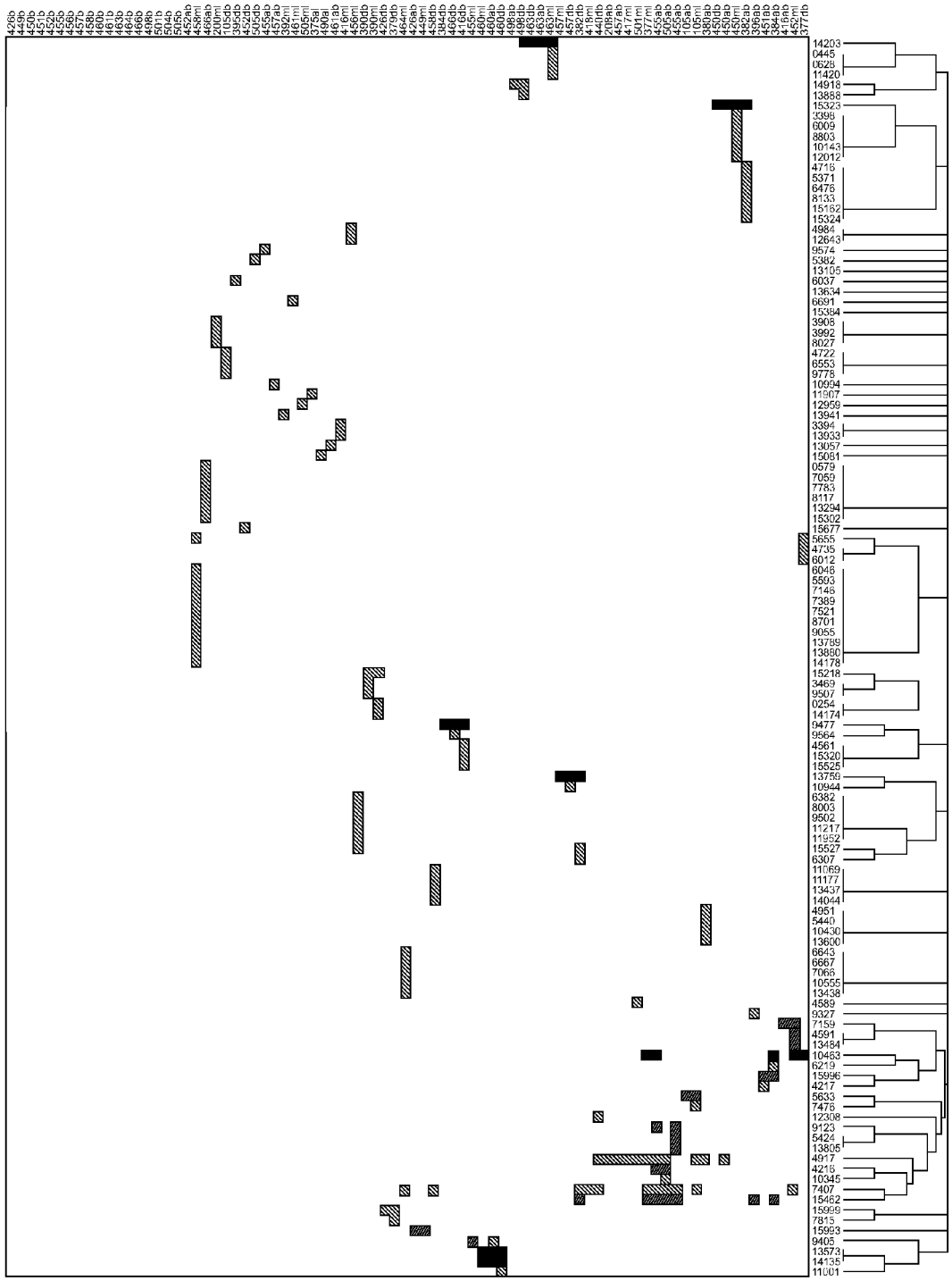
FIG. 3 shows the second half of the non-synonymous clusters produced using Hierarchal Clustering Explorer (HCE).

The mutations identified in the 31 individuals diagnosed with prostate cancer were analyzed using Hierarchical Clustering Explorer (HCE) (www.cs.umd.edu/hcil/multi-cluster; Seo et al, 2002; Seo et al. 2003; Zhao et al 2003; Seo and Shneiderman; Seo et al; 2004a; Seo et al. 2004b; Seo et al. 2005a; Seo et al. 2004c; Seo et al. 2005b). In addition, the mitochondrial genomes from prostate needle biopsy tissue of 12 males clinically symptomatic for prostate cancer, but where pathology results indicated that the prostate tissue was not malignant, were also analyzed. FIGS. 2 and 3 show the cluster analysis of the identified non-synonymous mitochondrial mutations. FIG. 2 is the first half of the cluster analysis and FIG. 3 is the second half of the cluster analysis. The y-axis lists the patient numbers for the 31 individuals with prostate cancer (105, 208, 349, 377, 378, 380, 382, 384, 386, 416, 417, 418, 426, 449, 450, 451, 452, 455, 456, 457, 458, 460, 461, 463, 464, 466, 467, 498, 501, 504, 505) and the 12 individuals showing clinical symptoms but having no malignancy as determined by pathology (2, 35, 51, 209, 270, 278, 375, 480, 503, 536, 560, 858). The y-axis also indicates the source of the tissue (i.e. distant benign (db), adjacent benign (ab), malignant (ml), and (b) blood). Benign glandular tissue from symptomatic but non-malignant tissue of the 12 individuals is indicated by "gl". The x-axis lists the sites of the mutations.

Figure 4:
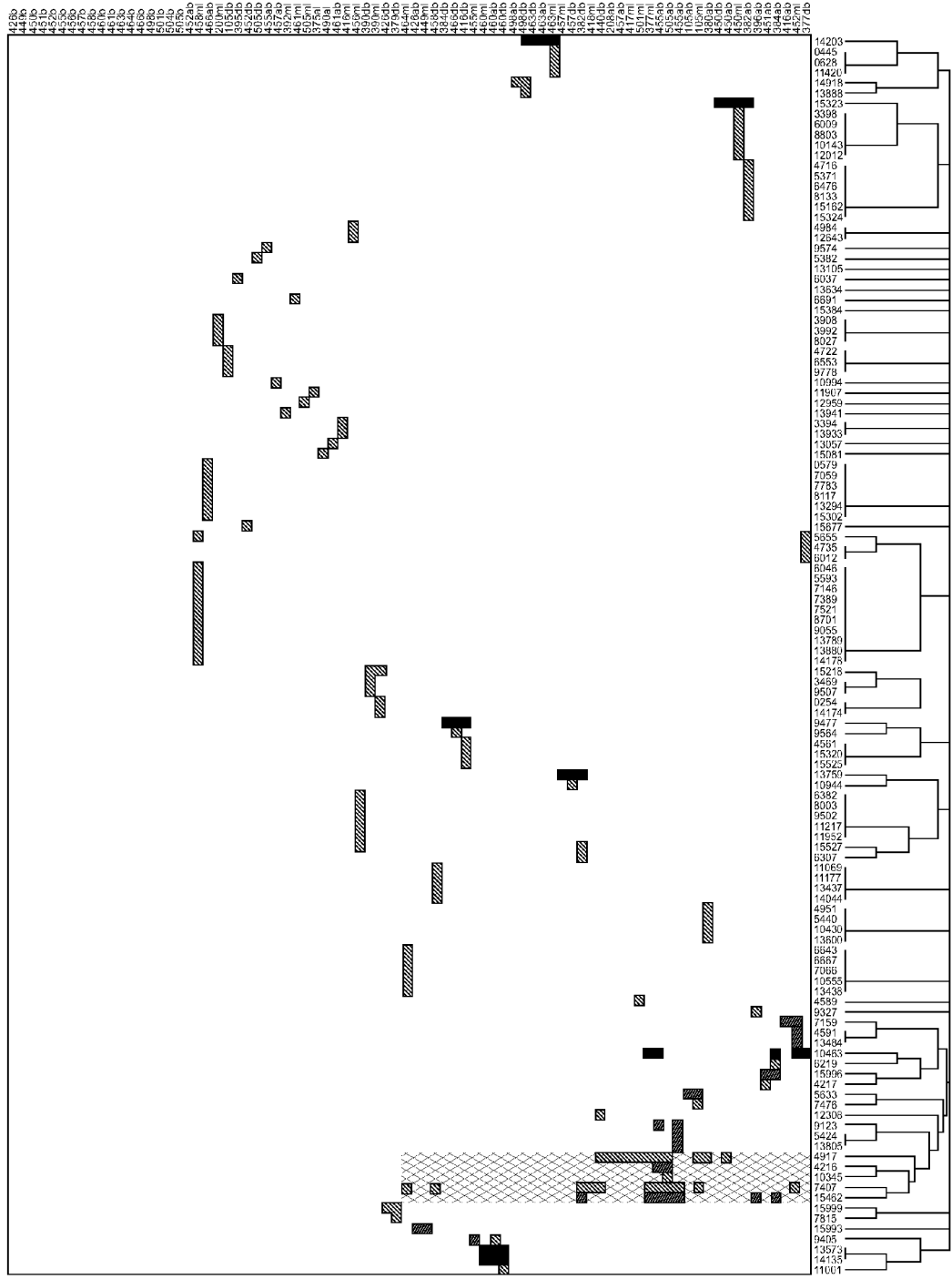
FIG. 4 is a copy of FIG. 3 wherein the important cluster is shaded.

FIG. 4 is a copy of FIG. 3 showing a suite of non-synonymous mutations associated with clinical prostate cancer in the shaded area. The mutations occur in specific genes: Mutations at positions 4216 and 4217 both occur in the ND1 gene (NADH dehydrogenase subunit 1). The mutation at position 4917 occurs in the ND2 gene (NADH dehydrogenase subunit 2). The mutation at position 7407 occurs in the COXI gene (cytochrome c oxidase subunit 1). Finally, the mutation at position 15452 occurs in the CytB gene (cytochrome b). Mutations 4216 and 4217 invoke a non-synonymous mutation at the same amino acid, and like 4917, are secondary mutations associated with Leber's Hereditary Optic Neuropathy (LHON) (Mitochondrial Research Society; Huoponen, 2001; MitoMap). Other than prostate cancer, an association for 7407 remains unattested. A mutation at 15452 was found in 5/5 patients with ubiquinol cytochrome c reductase (complex III) deficiency (Valnot et al. 1999).

In the cohort of 31 men who underwent a prostatectomy for prostate cancer these mutations, one or more, were noted in 20 of the subjects (64.5%). As mentioned above, in each of these individuals, total mitochondrial genome sequences were obtained from prostate cross sections for three types of associated tissues: malignant, benign tissue adjacent to malignant tissue and "distant" benign tissue, removed from any surrounding tissue pathology. Tissues were laser capture microdissected (LCM) by a qualified, clinical pathologist. Sequences were compared to mitochondrial DNA (mtDNA) extracted and sequenced from the patient's blood. Sequencing results indicate that mitochondrial mutations, often heteroplasmic, appear in all three tissue types. Contrary to the analysis of Alonso et al. (2005), mutations in mitochondrial DNA from malignant tissue, adjacent benign and distant benign were found in comparison with mtDNA sequences from the patient's blood. Heteroplasmy, mutant and normal mitochondrial genomes existing within the same individual, is considered evidence of recent mutation (Huoponen, 2001). Most mutations are not held in common between the three tissue types from the same individual. In fact, the comparative mutation loads for each tissue type is roughly the same, indicating that mtDNA mutations are active within the prostate in the presence of tumor, irrespective of prostate tissue type. Moreover, tissue which appears histologically benign, is often found with mutations in the mitochondrial genome. These mutations are not associated with mitochondrial sequences embedded in the nucleus, or NUMTS (nuclear/mitochondrial sequences) (Lopez, 1994). A lengthy cloning and sequencing study of human NUMTS utilizing a Rho⁰ cell line, as well as comparison to known NUMTS archived in the NCBI database was done and no mutations were detected to known mitochondrial pseudogenes archived in public databases to ensure data clean of pseudogene data points.

In the 12 males clinically symptomatic for prostate cancer, wherein the pathology results indicated that the prostate tissue was not malignant, benign glandular tissue was recovered by LCM and the mitochondrial genomes amplified and sequenced from prostate needle biopsy tissues. Results indicate a complete absence of mtDNA mutations in four patients, mutations only in the non-coding control region in four patients, or mutations in both the control region and gene coding regions in four patients. However, the mutation locations were significantly different than the malignant cohort (P>0.01). Additionally, only one coding region mutation was observed in these individuals and of these mutations one fell into the regions mentioned above (i.e. ND1, ND2, COXI and CytB) (patient 375 CytB at position 15081).

When both synonymous and non-synonymous mutations, inclusive of the four protein coding regions, were used as malignant disease markers, 30/31 (97%) of the prostate cancer group was identified. Table 1c lists the synonymous and non-synonymous mutations found in ND1, ND2, COXI, and CytB in tissue samples from the 31 individuals with prostate cancer. Mutations in ND1, ND2, COXI, and CytB are clearly associated with prostate cancer. Although the present invention has identified the mutations listed in Table 1c and FIGS. 2 to 4, the invention includes any mutations in ND1, ND2, COXI and CytB. In the same analyses, 1 of the 12 benign, symptomatic patients was included with the malignant group; however, this patient had a mutation in CytB, which may indicate early cancer progression. The rest of this group clustered with the blood, or normal control.

A statistical analysis of distant benign from malignant subjects compared to the benign glands of the 12 symptomatic but not malignant patients was done. Since there were 31 malignant patients and 12 symptomatic but not malignant subjects, random samples of 6 groups of 12 from the malignant patients were run against the 12 symptomatic but not malignant subjects. A chi square analysis for each of the 6 groups was run. The results are listed in Table 1d. In every case, the differences were significant at 0.01 level, meaning that the difference between mitochondrial sequences from distant benign tissue in malignant subjects and mitochondrial sequences from symptomatic but not malignant subjects was not due to chance 99% of the time. The analysis was based on the number of mutations found in the four coding regions discussed above.

TABLE 1D

Chi-square test

| | |
|---|---|
| 1) First set of DB | 426, 456, 450, 449, 380, 501, 386, 456, 466, 378, 457, 504 |
| 2) Second set of DB | 377, 105, 451, 417, 501, 456, 426, 498, 382, 461, 384, 464 |
| 3) Third set of DB | 467, 208, 466, 505, 452, 458, 105, 498, 380, 463, 208, 377 |
| 4) Fourth set of DB | 416, 504, 457, 466, 382, 452, 460, 450, 498, 386, 418, 501 |
| 5) Fifth set of DB | 456, 452, 461, 505, 464, 460, 378, 455, 417, 505, 449, 349 |
| 6) Sixth set of DB | 463, 426, 498, 349, 455, 466, 452, 380, 386, 461, 450, 460 |

| | Tissues | | | | |
|---|---|---|---|---|---|
| | ND1 | ND2 | COI | CYTB | Xi-Square |
| Symptomatic | 0 | 0 | 0 | 1 | |
| First set | 10 | 8 | 12 | 7 | 35.14 |
| Second set | 3 | 6 | 14 | 9 | 30.11 |
| Third set | 4 | 2 | 7 | 8 | 19.12 |
| Fourth set | 3 | 4 | 7 | 11 | 23.09 |
| Fifth set | 4 | 5 | 10 | 8 | 25.12 |
| Sixth set | 4 | 1 | 5 | 9 | 17.11 |

Symptomatic Patients - 12;
Distant Benign - 6 random sets of 12 each

Example 2

Duplications in the Non-Coding Region of mtDNA from Sun-Exposed Skin

DNA was extracted from tissue samples as described in Example 1, with the use of DNeasy™ kit supplied by Qiagen. A "back to back" primer methodology was used to investigate the incidence of tandem duplications in the non-coding region (NCR) in relation to sun-exposure. 32 age-matched, split human skin samples, from sun-exposed (n=24) and sun-protected body sites (n=10) were investigated.

The following duplication primers from Brockington et al 1993 and Lee et al 1994 were used:

```
                                           SEQ ID NO: 1
   C   L336      AAC ACA TCT CTG CCA AAC CC   20 mer SEQ ID NO: 2
   D   H335      TAA GTG CTG TGG CCA GAA GC   20 mer SEQ ID NO: 3
   E   L467      CCC ATA CTA CTA ATC TCA TC   20 mer SEQ ID NO: 4
   F   H466      AGT GGG AGG GGA AAA TAA TG   20 mer
```

Primers pairs C/D and E/F are 'back to back' at the site of two separate sets of direct repeats in the non-coding region. As a result they only generate a product if a duplication is present at these points. Products generated are 260 bp and/or less common 200 bp variant. Modified PCR conditions are: 100 ng total cellular DNA, 200 µM dNTPs, 2.5 U HotStarTaq polymerase and PCR buffer (Qiagen, Uk), 25 pmoles of primers: one cycle of 94° C. for 4 minutes, 36 cycles of 94° C.×1 minute, 55° C.×1 minute, 72° C.×1 minute and one cycle of 72° C.×7 minutes.

An increased incidence of duplications with increasing sun-exposure was observed, with duplications identified in 10/24 but 0/10 samples from sun-exposed and sun-protected skin respectively (Fisher's exact test, p=0.015) (Birch-Machin and Krishnan 2001). The sizes of the most frequent duplications were 200 and 260 base pairs. Interestingly these same samples also contained high levels (>1%) of the 4977 bp common mtDNA deletion as determined by an established quantitative 3-primer PCR assay described in Example 6.

Example 3

Mutation Fingerprint of mtDNA in Human NMSC and its Precursor Lesions

DNA was extracted from human skin tissue samples as described in Example 1, with the use of DNeasy™ by Qiagen Using specific primers, mtDNA is amplified by PCR and following DNA sample preparation (Qiagen), mutations are identified by automated sequencing (PE Applied Biosystems) using BigDye™ Terminator Cycle sequencing. This methodology is described in Healy et al. 2000; Harding et al. 2000. The entire 16,569 bp human mitochondrial genome is sequenced using established PCR primer pairs, which are known not to amplify pseudogenes, or other nuclear loci. Any putative DNA changes are confirmed by comparison to the revised "Cambridge" human mtDNA reference (Andrews et al. 1999). The sequences obtained from the tumour mtDNA are first compared for known polymorphisms (Andrews et al. 1999; MITOMAP) and then compared with the mtDNA sequence from the normal perilesional skin to identify genuine somatic mutations.

DHPLC is performed on the WAVE™ DNA Fragment Analysis System (Transgenomic, Omaha, USA) which provides a fully automated screening procedure. The same technology is used to screen for heteroplasmic mutations in the skin tumour mtDNA.

Using the back to back primer methodology described in Example 2, the pattern of DNA length mutations (i.e. tandem duplications) in the hypervariable segments of the non-coding region (NCR) are rapidly screened.

Example 4

Deletion Spectrum of the Entire Mitochondrial Genome in Human NMSC and its Precursor Lesions MtDNA damage in squamous cell carcinomas (SCCS), Basal cell carcinomas (BCCS) and putative precursor lesions such as Bowen's disease and actinic keratoses (As) was compared to adjacent perilesional skin taken from different sun-exposed body sites. A long-extension PCR technique (LX-PCR) (Ray et al. 1998) was used to amplify the entire mitochondrial genome in order to determine the whole deletion spectrum of mtDNA. A myriad of specific deletions have been observed to occur in the mitochondrial genome. Not all deletions will correlate with non-melanoma skin cancer; however, for an accurate diagnostic method, those deletions that are associated with the disease must be known.

DNA is extracted by use of a commercial kit (Qiagen) according to the manufacturer's recommendations. The entire mitochondrial genome is amplified in two separate reactions using the Expand TM Long Template PCR System™ (Boehringer Manheim, Switzerland). The PCR primers used are those described by Kleinle et al. (1997) covering the following regions of the Cambridge sequence (Andrews et al. 1999): DIA (nucleotides (nt) 336-363), DIB (nt 282-255), OLA (nt 5756-5781), and OLB (nt 5745-5781). These large products eliminate amplification of nuclear pseudogenes. The sequences of the primers are as follows:

```
DIAF: (336-363)
5' AACACATCTCTGCCAAACCCCAAAAACA 3'      SEQ ID NO: 5

OLBR: (5745-5721)
5' CCGGCGGCGGGAGAAGTAGATTGAA 3'         SEQ ID NO: 6

OLAF: (5756-5781)
5' GGGAGAAGCCCCGGCAGGTTTGAAGC 3'        SEQ ID NO: 7

DIBR: (282-255)
5' ATGATGTCTGTGTGGAAAGTGGCTGTGC 3'      SEQ ID NO: 8
```

Amplifications are performed in 50 microlitre reactions containing 16 pmol of each primer, 500 µmol dNTPs, 10×PCR buffer with 22.5 mM $MgCl_2$ and detergents (kit), 0.75 µl of enzyme ($3.5 \times 10^3$ units/ml) and 50-200 ng of total DNA. One reaction generates 11,095 bp segments of the genome, while another results in 5,409 bp lengths (e.g. Kleinle et al, 1997). The PCR amplification conditions consists of a denaturing stage at 93° C. for 1 min 30 s, followed by 10 cycles of 93° C. for 30 s, 60° C. for 30 s and 68° C. for 12 min, followed by a further 20 cycles of the same profile with an additional 5 s added to the elongation time every cycle. There is a final cycle of 93° C. for 30 s, 60° C. for 30 s and an elongation time of 68° C. for 26 minutes. To ensure reproducibility, a known amount of DNA is separated on a 1% agarose gel and only samples which have at least the same amount of DNA are included in the analysis.

A greater mean number of deletions is found with increasing UV exposure in the tumour samples, as shown in Table 2.

TABLE 2

Comparison of the mean number of deletions observed in the LX-PCR of mtDNA between normal and tumour skin taken from different UV-exposed body sites.

| UV exposure | Mean number of deletions in adjacent normal epidermis | Mean number of deletions in epidermal tumour |
|---|---|---|
| Constant (n = 5) | 1.0 | 3.6 |
| Intermittent (n = 2) | 0 | 1.5 |
| Sun-protected (n = 2) | 0 | 0 |

Example 5

Aging and MtDNA

Using temporal maternal line comparisons (i.e. great-grandchild through great-grand parents), the entire sequence of mtDNA extracted from a given tissue is rapidly, and accurately sequenced, in order to definitively state the arrangement of nucleotide base pairs for that specific molecule and possible changes through time. These characterizations are compared to health status, aging indicators and between specific maternal lines, within larger populations. This combined information allows crucial statistical discrimination between separate causes resulting in the same mutation/deletion and establishes that the mtDNA sequences, used as a bio-marker, has the required index of specificity and sensitivity in order to establish its validity. In addition, the proportions of base pair deletions and mutations are compared for consistency in various tissues across the 4 maternal generations. Recent methodological developments have permitted detection of base pair deletions implicated in aging in blood samples (Bassam et al. 1991) and have raised the possibility that blood samples may be used to study mtDNA in lieu of skeletal muscle (von Wurmb et al. 1998). After establishing the efficacy of employing leukocytes in lieu of muscle tissue, as representative of mtDNA deletions and/or mutations, the next step measures only mtDNA in leukocytes. MtDNA deletions/mutations are then determined as previously described.

Skeletal muscle or leukocytes are obtained from a patient. DNA is extracted as set out in Example 1. The following primers were used:

```
12ST1: (1257-1279)
5' TATACCGCCATCTTCAGCAAAC3'            SEQ ID NO: 9

12ST2: (1433-1411)
5' TACTGCTAAATCCACCTTCGAC 3'           SEQ ID NO: 10

D1F:
5' CCTTACACTATTCCTCATCACC 3'           SEQ ID NO: 11

D1R:
5' TGTGGTCTTTGGAGTAGAAACC 3'           SEQ ID NO: 12
```

Amplifications were performed in 50 microlitre reactions containing 2.0 µmol of each primer, 250 µmol dNTPs, 10×PCR buffer (Thermopol Reaction Buffer), bovine serum albumin, 0.5 units Deep vent polymerase and 50-200 ng of total DNA. The PCR amplification conditions consists of a denaturing stage at 95° C. for 5 min (hot start), followed by 30 cycles of 94° C. for 30 s, 60° C. for 60 s and 72° C. for 30 s with a final extension at 72° C. for 10 min. Gel electrophoresis was performed on a 2% agarose gel at 125 volts for 60 min, stained with ethidium bromide, and visualized under UV light. To ensure reproducibility, a known amount of DNA was separated on a 2% agarose gel and only samples which have the same amount of DNA were included in the analysis.

Example 6

Quantitative Detection of the 4977 bp Common mtDNA Deletion by 3-Primer PCR Where appropriate the incidence of the common deletion is determined in a quantitative manner by a 3-primer PCR method which detects levels greater than 1-5% or a dilution PCR method which detects levels less than 1% down to $10^{-4}$%. (See Example 7) Samples are obtained and DNA extracted as described in Example 1. To simultaneously detect and quantify the ratios of both deleted and wild type (wt) mtDNAs in the DNA samples, a 3-primer PCR procedure is used (as described in Birch-Machin et al 1998). Primers A, and C correspond to heavy strand positions 13720-13705 and 9028-9008 respectively (Anderson et al., 1981); primer B corresponds to light strand positions 8273-8289. Primer C maps to a mtDNA region within the common deletion, whereas primers A and B flank the deleted region. Therefore primers B and C only amplify wt-mtDNAs and primers A and B only amplify deleted mtDNAs (the distance between the two primers in the absence of the deletion, approximately 5.5 kb, is too long to be amplified under our PCR conditions as described below).

Using three primers allowed the simultaneous detection of two bands, the larger one (755 bp) corresponding to the wt-mtDNA, and the smaller one (470 bp) corresponding to deleted mtDNA harbouring the 'common deletion'. The PCR reaction mixture (25 µl total volume) contained 100 ng total cellular DNA, 200 µM dNTPs, 10 mM Tris-HCl (pH 8.8), 50 mM KCl, 1.5 mM Mg Cl$_2$, 0.1% Triton X-100, 2.5 U Taq DNA polymerase (BioTaq, BiolineUK Limited, London), 25 pmoles of primers A and B, 6.25 pmoles of primer C and 3 µCi of [α-$^{32}$P]-dATP. The PCR conditions were 25 cycles of 94° C. at 1 minute, 55° C. at 1 minute, 72° C. at 2 minutes including a final extension of 15 minutes at 72° C. These PCR products were then electrophoresed through a 6% nondenaturing polyacrylamide gel and the radioactive PCR fragments were quantified by phophorimage analysis using the ImageQuant™ software (Molecular Dynamics, Chesham UK).

Example 7

Serial Dilution PCR Method to Quantitatively Detect Low Levels (<1%) of the Common mtDNA Deletion A semi-quantitative PCR method (Corral-Debrinski et al 1991) is used to estimate the proportion of the common deletion in the total mtDNA extracted from the tissue/cell samples. Biological samples are obtained and DNA extracted as described in Example 1. The DNA sample is initially linearised using the restriction enzyme Bam HI (1 µl enzyme and 1 µl of commercially supplied buffer) at 37° C. for 90 minutes. Serial dilutions are performed in two-fold steps (for total mtDNA there was an initial 10-fold dilution) and PCR performed for each dilution (1 µl) using the following primers:
Primers for Total mtDNA
L3108 (nt3108-3127)
H3717 (nt3717-3701)
Primers for Common Deletion
L8282 (nt8282-8305)
H13851 (nt13851-13832)

The reaction conditions are as follows:
One cycle 94° C. for 2 minutes, 34 cycles of 94° C. for 45 seconds, 51° C. for 30 seconds (total mtDNA), 56° C. for 30 seconds (common deletion), 72° C. for 1 minute and one final cycle of 72° C. for 8 minutes. All PCR reactions are carried out in the following mixture (50 µl): Sample DNA 1 µl, 0.6 µM forward primer, 0.6 µM reverse primer, 0.2 mM dNTP's, 5 µl GeneAmp® 10×PCR Buffer, (Perkin Elmer), 0.2 µl Amplitaq® DNA polymerase (Perkin Elmer), 35.75 µl sterile autoclaved double distilled water.

Following electrophoresis the PCR products are visualised on a UV transilluminator (TMW-20, Flowgen Ltd., Lichfield, UK) and a digital image of the gel obtained using image acquisition apparatus (Alpha Imager 2000, Alpha Innotech Corporation, supplied by Flowgen Ltd., Lichfield, UK). The associated image analysis software (Alpha Ease v3.3, Alpha Innotech Corp.) allows the calculation of the integrated optical density (IOD) for each PCR product in a dilution series. The band where an IOD value of zero is obtained for both total mtDNA and deleted mtDNA and the corresponding dilution values are used to calculate the percentage of common deletion in the sample thus:

$$\% \text{ common deletion } = \frac{\text{total } mtDNA \text{ dilution } factor^{(IODZero)} \times 100}{\text{common deletion dilution } factor^{(IODZero)}}$$

Example 8

Denaturing High Performance Liquid Chromatography (DHPLC)

Samples are obtained and DNA extracted as in Example 1. PCR in 13 overlapping fragments using two different PCR conditions as described by van den Bosch et al. (2000). The following three mtDNA specific primer pairs for PCR:

```
Oligo Sequence
Mt3118F    CCCTGTACGAAAGGACAAGAG      SEQ ID NO: 13

Mt3334R    TGAGGAGTAGGAGGTTGG         SEQ ID NO: 14

Mt8207F    CCCATCGTCCTAGAATTAATTCC    SEQ ID NO: 15

Mt8400R    ATGGTGGGCCATACGGTAG        SEQ ID NO: 16

Mt14427F   CCCATGCCTCAGGATACTCCTC     SEQ ID NO: 17

Mt14997R   GCGTGAAGGTAGCGGATG         SEQ ID NO: 18
```

The 1-2 kb PCR products are digested into fragments of 90-600 bp and resolved at their optimal melting temperature. Mutations are represented as two peaks and mutations with low percentages, such as <2% heteroplasmy as a "shoulder" in the peak.

DHPLC is performed with a mobile phase consisting of two eluents (pH 7.0). Buffer A contains triethylammonium acetate (TEAA), which interacts with both the negatively charged phosphate groups on the DNA as well as the surface of the column. Buffer B contains TEAA with 25% of the denaturing agent acetonitrile. Fragments were eluted with a linear acetonitrile gradient at a constant flow rate. Increasing the concentration of acetonitrile will denature the fragments. Table 3 below is an example of a standard method for DHPLC of a PCR reaction generated using the WAVEMAKER software (Transgenomics) according to manufacturer's instructions.

TABLE 3

Standard Method for DHPLC

| Step | Time | % A (buffer) | % B (buffer) | Ml/min (flow rate) |
|---|---|---|---|---|
| Loading | 0.0 | 52 | 48 | 0.90 |
| Start Gradient | 0.1 | 47 | 53 | |
| Stop Gradient | 4.1 | 39 | 61 | |
| Start Clean | 4.2 | 0 | 100 | |
| Stop Clean | 4.7 | 0 | 100 | |
| Start Equilibrate | 4.8 | 52 | 48 | |
| Stop Equilibrate | 6.8 | 52 | 48 | |

The temperatures for successful resolution of the various heteroduplexes are detailed below and can simply be substituted into the relevant places in Table 2:

| Fragment | Melting temp (° C.) | Gradient of % Buffer B |
|---|---|---|
| Mt3118F | 59 | 51-59 |
| Mt8207F | 58 | 50-58 |
| Mt14427F | 56 | 60-68 |

Example 9

Figure 1:
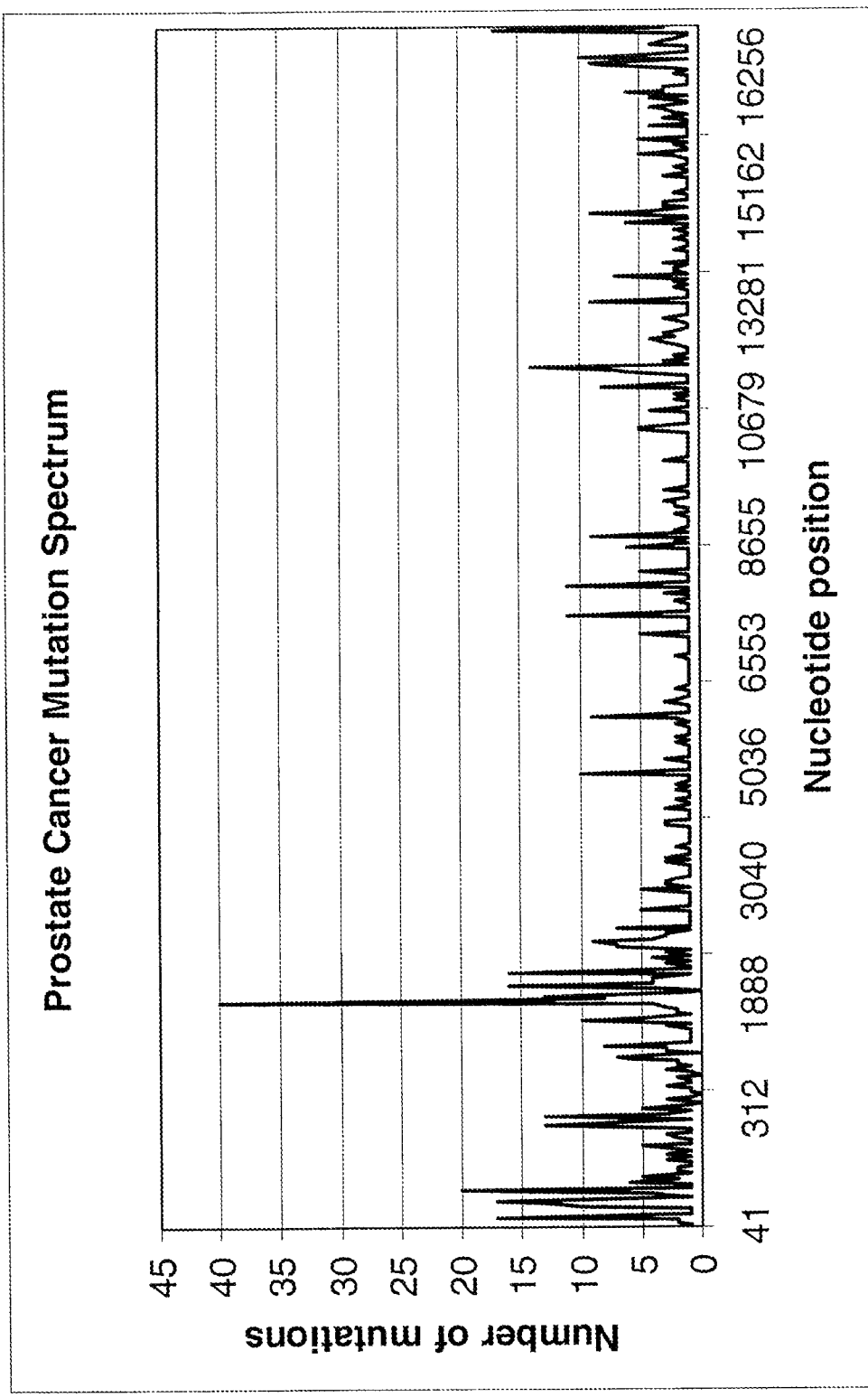
FIG. 1 is a histogram showing the number of mutations at nucleotide position in mitochondrial DNA from patients with prostate cancer.

An extensive survey of mtDNA D-loop sequences from 49 prostate needle biopsy patients (46 diagnosed with malignancy) demonstrated mtDNA mutations in all prostatic tissues inclusive of benign prostatic hyperplasia (BPH), available Gleason grades and stroma as compared with the mitochondrial DNA of the patients blood. Moreover, an expanded study of mitochondrial genomes from 31 prostatectomy patients demonstrates equivocable hyper-mutation (Chen et al. 2002; Chen et al. 2003) loads in matched malignant glands, adjacent benign glands (nearby the malignant glands), and distal benign glands (located in tissue free of malignant pathology removed from any malignant pathology) as shown in Table 4. The mutations of Table 4 are also provided in SEQ ID No: 102 which lists the substitutions, SEQ ID NOs: 103 to 109 which lists the deletions, and SEQ ID No: 110 to 138 which lists the insertions. Polymorphisms and mutation positions were determined by comparison to the Revised Cambridge Reference Sequence (2001), however the historical numbering has been maintained such that the deletion at position 3106 is denoted as a gap and the rare polymorphism 750A has been retained. The numbering of the bases is based on the revised Cambridge Reference Sequence having a total of 16569 base positions. A histogram showing the number of mutations per location of the mitochondrial genome is shown in FIG. 1. As can be seen in FIG. 1, the mutations were found throughout the mtDNA genome and in all diseased prostates. However, certain "hot spots" were also apparent, for example in the D-loop region and the 16s region. These data sets imply that the designation of malignant or benign tissue, as made by a qualified pathologist using routine histological methods and grading standards, does not identify early disease progression. This strongly suggests that malignant transformation begins at the cellular level before the morphological characteristics of a cell are altered. Importantly, the mutation patterns are completely inconsistent for matched prostate tissue from an individual patient, or in comparison to another patient, perhaps indicating possible tissue sites where clonal expansion of malignant cells may occur. Moreover, separate needle biopsies with the same Gleason score, from the same individual almost always demonstrate alternative mtDNA mutation patterns. This indicates that total mutation load rather than specific mutation sites may be more representative of the disease and progression of the disease.

Since this data was gathered from individuals with known prostate cancer, and in the prostatectomy group with known advanced staging, it is likely that histologically benign tissue has undergone some intracellular transformation(s) associated with neoplasia and possible progression towards malignancy. Benign tissue harboring mtDNA mutations serve as a "biosensor" which can be monitored for increasing mutations indicative of the rate of disease progression. This rate may also indicate tumor aggression. Moreover, the effectiveness of a specific therapy could also be monitored based on the change in this mutational pattern.

This technique may be used as a confirmatory test for benign needle biopsies. Currently when a patient has a needle biopsy performed on the prostate and the tissue looks histologically benign he is sent home and is usually scheduled for follow-up needle biopsies in six months. Use of the above method would examine the already taken needle biopsy tissue and either confirm that the tissue is benign on the molecular level as well, or find evidence that there is in fact a malignancy in the prostate that was geographically missed by the needle biopsy technique, or that the tissue is pre-neoplastic or neoplastic at the molecular level. This could potentially save a lot of people from undergoing multiple surgeries or allow for early preventative treatment.

TABLE 4

Base Mutations: Observed mutations of homoplasmic to homoplasmic, homoplasmic to heteroplasmic, and heteroplasmic to homoplasmic

| BP Historical Numbering** | BP eliminating position gap at 3106 | Homo-Homo | Homo-Hetero | Hetero-Homo |
|---|---|---|---|---|
| 10 | 10 | T-C | T-T/C | |
| 31 | 31 | | C-C/T | |
| 41 | 41 | C-T | C-C/T | |
| 55 | 55 | C-T | | |
| 57 | 57 | A-T | | |
| 61 | 61 | | C-C/T | |
| 64 | 64 | C-T | | |
| 72 | 72 | C-T | C-C/T | |
| | | T-C | T-T/C | |
| 73 | 73 | A-G | A-A/G | |
| 81.1 | 81.1 | INS T | | |
| 93 | 93 | | G-G/A | |
| 94 | 94 | | A-A/G | |
| 104 | 104 | | C-C/T | |
| 113 | 113 | | C-C/T | |
| 119 | 119 | | C-C/T | |
| 128 | 128 | C-T | | |
| 146 | 146 | C-T | C-C/T | |
| | | T-C | T-T/C | |
| 150 | 150 | C-T | C-C/T | |
| | | T-C | T-T/C | |
| 152 | 152 | C-T | C-C/T | |
| | | T-C | T-T/C | |
| 153 | 153 | A-G | A-A/G | |
| | | G-A | G-G/A | |
| 170 | 170 | | C-C/T | |
| 182 | 182 | C-T | C-C/T | |
| 185 | 185 | G-A | G-G/A | |
| | | | A-A/G | |
| | | | G-G/T | |
| 188 | 188 | A-G | | |
| | | G-A | G-G/A | |
| 189 | 189 | A-G | A-A/G | |
| | | G-A | G-G/A | |
| 192 | 192 | T-C | | |
| 194 | 194 | T-C | T-T/C | |
| | | C-T | | |

TABLE 4-continued

Base Mutations: Observed mutations of homoplasmic to homoplasmic, homoplasmic to heteroplasmic, and heteroplasmic to homoplasmic

| BP Historical Numbering** | BP eliminating position gap at 3106 | Homo-Homo | Homo-Hetero | Hetero-Homo |
|---|---|---|---|---|
| 195 | 195 | C-T | C-C/T | |
|  |  |  | T-T/C | |
| 196 | 196 | T-C | | |
| 198 | 198 | | C-C/T | |
| 199 | 199 | | T-T/C | |
|  |  |  | C-C/T | |
| 200 | 200 | G-A | G-G/A | |
| 200 | 200 | A-G | A-A/G | |
| 204 | 204 | T-C | T-T/C | |
|  |  |  | C-C/T | |
| 205 | 205 | | A-A/G | |
| 207 | 207 | | A-A/G | |
|  |  | G-A | G-G/A | |
| 208 | 208 | | T-T/C | |
| 214 | 214 | | A-A/G | |
| 217 | 217 | C-T | | |
| 222 | 222 | C-T | | |
| 225 | 225 | A-G | A-A/G | |
| 226 | 226 | C-T | C-C/T | |
| 228 | 228 | A-G | A-A/G | |
|  |  |  | G-G/A | |
| 229 | 229 | G-T | | |
| 234 | 234 | | A-A/G | |
| 235 | 235 | A-G | | |
|  |  |  | G-G/A | |
| 239 | 239 | T-C | | |
| 247 | 247 | | G-G/A | |
| 248 | 248 | DEL A | | |
| 262 | 262 | | C-C/T | |
| 263 | 263 | | G-G/T | |
|  |  | A-G | A-A/G | |
| 264 | 264 | T-C | | |
| 277 | 277 | | C-C/T | |
| 280 | 280 | | C-C/T | |
| 295 | 295 | T-C | T-T/C | |
| 297 | 297 | G-A | G-G/A | |
| 303.1 | 303.1 | INS C | | |
| 303.2 | 303.2 | INS C | | |
| 305 | 305 | | C-C/T | |
| 309 | 309 | | T-T/C | |
|  |  |  | C-C/T | |
| 309 | 309 | DEL C | | |
| 309.1 | 309.1 | INS C | | |
| 309.2 | 309.2 | INS C | | |
| 309.3 | 309.3 | INS C | | |
| 310 | 310 | DEL C | T-T/C | T/C-T |
|  |  | DEL T | C-C/T | |
| 311 | 311 | | C-C/T | |
| 311.1 | 311.1 | INS C | | |
| 312 | 312 | | C-C/T | |
| 313 | 313 | | C-C/T | |
| 315.1 | 315.1 | INS C | | |
| 315.2 | 315.2 | INS C | | |
| 323 | 323 | | G-G/A | |
| 325 | 325 | C-T | C-C/T | |
| 329 | 329 | G-T | | |
| 394 | 394 | | C-C/T | |
| 416.1 | 416.1 | INS G/A | | |
| 419 | 419 | | A-A/G | |
| 456 | 456 | C-T | | |
|  |  |  | T-T/C | |
| 462 | 462 | T-C | | |
| 465 | 465 | | T-T/C | |
| 468 | 468 | | C-C/T | |
| 477 | 477 | C-T | | |
| 481 | 481 | C-T | | |
| 482 | 482 | C-T | | |
| 489 | 489 | C-T | C-C/T | |
| 497 | 497 | T-C | T-T/C | |
| 499 | 499 | A-G | | |
| 501 | 501 | | C-C/T | |
| 505 | 505 | | C-C/T | |
| 506 | 506 | | | C/T-C |
| 508 | 508 | G-A | | |
| 513 | 513 | A-G | | |
| 513 | 513 | DEL A | | |
| 514.1 | 514.1 | INS C | | |
| 515 | 515 | | A-A/G | |
| 515 | 515 | DEL A | | |
| 515.1 | 515.1 | INS A | | |
| 517 | 517 | | T-T/A | |
| 523 | 523 | | A-A/G | |
| 523 | 523 | DEL A | | |
| 523.1 | 523.1 | INS C | | |
| 523.2 | 523.2 | INS A | | |
| 523.3 | 523.3 | INS C | | |
| 523.4 | 523.4 | INS A | | |
| 533 | 533 | A-G | A-A\G | |
| 536 | 536 | | C-C/T | |
| 567.1 | 567.1 | INS C | | |
| 568.1 | 568.1 | INS C | | |
| 568.2 | 568.2 | INS C | | |
| 709 | 709 | | A-A/G | |
|  |  |  | G-G/A | |
| 785 | 785 | | C-C/G | |
| 857 | 857 | G-C | | |
| 909 | 909 | | G-G/A | |
| 1189 | 1189 | | C-C/T | |
| 1247 | 1247 | | G-G/A | |
| 1431 | 1431 | | G-G/A | |
| 1693 | 1693 | C-T | | |
| 1709 | 1709 | | | A/G-G |
| 1719 | 1719 | | | A/G-G |
| 1719 | 1719 | | A-A/G | A/G-A |
| 1761 | 1761 | | | A/T-A |
| 1766 | 1766 | | | C/T-T |
| 1811 | 1811 | G-A | G-G/A | |
| 1842 | 1842 | | | A/G-A |
| 1883 | 1883 | | | A/G-G |
| 1888 | 1888 | G-A | G-G/A | A/G-G |
|  |  |  |  | A/G-A |
| 2005 | 2005 | | | C/T-C |
| 2056 | 2056 | | | A/G-G |
| 2068.1 | 2068.1 | INS A | | |
| 2075 | 2075 | | | T/G-T |
| 2257 | 2257 | | | C/T-C |
| 2258 | 2258 | | | A/G-A |
| 2259 | 2259 | T-C | | |
| 2261 | 2261 | | C-C/T | |
| 2280 | 2280 | | | C/T-C |
| 2351 | 2351 | | | C/T-T |
| 2352 | 2352 | | | C/T-T |
| 2357 | 2357 | | | C/T-C |
| 2359 | 2359 | | | C/T-C |
| 2389 | 2389 | | | C/T-C |
| 2596 | 2596 | | G-G/A | |
| 2627 | 2627 | | G-G/A | |
| 2657 | 2657 | C-T | | |
| 2683 | 2683 | | C-C/T | |
| 2689 | 2689 | | C-C/T | |
| 2706 | 2706 | A-G | A-A/G | |
| 2761 | 2761 | C-T | | |
| 2857 | 2857 | | C-C/T | |
| 2885 | 2885 | | C-C/T | |
| 2927 | 2927 | C-T | | |
| 2948 | 2948 | C-T | | |
| 2952 | 2952 | | | C/T-T |
| 3010 | 3010 | A-G | A-A/G | |
| 3013 | 3013 | | G-G/A | |
| 3036 | 3036 | | | A/G-G |
| 3040 | 3040 | | | A/G-G |
| 3046 | 3046 | | | C/T-C |
| 3308 | 3307 | | T-T/C | |

TABLE 4-continued

Base Mutations: Observed mutations of homoplasmic to homoplasmic, homoplasmic to heteroplasmic, and heteroplasmic to homoplasmic

| BP Historical Numbering** | BP eliminating position gap at 3106 | Homo-Homo | Homo-Hetero | Hetero-Homo |
|---|---|---|---|---|
| 3338 | 3337 | | | C/T-T |
| 3349 | 3348 | | | A/G-A |
| 3394 | 3393 | C-T | | |
| 3398 | 3397 | T-C | | |
| 3469.1 | 3468.1 | INS T | | |
| 3480 | 3479 | G-A | | |
| 3499 | 3498 | | | A/G-A |
| 3507 | 3506 | C-A | | |
| 3589 | 3588 | | C-C/T | |
| 3594 | 3593 | | C-C/T | |
| 3657 | 3656 | C-T | | |
| 3666 | 3665 | G-A | | |
| 3688 | 3687 | | G-G/A | |
| 3693 | 3692 | | G-G/A | |
| 3744.1 | 3743.1 | INS T | | |
| 3908 | 3907 | C-T | | |
| 3966 | 3965 | | C-C/T | |
| 3969 | 3968 | C-T | | |
| 3992 | 3991 | C-T | | |
| 4017 | 4016 | C-T | | |
| 4185 | 4184 | C-T | | |
| 4216 | 4215 | T-C | T-T/C | |
| 4217 | 4216 | | A-A/G | |
| 4239 | 4238 | C-T | | |
| 4418 | 4417 | | C-C/T | |
| 4561 | 4560 | C-T | | |
| 4569 | 4568 | | G-G/A | |
| 4580 | 4579 | | A-A/G | |
| 4591 | 4590 | | T-T/C | |
| 4646 | 4645 | C-T | | |
| 4655 | 4654 | | A-A/G | |
| 4703 | 4702 | | C-C/T | |
| 4716 | 4715 | | C-C/T | |
| 4722 | 4721 | | A-A/G | |
| 4733 | 4732 | | C-C/T | |
| 4735 | 4734 | | C-C/T | |
| 4787 | 4786 | G-A | G-G/A | |
| 4826 | 4825 | | C-C/T | |
| 4864 | 4863 | | C-C/T | |
| 4892 | 4891 | | C-C/T | |
| 4917 | 4916 | A-G | A-A/G | |
| | | | G-G/A | |
| 4951 | 4950 | | C-C/T | |
| 5036 | 5035 | | A-A/G | |
| 5046 | 5045 | | G-G/A | |
| 5102 | 5101 | | A-A/G | |
| 5147 | 5146 | G-A | G-G/A | |
| | | | A-A/G | |
| 5174 | 5173 | | C-C/T | |
| 5198 | 5197 | | G-G/A | |
| 5213 | 5212 | | C-C/T | |
| 5300 | 5299 | | C-C/T | |
| 5312 | 5311 | | C-C/T | |
| 5371 | 5370 | | C-C/T | |
| 5424 | 5423 | | C-C/T | |
| 5440 | 5439 | | C-C/T | |
| 5456 | 5455 | | C-C/T | |
| 5593 | 5592 | | T-T/C | |
| 5633 | 5632 | | T-T/C | |
| 5650 | 5649 | | G-G/A | |
| 5655 | 5654 | | T-C/T | |
| 5656 | 5655 | A-G | A-A/G | |
| 5663 | 5662 | | C-C/T | |
| 5677 | 5676 | C-T | | |
| 5882 | 5881 | | C-C/T | |
| 5897 | 5896 | | C-C/T | |
| 5984 | 5983 | A-G | A-A/G | |
| 5985 | 5984 | | A-A/G | |
| 5999 | 5998 | C-T | | |
| 6009 | 6008 | | C-C/T | |
| 6028 | 6027 | | | A/G-G |
| 6037 | 6036 | | G-G/A | |
| 6041 | 6040 | | C-C/T | |
| 6047 | 6046 | G-A | | |
| 6059 | 6058 | | C-C/T | |
| 6147 | 6146 | C-T | | |
| 6219 | 6218 | | C-C/T | |
| 6221 | 6220 | | C-C/T | |
| 6224 | 6223 | | C-C/T | |
| 6307 | 6306 | | A-A/G | |
| 6314 | 6313 | | C-C/T | |
| 6382 | 6381 | G-A | | |
| 6548 | 6547 | | C-C/T | |
| 6553 | 6552 | | C-C/T | |
| 6557 | 6556 | | C-C/T | |
| 6579 | 6578 | G-A | | |
| 6643 | 6642 | | T-T/C | |
| 6667 | 6666 | | C-C/T | |
| 6686 | 6685 | T-C | | |
| 6691 | 6690 | G-A | | |
| 6776 | 6775 | C-T | C-C/T | |
| | | T-C | T-T/C | |
| 6827 | 6826 | | T-T/C | |
| 6912 | 6911 | | G-G/A | |
| 6917.1 | 6916.1 | INS T | | |
| 6953 | 6952 | G-A | | |
| 6989 | 6988 | | A-A/G | |
| 7007 | 7006 | C-T | | |
| 7013 | 7012 | | G-G/A | |
| 7028 | 7027 | C-T | C-C/T | |
| | | | T-T/C | |
| 7055 | 7054 | | A-A/G | |
| 7059 | 7058 | | G-G/A | |
| 7146 | 7145 | | A-A/G | |
| 7159 | 7158 | | T-T/C | |
| 7184 | 7183 | G-A | G-G/A | |
| 7256 | 7255 | | C-C/T | |
| 7309 | 7308 | | T-T/C | |
| 7389 | 7388 | | T-T/C | |
| 7406.1 | 7405.1 | INS C | | |
| 7407 | 7406 | T-C | T-T/C | |
| 7412 | 7411 | | | (C/T)/(C/T) |
| 7476 | 7475 | | T-T/C | |
| 7521 | 7520 | | G-G/A | |
| 7756 | 7755 | | C-C/T | |
| 7763 | 7762 | | G-G/A | |
| 7768 | 7767 | G-A | A-A/G | |
| 7815 | 7814 | | C-C/T | |
| 7867 | 7866 | | C-C/T | |
| 7897 | 7896 | G-A | | |
| 8027 | 8026 | G-A | | |
| 8065 | 8064 | | | G/A-G |
| 8117 | 8116 | | C-C/T | |
| 8133 | 8132 | | C-C/T | |
| 8248 | 8247 | | A-A/G | |
| 8270 | 8269 | C-T | C-C/T | |
| 8426.1 | 8425.1 | INS G | | |
| 8468 | 8467 | | C-C/T | |
| 8616 | 8615 | | A-A/G | |
| 8655 | 8654 | | C-C/T | |
| 8697 | 8696 | G-A | G-G/A | |
| 8701 | 8700 | | A-A/G | |
| 8718 | 8717 | A-G | | |
| 8818 | 8817 | | T-T/C | |
| 8893 | 8892 | A-T | | |
| 8903 | 8902 | | C-C/T | |
| 9055 | 9054 | A-G | | |
| 9093 | 9092 | | G-G/A | |
| 9132 | 9131 | A-G | | |
| 9163 | 9162 | A-G | A-A/G | |
| 9313 | 9312 | | A-A/G | |
| | | | A-A/C | |
| 9327 | 9326 | | A-A/G | |
| 9352 | 9351 | | C-C/T | |

TABLE 4-continued

Base Mutations: Observed mutations of homoplasmic to homoplasmic, homoplasmic to heteroplasmic, and heteroplasmic to homoplasmic

| BP Historical Numbering** | BP eliminating position gap at 3106 | Homo-Homo | Homo-Hetero | Hetero-Homo |
|---|---|---|---|---|
| 9405 | 9404 | | T-T/C | |
| 9413 | 9412 | | T-T/C | |
| 9419 | 9418 | | C-C/T | |
| 9445 | 9444 | | G-G/A | |
| 9477 | 9476 | G-A | G-G/A | |
| 9502 | 9501 | G-A | | |
| 9540 | 9539 | | C-C/T | |
| 9548 | 9547 | A-G | | |
| 9554 | 9553 | | G-G/A | |
| 9559 | 9558 | | C-C/T | |
| 9564 | 9563 | | G-G/A | |
| 9574 | 9573 | | C-C/T | |
| 9591 | 9590 | | G-G/C | |
| 9628 | 9627 | | G-G/A | |
| 9667 | 9666 | G-A | | |
| 9696 | 9695 | | C-C/T | |
| 9698 | 9697 | C-T | C-C/T | |
| 9716 | 9715 | C-T | | |
| 9767 | 9766 | C-T | | |
| 9778 | 9777 | | G-G/A | |
| 9899 | 9898 | C-T | | |
| 10143 | 10142 | A-G | | |
| 10295 | 10294 | | G-G/A | |
| 10345 | 10344 | | T-T/C | |
| 10355 | 10354 | | C-C/T | |
| 10439 | 10438 | | C-C/T | |
| 10455 | 10454 | | G-G/A | |
| 10463 | 10462 | T-C | T-T/C | |
| 10550 | 10549 | | G-G/A | |
| 10679 | 10678 | G-A | | |
| 10685 | 10684 | | A-A/G | |
| 10688 | 10687 | | G-G/A | |
| 10754 | 10753 | A-C | | |
| 10810 | 10809 | T-C | T-T/C | |
| 10819 | 10818 | | G-G/A | |
| 10873 | 10872 | | C-C/T | |
| | | T-C | T-T/C | |
| 10882 | 10881 | C-T | | |
| 10885 | 10884 | C-T | | |
| 10944 | 10943 | | C-C/T | |
| 10956 | 10955 | | X-C/T | |
| 10972 | 10971 | G-A | G-G/A | |
| 10975 | 10974 | | C-C/T | |
| 10978 | 10977 | | A-A/G | |
| 9667 | 9666 | G-A | | |
| 9696 | 9695 | | C-C/T | |
| 9698 | 9697 | C-T | C-C/T | |
| 9716 | 9715 | C-T | | |
| 9767 | 9766 | C-T | | |
| 9778 | 9777 | | G-G/A | |
| 9899 | 9898 | C-T | | |
| 10143 | 10142 | A-G | | |
| 10295 | 10294 | | G-G/A | |
| 10345 | 10344 | | T-T/C | |
| 10355 | 10354 | | C-C/T | |
| 10439 | 10438 | | C-C/T | |
| 10455 | 10454 | | G-G/A | |
| 10463 | 10462 | T-C | T-T/C | |
| 10550 | 10549 | | G-G/A | |
| 10679 | 10678 | G-A | | |
| 10685 | 10684 | | A-A/G | |
| 10688 | 10687 | | G-G/A | |
| 10754 | 10753 | A-C | | |
| 10810 | 10809 | T-C | T-T/C | |
| 10819 | 10818 | | G-G/A | |
| 10873 | 10872 | | C-C/T | |
| | | T-C | T-T/C | |
| 10882 | 10881 | C-T | | |
| 10885 | 10884 | C-T | | |
| 10944 | 10943 | | C-C/T | |
| 10956 | 10955 | | X-C/T | |
| 10972 | 10971 | G-A | G-G/A | |
| 10975 | 10974 | | C-C/T | |
| 10978 | 10977 | | A-A/G | |
| 11001 | 11000 | | A-A/G | |
| 11013 | 11012 | | X-C/T | |
| 11024 | 11023 | | T-T/C | |
| | | | C-C/T | |
| 11069 | 11068 | | A-A/G | |
| 11084 | 11083 | | A-A/G | |
| 11113 | 11112 | T-C | T-T/C | |
| 11177 | 11176 | | C-C/T | |
| 11180 | 11179 | | G-G/T | |
| 11195 | 11194 | | G-G/A | |
| 11217 | 11216 | | C-C/T | |
| 11251 | 11250 | A-G | A-A/G | |
| | | G-A | G-G/A | |
| 11299 | 11298 | C-T | C-C/T | |
| 11332 | 11331 | | T-T/C | |
| 11337 | 11336 | | G-A/G | |
| 11351 | 11350 | | G-A/G | |
| 11356 | 11355 | | T-T/C | |
| 11377 | 11376 | | A-A/G | |
| 11420 | 11419 | | G-G/A | |
| 11647 | 11646 | C-T | | |
| 11719 | 11718 | G-A | G-G/A | |
| 11812 | 11811 | A-G | A-A/G | |
| 11852 | 11851 | | G-G/A | |
| 11857 | 11856 | | C-C/T | |
| 11864 | 11863 | C-T | C-C/T | |
| 11881 | 11880 | | C-C/T | |
| 11907 | 11906 | | T-T/C | |
| 11914 | 11913 | | G-G/A | |
| 12012 | 12011 | | C-C/T | |
| 12013 | 12012 | | | A/G-A |
| 12308 | 12307 | | G-G/A | |
| 12372 | 12371 | | G-G/A | |
| | | | A-A/G | |
| 12492 | 12491 | | T-T/A | |
| 12624 | 12623 | C-T | | |
| 12633 | 12632 | A-C | A-A/C | |
| 12654 | 12653 | | G-G/A | |
| 12810 | 12809 | | G-G/A | |
| 12959 | 12958 | | C-C/T | |
| 13079 | 13078 | | | A/G-A |
| 13089 | 13088 | T-A | | |
| 13105 | 13104 | | A-A/G | |
| 13111 | 13110 | T-C | | |
| 13212 | 13211 | | C-C/T | |
| 13281 | 13280 | | T-T/C | |
| 13294 | 13293 | | A-A/G | |
| 13359 | 13358 | | G-G/A | |
| 13368 | 13367 | G-A | G-G/A | |
| | | A-G | A-A/G | |
| 13398 | 13397 | | A-A/G | |
| 13431 | 13430 | | C-C/T | |
| 13436 | 13435 | | C-C/T | |
| 13468 | 13467 | | C-C/T | |
| 13476 | 13475 | | A-A/G | |
| 13484 | 13483 | | T-T/C | |
| 13487 | 13486 | | C-C/T | |
| 13506 | 13505 | | C-C/T | |
| 13530 | 13529 | | C-C/T | |
| 13536 | 13535 | | C-C/T | |
| 13563 | 13562 | | A-A/G | |
| 13573 | 13572 | | C-C/T | |
| 13579 | 13578 | G-A | | |
| 13609 | 13608 | | C-C/T | |
| | | | T-T/C | |
| 13617 | 13616 | C-T | C-C/T | |
| | | T-C | T-T/C | |
| 13634 | 13633 | | G-G/A | |
| 13650 | 13649 | | C-C/T | |
| 13621 | 13620 | | | T/C-C |

TABLE 4-continued

Base Mutations: Observed mutations of homoplasmic to homoplasmic, homoplasmic to heteroplasmic, and heteroplasmic to homoplasmic

| BP Historical Numbering** | BP eliminating position gap at 3106 | Homo-Homo | Homo-Hetero | Hetero-Homo |
|---|---|---|---|---|
| 13631 | 13630 | | C-C/T | |
| 13637 | 13636 | | G-G/A | |
| 13638 | 13637 | | A-A/G | |
| 13651 | 13650 | | A-A/G | |
| 13655 | 13654 | | T-T/C | |
| 13674 | 13673 | C-T | | |
| 13674 | 13673 | DEL C | | |
| 13680 | 13679 | | T-T/C | |
| 13687 | 13686 | | C-C/T | |
| 13707 | 13706 | | G-G/A | |
| 13708 | 13707 | | A-A/G | |
| | | | G-G/A | |
| 13711 | 13710 | | G-G/A | |
| 13712 | 13711 | | C-C/T | |
| 13725 | 13724 | | C-C/T | |
| 13731 | 13730 | | A-A/G | |
| 13734 | 13733 | | C-C/T | |
| 13743 | 13742 | | T-T/C | |
| 13748 | 13747 | | A-A/G | |
| 13759 | 13758 | | G-G/A | |
| | | | A-A/G | |
| 13766 | 13765 | | C-C/T | |
| 13788 | 13787 | | C-C/T | |
| 13789 | 13788 | | T-T/C | |
| 13805 | 13804 | | C-C/T | |
| 13841 | 13840 | | T-T/C | |
| 13880 | 13879 | | C-C/A | |
| 13888 | 13887 | X-T | X-C/T | |
| 13911 | 13910 | | G-G/A | |
| 13933 | 13932 | | A-A/G | |
| 14025 | 14024 | | C-C/T | |
| 14044 | 14043 | | C-C/T | |
| 14135 | 14134 | | T-T/A | |
| 14139 | 14138 | | G-G/A | |
| 14167 | 14166 | | T-T/C | |
| 14178 | 14177 | | T-T/C | |
| 14182 | 14181 | T-C | T-T/C | |
| 14203 | 14202 | | A-A/G | |
| 14220 | 14219 | X-G | X-G/A | |
| 14233 | 14232 | A-G | A-A/G | |
| 14281 | 14280 | T-C | T-T/C | |
| | | | C-C/T | |
| 14899 | 14898 | | G-G/A | |
| 14903 | 14902 | G-A | X-A/G | |
| 14918 | 14917 | | G-G/A | |
| 15043 | 15042 | | G-G/A | |
| 15115 | 15114 | | T-T/C | |
| 15162 | 15161 | | C-C/T | |
| 15218 | 15217 | G-A | G-G/A | |
| 15244 | 15243 | | G-G/A | |
| 15265 | 15264 | | C-C/T | |
| 15286 | 15285 | | C-C/T | |
| 15301 | 15300 | | A-A/G | |
| 15302 | 15301 | | C-C/T | |
| 15307 | 15306 | | C-C/T | |
| 15323 | 15322 | A-G | A-A/G | |
| | | | G-G/A | |
| 15324 | 15323 | | C-C/T | |
| 15343 | 15342 | X-C | X-C/T | |
| 15355 | 15354 | X-A | X-A/G | |
| 15379 | 15378 | | C-C/T | |
| 15384 | 15383 | X-C | X-C/T | |
| 15429 | 15428 | | A-A/G | |
| 15452 | 15451 | C-A | C-C/A | |
| | | A-C | A-A/C | |
| 15523 | 15522 | | C-C/T | |
| 15525 | 15524 | | G-G/A | |
| 15526 | 15525 | | C-C/T | |
| 15527 | 15526 | | C-C/T | |
| 15557 | 15556 | | G-G/A | |
| 15587 | 15586 | | C-C/T | |
| 15607 | 15606 | A-G | A-A/G | |
| | | G-A | G-G/A | |
| 15670 | 15669 | | C-C/T | |
| 15693 | 15692 | C-T | C-C/T | |
| 15698 | 15697 | | C-C/T | |
| 15704 | 15703 | | C-C/A | |
| 15708 | 15707 | | G-G/T | |
| 15762 | 15761 | | G-G/A | |
| 15812 | 15811 | | A-A/G | |
| 15826.1 | 15825.1 | INS G | | |
| 15834 | 15833 | | T-T/C | |
| 15865 | 15864 | | A-A/G | |
| 15884 | 15883 | C-G | G-C/G | |
| 15889 | 15888 | | T-T/C | |
| 15904 | 15903 | T-C | T-T/C | |
| | | | C-A/C | |
| 15907 | 15906 | | G-G/A | |
| 15927 | 15926 | A-G | | |
| 15928 | 15927 | A-G | A-A/G | |
| | | G-A | G-G/A | |
| 15998 | 15997 | | | A/T-A |
| 15999.1 | 15998.1 | INS T | | |
| 16048 | 16047 | | G-G/A | |
| 16051 | 16050 | | A-A/G | |
| | | | G-G/A | |
| 16063 | 16062 | | C-C/T | |
| 16067 | 16066 | | C-C/T | |
| 16069 | 16068 | | C-C/T | |
| 16093 | 16092 | X-C | T-T/C | |
| | | C-T | C-C/T | |
| 16095 | 16094 | C-T | C-C/T | |
| 16111 | 16110 | | T-T/C | |
| 16126 | 16125 | T-C | T-T/C | |
| | | | C-C/T | |
| 16129 | 16128 | G-A | G-G/A | |
| 16134 | 16133 | | C-C/T | |
| 16148 | 16147 | | C-C/T | |
| 16153 | 16152 | | A-A/G | |
| 16163 | 16162 | | G-G/A | |
| 16172 | 16171 | | C-C/T | |
| 16184 | 16183 | C-T | C-C/T | |
| | | T-C | | |
| 16186 | 16185 | | T-T/C | |
| 16189 | 16188 | T-C | T-T/C | |
| | | C-T | C-C/T | |
| 16190 | 16189 | T-C | | |
| 16192 | 16191 | | C-C/T | |
| | | T-C | T-T/C | |
| 16209 | 16208 | | C-C/T | |
| | | | T-T/C | |
| 16223 | 16222 | | T-T/C | |
| | | C-T | | |
| 16224 | 16223 | C-T | C-C/T | |
| | | | T-T/C | |
| 16225 | 16224 | C-T | | |
| 16235 | 16234 | | A-A/G | |
| 16239 | 16238 | C-T | C-C/T | |
| | | X-C | | |
| 16247 | 16246 | | G-G/A | |
| 16256 | 16255 | | T-T/C | |
| | | | C-C/T | |
| 16270 | 16269 | C-T | C-C/T | |
| 16292 | 16291 | | C-C/T | |
| 16294 | 16293 | C-T | C-C/T | |
| | | | A-A/G | |
| 16270 | 16269 | T-C | T-T/C | |
| | | | C-C/T | |
| 16278 | 16277 | T-C | | |
| 16280 | 16279 | | A-A/G | A/G-A |
| 16290 | 16289 | | C-C/T | |
| | | | T-T/C | |
| 16291 | 16290 | | C-C/T | |
| 16292 | 16291 | | T-T/C | |

TABLE 4-continued

Base Mutations: Observed mutations of homoplasmic to homoplasmic, homoplasmic to heteroplasmic, and heteroplasmic to homoplasmic

| BP Historical Numbering** | BP eliminating position gap at 3106 | Homo-Homo | Homo-Hetero | Hetero-Homo |
|---|---|---|---|---|
| 16293 | 16292 | | A-A/G | |
| 16294 | 16293 | | T-T/C | |
| | | C-T | C-C/T | |
| 16295 | 16294 | | C-C/T | |
| 16296 | 16295 | C-T | C-C/T | |
| | | | T-T/C | |
| 16298 | 16297 | C-T | C-C/T | |
| 16303 | 16302 | | G-G/T | |
| 16304 | 16303 | | T-T/C | |
| | | C-T | C-C/T | |
| 16311 | 16310 | C-T | C-C/T | |
| | | T-C | T-T/C | |
| 16319 | 16318 | G-A | G-G/A | |
| | | | T-T/C | |
| | | | A-A/G | |
| 16320 | 16319 | | T-T/C | |
| 16325 | 16324 | | C-C/T | |
| 16344 | 16343 | C-G | | |
| 16356 | 16355 | | C-C/T | |
| 16342 | 16341 | C-T | C-C/T | |
| 16352 | 16351 | | T-T/C | |
| 16353 | 16352 | | C-C/T | |
| 16354 | 16353 | | T-T/C | |
| 16355 | 16354 | | T-T/C | |
| 16359.1 | 16358.1 | INS G | | |
| 16360 | 16359 | | C-C/T | |
| 16362 | 16361 | | C-C/T | |
| | | | T-T/C | |
| 16370 | 16369 | | G-G/A | |
| 16389 | 16388 | | G-G/A | |
| 16390 | 16389 | X-G | X-G/A | |
| 16398 | 16397 | A-G | | G/A-G |
| 16399 | 16398 | G-A | | G/A-A |
| 16429 | 16428 | | X-T/C | |
| 16465 | 16464 | C-T | C-C/T | |
| | | T-C | T-T/C | |
| 16475 | 16474 | | T-T/C | |
| 16514 | 16513 | | C-C/T | |
| 16519 | 16518 | T-C | T-T/C | |
| | | C-T | C-C/T | |
| 16526 | 16525 | A-G | | |
| | | | G-G/A | |
| 16527 | 16526 | | C-C/T | |
| 16537 | 16536 | T-C | T-T/C | |
| 16296 | 16295 | C-T | C-C/T | |
| 16544 | 16543 | | T-T/C | |

* The first nucleotide represents the normal nucleotide, followed by the mutated nucleotide; separated by an "-".
* When no blood is present, it is denoted as an "X".
**Historical numbering wherein deletion at BP 3106 is denoted as a gap and the rare polymorphism 750A has been retained

TABLE 5

| SEQ ID NO: | Primer | Length (# bases) | 5'-3' |
|---|---|---|---|

D-Loop Primers (used for formalin fixed tissue and blood for needle biopsies)

| 19 | 15971f | 20 | TTAACTCCACCATTAGCACC |
| 20 | 15f | 20 | CACCCTATTAACCACTCACG |
| 21 | 16211f | 22 | CAGCAATCAACCCTCAACTATC |
| 22 | 16410r | 19 | AGGATGGTGGTCAAGGGAC |
| 23 | 389r | 20 | CCTAACACCAGCCTAACCAG |
| 24 | 420r | 18 | GTGCATACCGCCAAAGA |
| 25 | 711r | 21 | AACGGGGATGCTTGCATGTGT |

Formalin Fixed Tissue Primers (used for 31 prostatectomies)

| 26 | 649f | 21 | TAGGTTTGGTCCTAGCCTTTC |
| 27 | 1051f | 26 | ACAATAGCTAAGACCCAAACTGGGAT |
| 28 | 1247r | 22 | CAAGAGGTGGTGAGGTTGATCG |
| 29 | 8959r | 22 | CGATAATAACTAGTATGGGGAT |
| 30 | 8814f | 22 | CCAACTATCTATAAACCTAGCC |
| 31 | 9247f | 19 | GCCCATGACCCCTAACAGG |
| 32 | 9868r | 21 | CGGATGAAGCAGATAGTGAGG |
| 33 | 9711f | 22 | CTGGGTCTCTATTTTACCCTCC |
| 34 | 10663f | 18 | TCTTTGCCGCCTGCGAAG |
| 35 | 10766r | 22 | TTAGCATTGGAGTAGGTTTAGG |
| 36 | 11813r | 26 | GTAGAGTTTGAAGTCCTTGAGAGAGG |
| 37 | 11629f | 23 | AATCAGCCACATAGCCCTCGTAG |
| 38 | 12709r | 28 | GGAAGATGAGTAGATATTTGAAGAACTG |
| 39 | 12528f | 22 | GAACTGACACTGAGCCACAACC |
| 40 | 13516r | 23 | GGTCTTTGGAGTAGAAACCTGTG |
| 41 | 13239f | 23 | CGTAGCCTTCTCCACTTCAAGTC |
| 42 | 15351r | 23 | TCGTGCAAGAATAGGAGGTGGAG |
| 43 | 15144f | 25 | TCCCGTGAGGCCAAATATCATTCTG |
| 44 | 6145r | 24 | CAGTTGCCAAAGCCTCCGATTATG |
| 45 | 5867f | 25 | CAATGCTTCACTCAGCCATTTTACC |
| 46 | 13957r | 22 | CTAGATAGGGGATTGTGCGGTG |
| 47 | 13838f | 23 | CCCTAGACCTCAACTACCTAACC |
| 48 | 15026r | 21 | GGCAGATAAAGAATATTGAGG |
| 49 | 14937f | 22 | CATCAATCGCCCACATCACTCG |
| 50 | 1938f | 24 | AGAGCACACCCGTCTATGTAGCAA |
| 51 | 2084r | 26 | TACAAGGGGATTTAGAGGGTTCTGTG |
| 52 | 2973f | 24 | TAGGGTTTACGACCTCGATGTTGG |
| 53 | 3101r | 24 | TAGAAACCGACCTGGATTACTCCG |
| 54 | 3728f | 23 | CATATGAAGTCACCCTAGCCATC |
| 55 | 3893r | 23 | GTTCGGTTGGTCTCTGCTAGTGT |
| 56 | 4888f | 27 | CAATCATATACCAAAATCTCTCCCTCAC |
| 57 | 5035r | 25 | CATCCTATGTGGGTAATTGAGGAGT |
| 58 | 5981f | 23 | TGGAGTCCTAGGCACAGCTCTAA |
| 59 | 6154r | 24 | GGAACTAGTCAGTTGCCAAAGCCT |
| 60 | 6911r | 24 | TGCAGTGCTCTGAGCCCTAGGATT |
| 61 | 7082r | 26 | GAAGCCTCCTATGATGGCAAATACAG |
| 62 | 7829f | 25 | CGCATCCTTTACATAACAGACGAGG |
| 63 | 8029r | 24 | GGCTTCAATCGGGAGTACTACTCG |

Blood Primers (prostatectomy)

| 64 | 16485f | 24 | GAACTGTATCCGACATCTGGTTCC |
| 65 | 919r | 22 | TTGGGTTAATCGTGTGACCGCG |
| 66 | 1644r | 26 | CTCCTAAGTGTAAGTTGGGTGCTTTG |
| 67 | 615f | 24 | ATGTTTAGACGGGCTCACATCACC |
| 68 | 1488f | 24 | CGTCACCCTCCTCAAGTATACTTC |
| 69 | 2612r | 28 | GGAACAAGTGATTATGCTACCTTTGCAC |
| 70 | 2417f | 23 | CACTGTCAACCCAACACAGGCAT |
| 71 | 3641r | 23 | GCTAGGCTAGAGGTGGCTAGAAT |
| 72 | 3230f | 23 | GTTAAGATGGCAGAGCCCGGTAA |
| 73 | 4417r | 26 | TTTAGCTGACCTTACTTTAGGATGGG |
| 74 | 4337f | 24 | ATGAGAATCGAACCCATCCCTGAG |
| 75 | 5551r | 24 | GGCTTTGAAGGCTCTTGGTCTGTA |
| 76 | 6418f | 23 | AACCCCCTGCCATAACCCAATAC |
| 77 | 7554r | 33 | CTTTGACAAAGTTATGAAATGGTTTTTCTAATA |
| 78 | 7400f | 22 | CCCACCCTACCACACATTCGAA |
| 79 | 8441r | 26 | GTTGGGTGATGAGGAATAGTGTAAGG |
| 80 | 8346f | 26 | CAACACCTCTTTACAGTGAAATGCCC |
| 81 | 9413r | 24 | GCCTTGGTATGTGCTTTCTCGTGT |
| 82 | 10285r | 21 | GGTAGGGGTAAAAGGAGGGCA |
| 83 | 9273r | 21 | TCAGCCCTCCTAATGACCTCC |
| 84 | 10198f | 19 | CCCGCGTCCCTTTCTCCAT |
| 85 | 11408r | 25 | GGAGTCATAAGTGGAGTCCGTAAAG |
| 86 | 11210f | 24 | TTCTACACCCTAGTAGGCTCCCTT |
| 87 | 12231r | 26 | GTTAGCAGTTCTTGTGAGCTTTCTCG |
| 88 | 12096f | 22 | TCCTATCCCTCAACCCCGACAT |
| 89 | 13098r | 26 | CAACTATAGTGCTTGAGTGGAGTAGG |
| 90 | 12881f | 26 | CATCCTCGCCTTAGCATGATTTATCC |
| 91 | 13851r | 24 | GTTGAGGTCTAGGGCTGTTAGAAG |
| 92 | 14738f | 24 | AGAACACCAATGACCCCAATACGC |
| 93 | 15731r | 28 | CTAGGAGTCAATAAAGTGATTGGCTTAG |
| 94 | 15347f | 23 | CACGAAACGGGATCAAACAACCC |
| 95 | 16000r | 24 | CTTAGCTTTGGGTGCTAATGGTGG |
| 96 | 5544f | 21 | CACGCTACTCCTACCTATCTC |

TABLE 5-continued

| SEQ ID NO: | Primer | Length (# bases) | 5'-3' |
|---|---|---|---|
| 97 | 6482r | 20 | GACTGCTGTGATTAGGACGG |
| 98 | 13354f | 23 | TTTATGTGCTCCGGGTCCATCAT |
| 99 | 14458r | 22 | GATGGCTATTGAGGAGTATCCT |
| 100 | 14399f | 21 | ACACTCACCAAGACCTCAACC |
| 101 | 15593r | 23 | ATCGGAGAATTGTGTAGGCGAAT |

Example 10

3.4 kb Deletion in the mtDNA of Prostate Tissue

Figure 5:
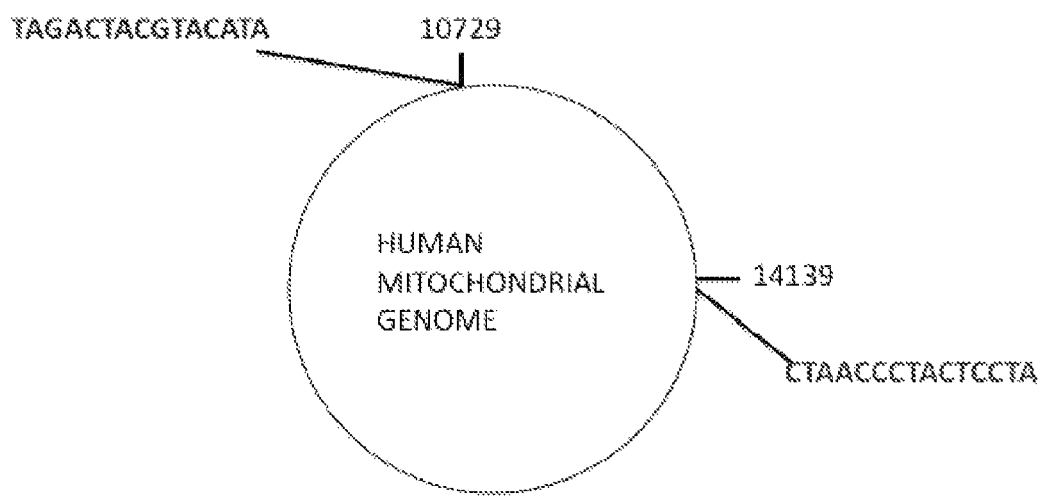
FIG. 5 is a schematic diagram showing the design and sequence of a primer (SEQ ID NO. 139) useful for the detection of the 3.4 kb deletion.

A deletion of approximately 3.4 kilobase (kb) was identified through full mitochondrial genome amplification of fresh frozen prostate tissue. Using linear regression, the size of the deletion was estimated to be between 3000 base pairs (bp) and 3500 bp. Two possible candidate deletions were identified using Mitomap (Brandon, M. C., Lott, M. T., Nguyen, K. C., Spolim, S., Navathe, S. B., Baldi, P. & Wallace, D. C. MITOMAP: a human mitochondrial genome database—2004 update. Nucleic Acids Research 33 (Database Issue):D611-613, 2005; www.mitomap.org), the 3397 bp deletion at 9574-12972, and the 3379 bp deletion at 10744-14124. In order to determine which of the two deletions was correct, if either, a forward primer which bridged the deletion junction was developed for each of the two candidates, ensuring that the primer extended further than the repeat regions that flank the deletions. FIG. 5 is a schematic diagram showing the design and sequence of the primer. Positive amplification results for the amplicon corresponding to the 3379 bp deletion (referred to as the 3.4 kb deletion) at 10744-14124 were obtained.

The deletion removes all or part of the following genes: (i) NADH dehydrogenase subunit 4L, (ii) NADH dehydrogenase subunit 4, (iii) NADH dehydrogenase subunit 5, (iv) tRNA histidine, (v) tRNA serine2, and (vi) tRNA leucine2.

The 3.4 kb deletion was determined to be present in 91% of 33 fresh frozen prostate samples. With the specific deletion primers, formalin fixed tissues were tested in order increase the n value.

Previously, the present investigators sequenced entire mitochondrial genomes from 32 tissue samples microdissected by LCM and 12 needle biopsies from histologically normal prostates. Archived tissue sections from each of these samples were used for the following study. 1-2 serial sections were removed from each sample. DNA was extracted from each sample in its entirety rather than as a microdissection. Thus, each sample consisted of a mixture of glandular prostate tissue as well as stromal prostate tissue. This extraction was performed using Qiagen's QIAamp DNA Mini Kit (Cat # 51304). Following extraction the samples were quantified using a Nano-Drop spectrophotometer and the concentrations were subsequently normalized to 2 ng/ul. Each sample was amplified using 20 ng input DNA and an iQ™ SYBR Green Supermix kit (Bio-Rad Laboratories Inc.) Reactions were run on an Opticon® 2 (MJ Research).

Figure 6:
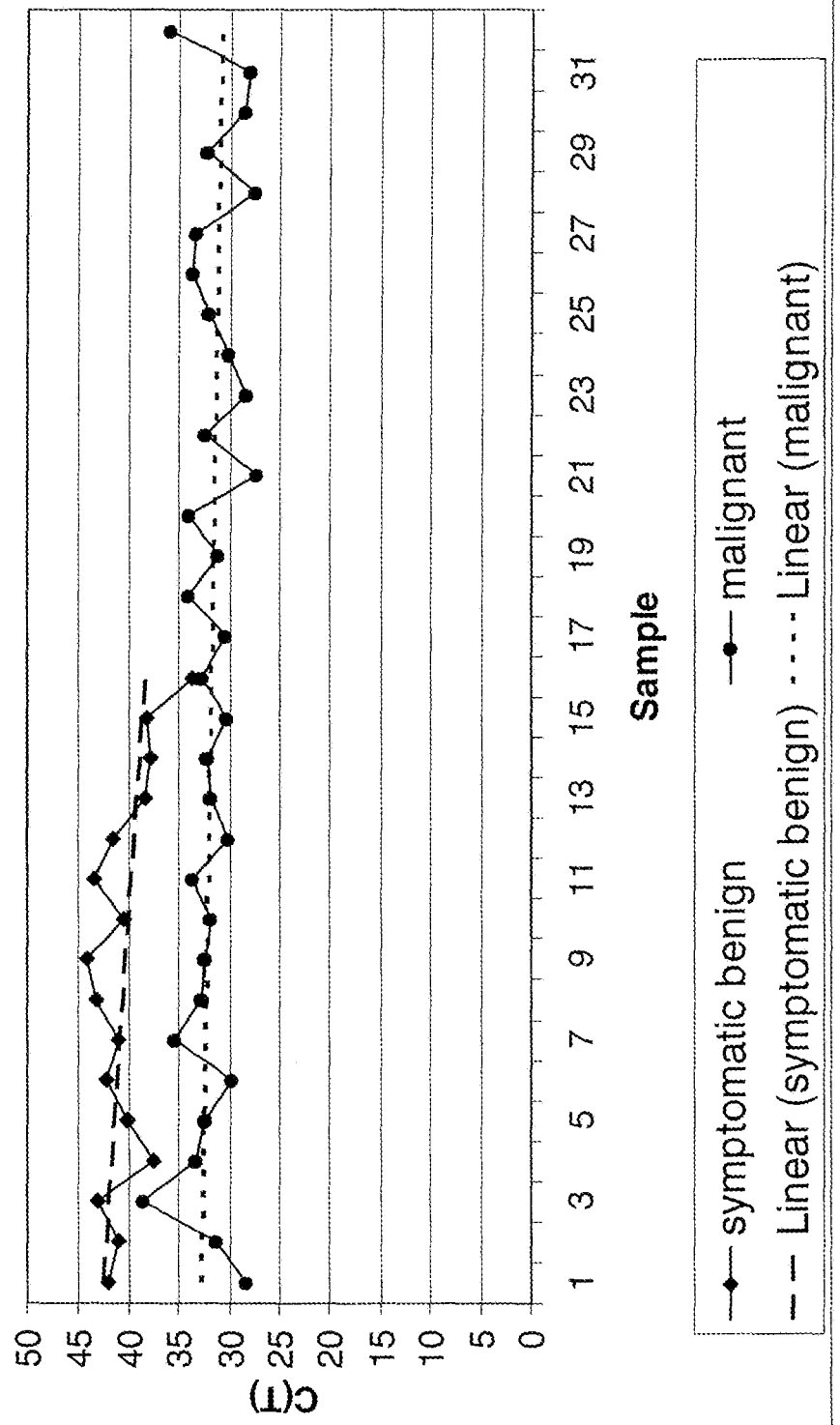
FIG. 6 is a graph showing a comparison of cycle threshold between malignant and symptomatic benign participants in the 3.4 kb study.

As shown in FIG. 6, a distinct difference was observed in cycle threshold and, by extension, quantity of the deletion between the malignant prostate samples and the symptomatic benign prostate samples. Malignant samples exhibited a consistently earlier cycle threshold than the benign samples.

Example 11

3.4 kb Deletion Blinded Study

Comparison of Cycle Threshold

Following the study described in Example 10, an additional 21 samples were selected, 10 of which were benign and 11 of which were malignant. The pathological status was determined by needle biopsies conducted by a qualified pathologist. The samples were blinded such that the present investigators were unaware of their pathological status when they conducted this test. The present investigators were able to predict pathological status correctly in 81% of the cases by examining the cycle threshold. Of the 4 incorrect calls, two were malignant samples that were determined to be benign and 2 were benign samples that were determined to be malignant. Follow-up clinical information for the 2 individuals in the latter scenario was requested from the physician to determine if they had been diagnosed with prostate cancer subsequent to the needle biopsy results used for this study. One of the individuals who originally produced a benign sample but was predicted by this study to have a malignancy subsequently produced a malignant sample. As a result, one of the false positives became a true positive. Therefore, pathological status was predicted correctly in 86% of the cases examined in this study. The ultimate positive predictice value (PPV, where PPV=true positives/(true positives+false positives)) for this study was 91% and the negative predictive value (NPV, where NPV=true negatives/(true negatives+false negatives)) was 80%.

Example 12

3.4 kb Deletion Study

Methods (n=76)

Archived Samples

Seventy-six prostate tissues were examined for the 3.4 kb deletion in this study. All tissue samples were formalin-fixed, 25 being malignant, 12 being normal, and 39 having benign prostatic disease as shown histologically. Of the latter group more then half had hyperplasia. All specimens were needle biopsies taken from the investigators' tissue archives.

Prostate Specimens

A tapelift was performed on each slide using Prep-Strips (Catalogue Number LCM0207) from Arcturus Bioscience Inc. This allowed the removal of any particulate matter or non-adhering tissue from the slide prior to DNA extraction. With the tissue still on the slides, the slides were rinsed with PBS (Phosphate Buffered Saline Solution) to remove as much fixative as possible. The 1-2 needle biopsy sections on the slides were scraped into sterile microcentrifuge tubes using individually wrapped, sterilized surgical razor blades. DNA was then isolated and purified using a QIAamp® DNA Mini Kit (Qiagen, Cat. # 51304) according to manufacturer's specifications. A negative extract control was processed in parallel with the slide extractions as a quality control checkpoint. The total concentration of DNA and purity ratio for each sample was determined by spectrophotometry (Nano-Drop ND-1000) and dilutions of 2 ng/µl were prepared for the purpose of Quantitative Polymerase Chain Reaction (qPCR).

Primers (Oligonucleotides)

Purified oligonucleotide primers were chemically synthesized by Invitrogen (California, USA). The sequences of the primers and the expected sizes of the PCR products amplified are listed in Table 6. In addition, PCR analysis for mtDNA deletions included positive controls (DNA from a source known to carry the mutant mtDNA). Each primer set with the exception of TNF were checked against a mitochondria-free rho 0 cell line to confirm the absence of pseudogene coamplification.

TABLE 6

Amplification Primers.

| Primer Pair | Position Amplified 5'-3' | Length of amplified product (base pairs) |
|---|---|---|
| 3.4 Deletion Real-Time | 10729-14379 (less 3379 bp at 10744-14124) | 273 |
| 12s mtDNA | 708-945 | 238 |
| TNF | 3756-3886 | 131 |

3.4 forward (10729-10743-14125-14139)
5'TAGACTACGTACATACTAACCCTACTCCTA-3'    SEQ ID NO: 139

3.4 reverse (14361-14379)
5'-GAGGTAGGATTGGTGCTGT-3'    SEQ ID NO: 140

12s forward (708-728)
5'-CGTTCCAGTGAGTTCACCCTC-3"    SEQ ID NO: 141

12s reverse (923-945)
5'-CACTCTTTACGCCGGCTTCTATT-3'    SEQ ID NO: 142

TNF forward (3756-3775)
5'-CCTGCCCCAATCCCTTTATT-3'    SEQ ID NO: 143

TNF reverse (3866-3886)
5'-GGTTTCGAAGTGGTGGTCTTG-3'    SEQ ID NO: 144

For TNF primers, Primer Reference Eppendorf ® HotMaster ™ Application No. 1

HotMaster—An innovative Hot Start/Cold Stop Technology for Better PCR* Results
George Halley and Vincent Prezioso, PhD
George Halley, Eppendorf—5 Prime, Inc., Boulder, Colo., USA
Vincent Prezioso, Brinkmann Instruments, BioSytems Application Lab, Westbury, N.Y.
http://www.brinkmanncanada.com/applications/PCR_appl_hotmaster.asp
Real-Time Polymerase Chain Reaction Three separate PCRs were performed on each sample. Each reaction was 25 μl total volume and included template DNA, one pair of primers (12s or 3.4 Deletion or TNF), an iQ™ SYBR Green Supermix kit (Catalogue Number 170-8882, Bio-Rad Laboratories Inc.) and distilled deionized water (ddH$_2$O). The TNF (tumor necrosis factor) comprised single copy nuclear gene primers, and 12s comprised total mitochondrial genome primers. The volume and concentrations for template DNA, primers, and reaction buffer are listed below.

TABLE 7 qPCR Components.

| Reagent | Concentration per Reaction | Volume per Reaction |
|---|---|---|
| Reaction Buffer | 1X | 12.5 μl |
| Primer (forward and reverse) | 250 nM | 0.0625 μl of each 100 umole stock |
| ddH$_2$O | N/A | 2.375 μl |
| Template DNA | 20 ng | 10.0 μl |
| Total | | 25 μl |

The cycling parameters for each amplicon are listed in Table 8.

TABLE 8

Cycling Parameters.

| Step | Temperature (° C.) | Duration |
|---|---|---|
| 1 | 95 | 3 min |
| 2 | 95 | 30 sec |
| 3 | 66 (3.4 deletion primers) or 61.5 (12 s primers) or 61.5 (TNF primers) | 30 sec |
| 4 | 72 | 30 sec |
| 5 | Plate Read | |
| 6 | 72 | 10 min |
| 7 | Melting Curve 50° C.-110° C. reading every 1° C. | 3 sec |

Repeat steps 2-5, 44 times for a total of 45 cycles.

Analysis

Thermal cycling, real-time detection and analysis of the reactions was carried out using a DNA Engine Opticon® 2 Continuous Fluorescence Detection System equipped with Intuitive Opticon Monitor™ software (MJ Research Inc.). The standard curve method was utilized for DNA quantification. We performed a set of serial dilutions ($10^6$, $10^5$, $10^4$, $10^3$, $10^2$, $10^1$) of three purified PCR generated templates, one product for the 3.4 deletion, one for the 12s primers, and one for TNF. From this, three different standard curves were generated showing the number of copies of total mtDNA (12s amplicon-total mitochondrial genome primers), 3.4 deletion or total nuclear DNA (TNF-single copy nuclear gene primers). The $C_T$ values of the samples can then be converted to the number of DNA copies by comparing the sample $C_T$ to that of the standards. The 3.4 deletion was considered to be absent or at low levels if the deletion was not detected within 37 cycles.

The determination of malignancy is based upon the quantity of the 3.4 kb deletion present in the normalized sample as indicated by the location of the cycle threshold. This location may be either absolute, as in greater than 25 cycles but less than 35 cycles, or more likely a ratio between the total mitochondrial DNA present as indicated by the 12s amplicon, and the 3.4 kb deletion. This may be expressed as a percent of the total mitochondrial DNA. The number of cells, as represented by the TNF amplicon, may be incorporated to refine the distinction between benign and malignant tissues.

In order to automate the analyses of these samples, bioinformatics tools were employed. The three variables that are considered for these analyses are the cycle threshold $C_T$ of Tumour Necrosis Factor (TNF), total species of mitochondria that contain those specific primer sites, and those mitochondria that harbour the deletion of interest.

Cluster Analysis

The clustering was not normalized nor were logarithmic functions used due to the similar and small range of data.

Figure 7:
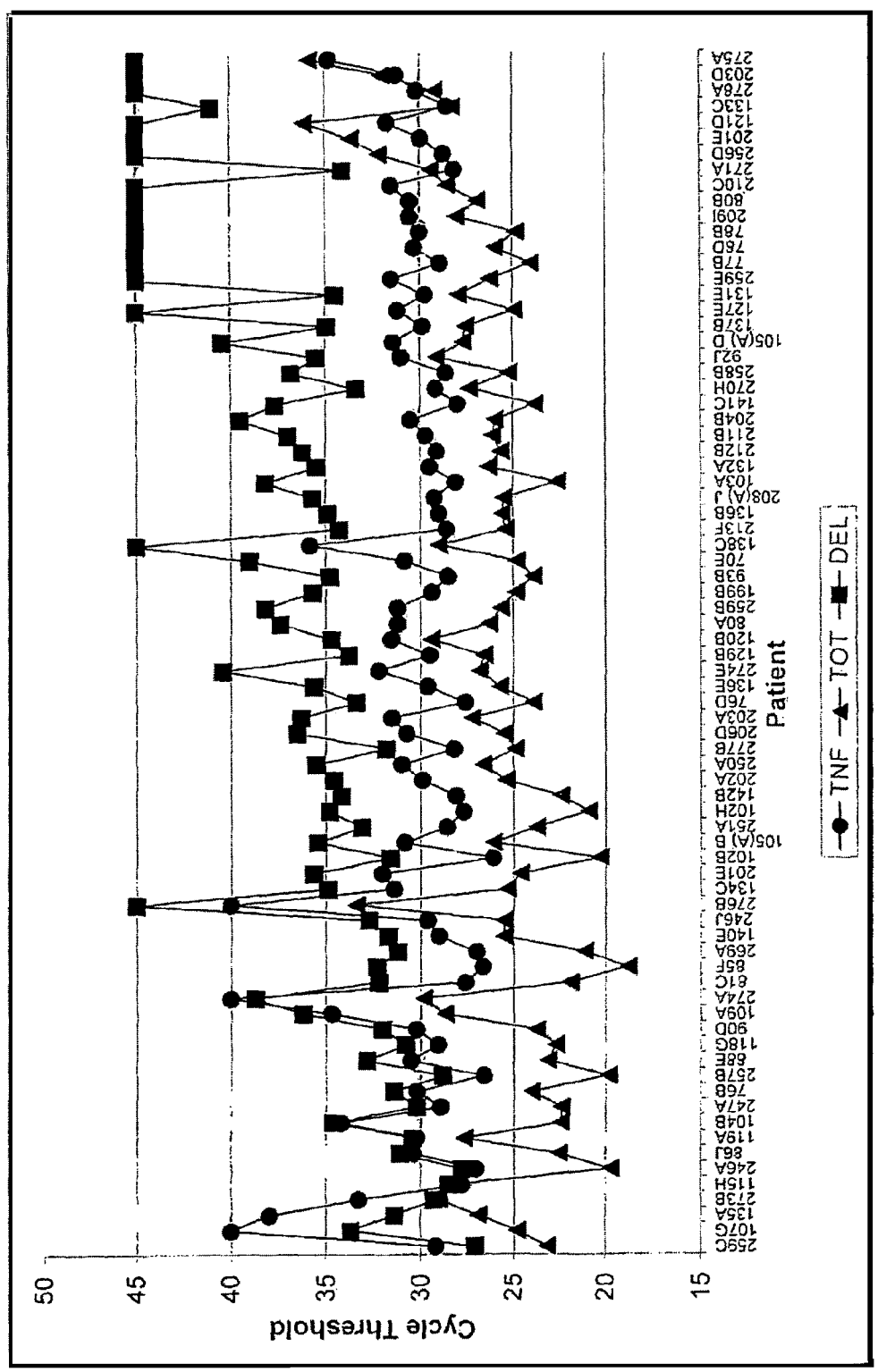
FIG. 7 is a graph showing cycle threshold as related to Example 12.

FIG. 7 shows the actual movement and trends of the data. The x-axis is the patient number and the y-axis is the cycle threshold obtained from real time PCR.

It is important to note that the higher the cycle threshold is, the lower amount of the variable is present.

The primary general trend shown in FIG. 7 is based upon the differences/ratios between the variables of Deletion, Total, and TNF. The deletion is low to absent for the benign/normal samples (right side) and increases (toward the left) with abnormal benign and malignant samples. The abnormal benign and malignant samples begin to differentiate themselves from each other based on the cycle threshold ratio of Deletion to TNF.

Supervised Learning

Supervised learning is based on the system trying to predict outcomes for known samples. Half of the data was used to train and the other half to test the algorithm. Supervised learning compares its predictions to the target answer and "learns" from its mistakes. But, if the predicted output is higher or lower than the actual outcome in the data, the error is propagated back through the system and the weights are adjusted accordingly.

Data SET:
- 5% to 35%—Benign
- 35% to 65%—Hyperplasia
- 65% to 95%—Malignant

ANN Algorithm (shown schematically below):
Half of Data set used for Training ANN
Other half used to compare the accuracy Accuracy=Compare expected data set with obtained data set→86.6%

Artificial Neural Network algorithm

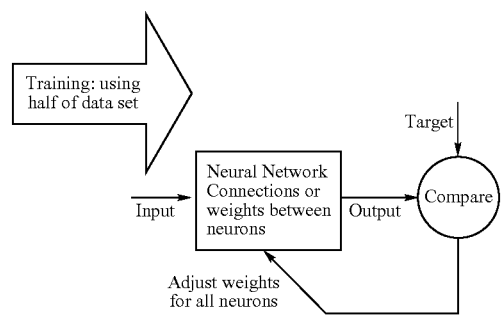

Supervised Learning of Deletion Data using Artificial Neural Network (ANN)
Three Classifications:
Benign
Hyperplasia
Malignant
Three variables for each classification are used based on Real Time PCR Cycle Threshold $C_T$:
Tumour Necrosis Factor (TNF)—Nuclear copy control.
Total Mitochondria—Mitochondria copy control
Deletion—Mitochondria in the deleted state.
Results:
Half of data set is used to train the ANN, and the remaining half is used to compare the accuracy.
Three Classification Accuracy=86.6%
Positive Predictive Value (PPV);
Benign to Malignant=88.2%
Negative Predictive Value (NPV)
Benign to Malignant=76.5%

Example 13

The Use of a 3895 bp Mitochondrial DNA Deletion as a Marker for Sunlight Exposure in Human Skin Since the initial discovery of the possible association of the 3895 bp deletion with sun exposure as reported by Harbottle et al., 2004 and Durham et al., 2003, further work has confirmed that the association is present. As well, the additional work has enabled the use of this deletion for a diagnostic test of sun exposure or skin cancer detection, through the invention of a novel method for detection of deletions and sequence rearrangements in a fully quantitative manner. This method provides for the annealing of a primer or probe to the newly formed sequence created by the deletion or insertion involved in the rearrangement and thereby allows the use of real-time quantitative PCR (qPCR) as a means of detection. The use of the qPCR platform enables the quantitative detection of the deletion rather than a simple presence and absence scenario. This quantitation is the basis of the test as it is the relative amounts of deletion that measures the level of sun exposure or the character of the malignancy rather than the simple presence or absence semi-quantitation previously reported. As well the qPCR platform enables the use of apparently unaffected or non-exposed tissue as the detection sensitivity is substantially greater than conventional PCR and ethidium bromide detection.

Background

The incidence of non-melanoma skin cancer (NMSC) is increasing in populations of European origin (Severi and English, 2004). For example, one million new cases are diagnosed each year in the USA (Wesson and Silverberg, 2003) and 65,000 in the UK (figures provided by Cancer Research. UK). NMSC accounts for around 90% of skin cancers and consists of basal cell and squamous cell carcinomas (BCC and SCC, respectively). BCC are the commonest form of NMSC and arise predominantly from the basal keratinocytes of the epidermis but also from cells in hair follicles and sebaceous glands. They are locally invasive but rarely metastasise. SCCs are also derived from basal keratinocytes; however, in contrast to BCC, SCC may metastasize. Compared with BCC, SCC shows the greatest increase with age and is concentrated in the elderly (Severi and English, 2004). The relative density of NMSC is highest on body sites "usually" exposed to the sun when outdoors such as scalp, face, neck, and ears as defined by Armstrong (2004). SCC, however, differs appreciably from BCC in having a much lower density on body sites which are "occasionally" exposed to the sun such as shoulders, back, and chest as defined by Armstrong (2004).

Therefore, the major determinant of NMSC is the ultraviolet radiation (UVR) component of sunlight that induces DNA damage. Importantly it is both the pattern (more continuous versus intermittent) and the cumulative amount of sun exposure that influences the development of NMSC (Armstrong and Kricker, 2001). To determine a reliable marker of cumulative UVR exposure in human skin, the inventors and others have examined the novel idea of using mitochondrial DNA (mtDNA), rather than nuclear DNA, as a biomarker of UV-induced DNA damage (Pang et al, 1994; Berneburg et al, 1997; Birch-Machin et al, 1998; Birch-Machin, 2000;). Compared with mutation screening of nuclear DNA genes such as p53, there are certain advantages of studying mtDNA damage in sun-exposed skin. First, although there is evidence in mitochondria for base excision repair of oxidative damage, there is no evidence of nuclear excision repair for the repair of DNA photoproducts (e.g. cyclobutane pyrimidine dimers) in mtDNA (LeDoux et al, 1993; Croteau and Bohr, 1997; Pascucci et al, 1997; Sawyer and Van Houten, 1999). Second, each cell can contain up to several thousand copies of the mtDNA genome and mitochondria can therefore tolerate very high levels (up to 90%) of damaged mtDNA through complementation of the remaining wild-type (Chomyn et al, 1992;

Sciacco et al, 1994). Together, these factors lead to accumulation of photodamage in mtDNA without compromising cell function.

The use of mtDNA damage as a biomarker for cumulative sun-exposure in human skin is a relatively new field of research and previous work has simply compared mtDNA damage to distinguish between sun-protected and sun-exposed skin (Pang et al, 1994; Berneburg et al, 1997; Birch-Machin et al, 1998). This approach is limited because NMSC is predominantly formed on body sites which are "usually" exposed to the sun when outdoors as opposed to sites that are "occasionally" exposed to the sun (Armstrong, 2004). In an attempt to address this limitation, the present example demonstrates that the frequency of occurrence of a rarely reported 3895 bp mtDNA deletion (only previously described in diseased muscle (Moraes et al, 1992)) is significantly different between body sites that are "usually" versus "occasionally" exposed to the sun. In addition, the example demonstrates the link between the etiology of the 3895 bp deletion with the UVR component of sunlight by inducing the 3895 bp deletion in vitro with repetitive sub-lethal doses of a UVA+UVB light source.

Methods and Materials

The ultraviolet radiation (UVR) in sunlight is widely recognized as the major determinant of non-melanoma skin cancer (NMSC) in Caucasian individuals. Previous work by the present inventors and others have examined the use of mitochondrial DNA (mtDNA) damage as a biomarker of cumulative sun exposure in human skin. These studies have compared mtDNA damage between sun-protected and sun-exposed skin. This approach is limited because NMSC is predominantly formed on body sites that are "usually" exposed to the sun when outdoors, as opposed to sites that are "occasionally" sun-exposed and as such they differ in their cumulative UV exposure. In an attempt to address this limitation, this example investigated the frequency of occurrence of a rarely reported 3895 bp mtDNA deletion in 104 age-matched human skin samples taken from usually, occasionally and rarely sun-exposed body sites. There was a significant increase in the deletion frequency with increasing UV exposure (p<0.0001) and of interest there was a significantly greater deletion frequency in body sites that are "usually" sun-exposed compared to those which are "occasionally" exposed in both the dermis (p=0.0018) and epidermis (p<0.0001). Investigation of the 3895 bp deletion in the same NMSC samples used in a previous study of the 4977 bp common deletion, showed a comparatively greater frequency of occurrence of the 3895 deletion (8/10 vs 4/10 respectively), although this difference was not statistically significant. In addition, the example furthers the link between the etiology of the 3895 bp deletion with the UVR component of sunlight by inducing the 3895 bp deletion in vitro with repetitive sub-lethal doses of a UVA+UVB light source. The frequency of the 3895 bp deletion in human skin provides a potential biomarker for cumulative UV exposure and provides an early detection tool for NMSC development as well as providing a method of monitoring long-term safety of clinical UV phototherapy regimes.

Patient Samples

Clinically normal perilesional skin from body sites that are "usually" exposed to the sun when outdoors (such as scalp, face, neck and ears) (epidermis n=21, dermis n=21, mean age±SEM=69.4±2.6) and body sites which are "occasionally" exposed to the sun (shoulders, back and chest) (epidermis n=21, dermis n=21, mean age±SEM=63.1±3.6) were taken with informed consent from 42 NMSC patients attending the skin cancer excision clinic at the Royal Victoria Infirmary, Newcastle, UK. There are no significant age differences between the usually and occasionally sun-exposed groups (p=0.158: two-tailed t test (Welch correction)). In addition, of the 42 patients, the percentage of females:males were almost the same (i.e., 52%:48% respectively) as well as the percentage of BCC and SCC, with 57% of the patients having a BCC. Normal skin samples from body sites that are rarely exposed to the sun (such as buttock and heel) were taken from previously obtained postmortem samples (epidermis n=10, dermis n=10, mean age=73y). Epidermis and dermis were separated using 0.25% dispase at 4° C. overnight (Durham et al, 2003) and DNA was extracted using a Qiagen, DNeasy tissue extraction kit. Epidermal tumours, BCC (n=5), SCC (n=5) were obtained from patients attending for cancer excision. None of the patients used for this study had a mtDNA defect.

UV Irradiation of HaCaT Cells

A spontaneously immortalized keratinocyte cell line (HaCaT) (Boukamp et al, 1988) was grown in Dulbecco's modified Eagle's medium containing, 10% fetal bovine serum 5 IU per mL penicillin and 5 g per mL streptomycin. The cells were grown to 70%-90% confluency in a 9 cm diameter tissue culture-treated Petri dishes, washed in PBS and then irradiated every alternate day with a sub-lethal dose (0.5 J per $cm^2$ which is equivalent to 1 SED) of UVR using a helarium 40 W lamp (Wolff B1.01, 290-400 nm, peak emission at 325 nm). At appropriate time points, total cellular DNA was extracted from the adherent cells using the Qiagen, DNeasy tissue extraction kit.

PCR Analysis

The PCR was carried out in a 25 µl reaction containing 200 ng genomic DNA, 600 nM of each primer, 250 µM dNTPs, 0.6 Upper reaction Amplitaq Gold DNA polymerase (Applied Biosystems), GeneAmp buffer (containing, 100 mM Tris-HCl, pH 8.3, 500 mM KCl, 15 mM MgCl and 0.01% (wt/vol) gelatin). The PCR primers used were L404 (5' CTT TTG GCG GTA TGC ACT TT 3') (404-423 nt) (SEQ ID NO: 145) and H4676 (5' GAT TAT GGA TGC GGT TGC TT 3') (4676-4657 nt) (SEQ ID NO: 146). Primers L404 and H4676 were designed to anneal outside the 3895 bp deletion. During DNA amplification the short (30 s) polymerase extension time did not permit amplification of wild-type PCR products, allowing only amplification of the smaller 375 bp product which represents the deleted mtDNA species. The PCR conditions were 94° C. for 10 min, 35 cycles of 94° C. for 30 s, 56° C. for 30 s, 72° C. for 30 s, and a final extension of 7 min at 72° C. Amplification products were visualised in a 1% agarose gel stained with ethidium bromide (0.25 µg per ml).

DNA Sequence Analysis

The 375 bp PCR product was gel excised and purified using QIAquick gel extraction kit (Qiagen, Germany) and cloned into a pCR®4-TOPO® vector using a TOPO®TA Cloning kit (Invitrogen, UK). To confirm the identity of the 375 bp PCR product, the DNA was sequenced using automated DNA sequencing (MWG Biotech, Ebersberg, Germany).

Radioactive PCR Analysis

To detect low levels of the deletion generated by UVR, the PCR was carried out as described above but with addition of 3 µCi of [$\alpha$-$^{32}$P]-dCTP (Amersham, Buckinghamshire, UK). The PCR products were then electrophoresed through a 6% non-denaturing polyacrylamide gel and exposed to a phosphorimage screen for approximately 24 hours. The radioactive PCR fragments were scanned and visualized by a Phosphorimager, using the ImageQuant software (Molecular Dynamics, UK).

Statistical Analysis

Statistical analyses were performed using StatCalc (Epi-info. CDC, Alberta, Ga.) employing $\chi^2$, Pearson's $\chi^2$, Fisher's exact and paired t tests.

Results and Discussion

Confirming the Identity of the 3895 bp Deletion

The mtDNA deletion spectrum of NMSC and sun-exposed skin from a previous study (Durham et al, 2003) was re-analyzed. It was found that many samples harboured a deletion approximately 4 kb in size. Following a search of the MITOMAP (Mitomap, 2004) database, the deletion was identified to be the 3895 bp species that was reported in the minor arc spanning nucleotides 547-4443. This deletion had previously been associated with Kearns Sayre Syndrome and Chronic Progressive External Opthalmoplegia (Moraes et al, 1995). To confirm the identity of the deletion, a deletion specific PCR assay was designed as explained in the methods section. The 375 bp product from this PCR was sequenced to confirm that it contained the deletion-junction sequence that is characteristic of the 3895 bp deletion, namely 5' CTAACC$^{536\ bp/4430\ bp}$ ccataccgaa$^{548\ bp/4442}$ AATGTT 3' (SEQ ID NO: 147). Characteristically, this sequence contained only one of the two 12 bp repeats that flank the 3895 bp deletion in wild-type mtDNA (lower case letters).

Figure 8:
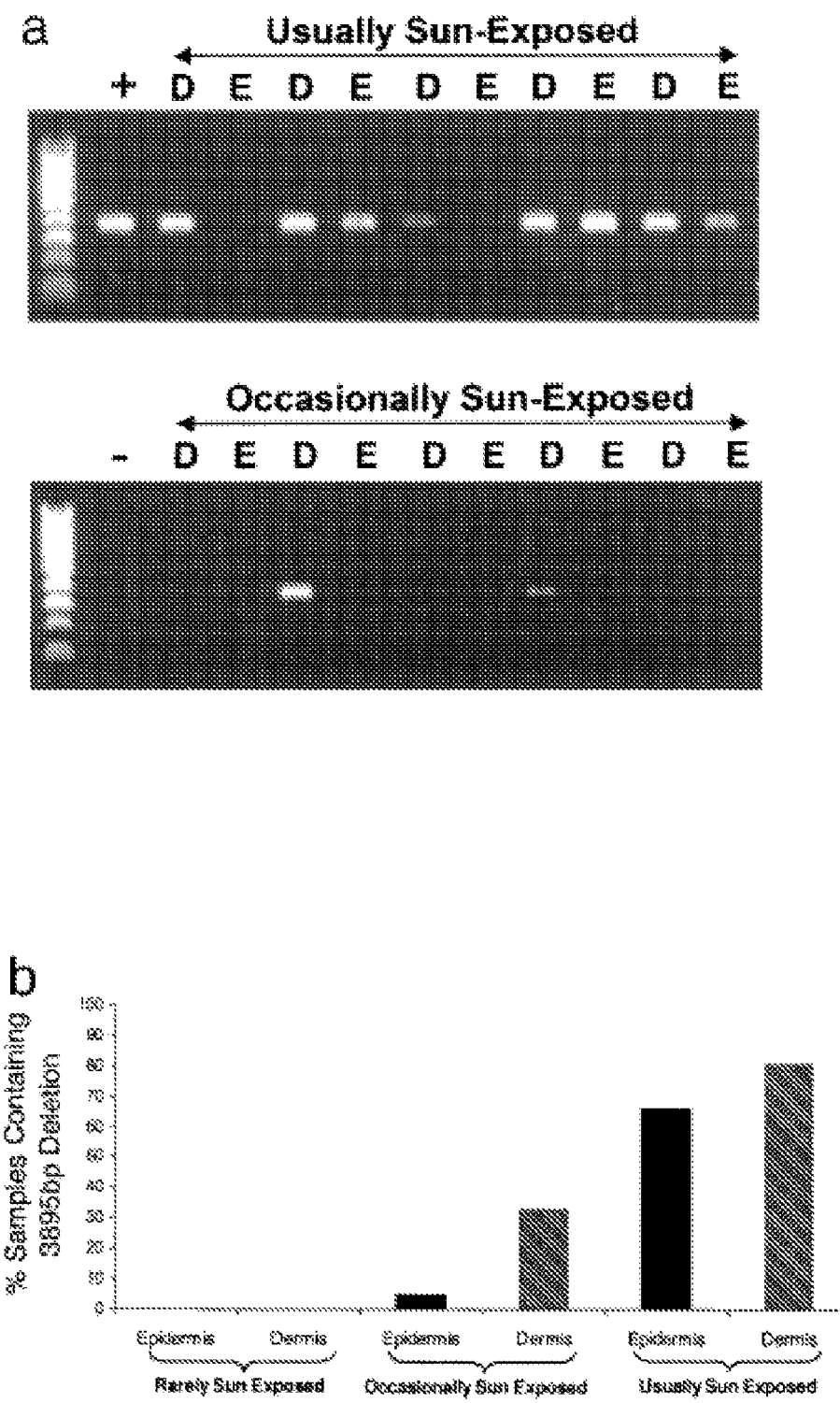

A Comparison of the Frequency of the 3895 Bp Deletion in Body Sites which are Usually Sun Exposed Versus Those which are Occasionally Exposed As the 3895 bp deletion was originally observed in NMSC samples taken from sun-exposed sites, the present inventors addressed the question of whether the frequency of the deletion is a marker of increasing cumulative sun-exposure. Using the deletion-specific PCR assay (see Materials and Methods), the frequency of occurrence in 104 age-matched, split human skin samples taken from usually, occasionally and rarely sun-exposed body sites was analyzed. There was a significant increase in the deletion frequency with increasing UV exposure in both the epidermis ($p<0.0001$, $\chi^2=31.36$, 2 df; Pearson's $\chi^2$ test) and dermis ($p<0.0001$, $\chi^2=28.68$, 2 df). FIG. 8 shows an increased frequency of occurrence of the 3895 bp deletion observed with increasing sun-exposure. FIG. 8a is a representative ethidium bromide stained, agarose gel showing a greater frequency of the 3895 bp deletion in body sites that are usually exposed (upper panel) to the sun when outdoors as opposed to those which are occasionally sun-exposed (lower panel) (D, dermis and E, epidermis). The positive control represents a sample with the 3895 bp deletion that has been confirmed by sequencing. Lane 1 in both panels prepresents molecular weight markers (Hyperladder IV-range 1000-100 bp, Bioline, London UK). The same amount of template DNA was added to each PCR reaction. FIG. 8b is the histogram showing the frequency of the 3895 bp deletion in 104 split skin samples taken from different sun-exposed body sites.

Importantly, there was a significantly greater deletion frequency in body sites that are "usually" sun-exposed compared to those that are "occasionally" exposed in both the dermis ($p=0.0018$, $\chi^2=9.72$, odds ratio 8.5; $\chi^2$ test) and epidermis ($p<0.0001$, $\chi^2=17.53$, odds ratio 40) (FIG. 8b). The deletion was not detected in the body sites that were "rarely" sun-exposed (FIG. 8b). As the mean ages, sex ratios and tumour type from which the perilesional skin was taken were very similar between the usually sun-exposed and occasionally exposed groups (see Materials and Methods), the findings are unlikely to be confounded by these factors. In addition, there was no statistical difference in the mean age values of those samples that harbored (i.e., mean=66.95±2.84) and did not harbor (mean=65.81±3.47) the 3895 bp deletion ($p=0.80$, t test (Welch correction)).

The 3895 bp mtDNA Deletion in NMSCs

Investigation of the 3895 bp deletion in the same NMSC samples, which were used in a previous study of the 4977 bp common deletion (Durham et al, 2003), showed a comparatively greater frequency of occurrence of the 3895 deletion (8/10 vs 4/10, respectively), although this difference was not statistically significant. As these tumours were excised from body sites that are usually exposed to the sun, it is interesting to speculate that the 3895 bp deletion may be a more sensitive marker of cumulative sun exposure than the common deletion.

Historically, it has been assumed that the minor arc region of the mitochondrial genome that contains the 3895 bp deletion does not harbour as many deletions as the major arc that contains the common deletion (Wei et al, 1996; Mitomap, 2004). As a result, the majority of previous studies have tended to focus on the spectrum of deletions in the major arc region. It could be due to this "research bias" that the 3895 bp deletion has a low reported incidence in the general literature. Alternatively, the 3895 bp deletion may naturally occur at currently undetectable levels in normal tissues, which is then enriched in the skin through exposure to UV.

Absence of the 3895 bp mtDNA Deletion in Blood

The 3895 bp deletion has only previously been reported in diseased muscle (Moraes et al, 1992). Apart from the present study in skin, the frequency of occurrence in other tissues is unknown. The present inventors investigated the deletion frequency in blood, by performing the deletion-specific PCR on 16 blood samples taken from patients of a similar age group to those of the skin samples. None of the blood samples were shown to harbour the deletion (data not shown).

Generation of the 3895 bp Deletion in Cultured HaCaT Cells by Repetitive UV Irradiation To assess the causal relationship between the cumulative amount of sun exposure and the frequency of occurrence of the 3895 bp deletion, it was necessary to investigate the effect of sunlight in vitro. As sunlight contains both UVA and UVB, an helarium lamp (Diffey, 2002) was used to provide an extensive series of repetitive sub-lethal UVR dose regimes in an attempt to generate the 3895 bp deletion in a human epidermal-derived (HaCaT) cell line. The optimal UVR repetitive dose strategy was one in which the deletion was generated without a significant degree of cell death. Using a radioactive PCR-based assay, we demonstrated that the first signs of induction of the 3895 bp deletion in adherent cells was observed following 17 alternate daily doses of 0.5 J per cm$^2$ (i.e., 1 SED) of UVR.

FIG. 9 shows that the helarium lamp (UVA/UVB) induces the 3895 bp deletion in HaCaT cells after 17 doses of 0.5 J per cm$^2$ UVR. HaCaT cells were irradiated with 0.5 J per cm$^2$ (i.e. 1 SED) of UVA/UVB every other day for a total of 19 doses. Total cellular DNA was extracted from adherent cells and 100 ng was subjected to PCR to amplify the 3895 bp deletion. The first signs of a UV-inducible increase of the 3895 bp deletion was observed following 17 repetitive doses of UVR. The positive control is DNA from a tumour sample harbouring the 3895 bp deletion, whereas the negative control does not contain DNA. Furthermore, as sub-lethal UVR doses were used, the level of the deletion was maintained in the cell line following two subsequent UV doses, a property that is important if the 3895 bp can be used as a putative cumulative biomarker of sun exposure in human skin. This is of interest given the very recent findings of Berneberg et al (2004) (published during manuscript revision), who have demonstrated in vivo that the UVA-induced common deletion may be present 16 months following cessation of irradiation.

The observations described above are important for several reasons. Firstly, the study has used a UVR source emitting both UVA and UVB thereby representing more closely a solar-simulated UVR source than those previous studies which generated the common deletion using UVA alone (Berneburg et al, 1999; Koch et al, 2001). Second, this is the first time a deletion other than the 4977 bp common deletion has been generated by repetitive doses of UVR. Furthermore, in contrast to the Berneburg study that utilised fibroblasts, the present experiments have been performed on a cell line derived from keratinocytes and it is this cell type that gives rise to NMSC.

Functional Significance

The regions that are deleted in the 3895 bp deletion are from the mtTF1 binding site in the D-loop to tRNA methionine. Deleted genes include 12s rRNA, 16s rRNA, ND1 and also the promoters for transcription of both the H and L strands. A certain threshold of wild-type:deleted mtDNA must be achieved before an impairment of mitochondrial respiratory function is observed (Sciacco et al, 1994). For protein-coding mtDNA genes, such as those removed by the 3895 bp deletion, the threshold value for mitochondrial respiratory chain dysfunction is around 65% and above (Hayashi et al, 1991; Chomyn et al, 1992). For example, previous work has shown that human skin samples harbouring <25% of the 4977 bp mtDNA common deletion, do not exhibit a deficiency of mitochondrial function as determined by dual histochemical staining of cytochrome oxidase and succinate dehydrogenase activities (Durham et al., 2002). Since there is no functional histochemical stain for the 3895 bp deletion, the deletion was quantified in the patient samples using Southern analysis. In the presence of appropriate controls, this analysis failed to detect the presence of the 3895 bp deletion thereby suggesting that the levels of the deletion are below 2%-5% (results not shown). Therefore based on the previous work with the common deletion, the levels of the 3895 bp deletion in the patient samples are unlikely to cause any functional effect across the entire dermis or epidermis although small focal effects cannot be ruled out.

Putative Mechanism

It has previously been suggested that the mechanism for the generation of the common deletion involves intragenomic recombination event via slipped-strand mispairing and may occur at the 13 bp repeat DNA sequences flanking the common deletion (Schon et al, 1989; Shoffner et al, 1989; Mita et al, 1990; Degoul et al, 1001). As the 3895 bp deletion is flanked by 12 bp repeats, its generation may occur by a similar mechanism. The mechanism for the generation of the common deletion proposes that the 13 bp repeats are susceptible to DNA bending thereby allowing a small region or "bubble" of single-stranded DNA to open (Schon et al, 1989). The present results suggest that UVR may be a contributing factor in the generation of the 3895 bp deletion. The mechanism for this may occur by directly or indirectly affecting the structurally labile sites in the 12 bp repeats through opening a "bubble" of single-stranded DNA that would enhance the recombination event.

Conclusions

In summary, the present example has shown that the frequency of a rarely reported 3895 bp-mtDNA is significantly different between body sites which are "usually" versus "occasionally" exposed to the sun when outdoors. Investigation of the 3895 bp deletion in the same NMSC samples used in a previous study of the 4977 bp common deletion showed a comparatively greater frequency of occurrence of the 3895 bp deletion. In addition, the link between the etiology of the 3895 bp deletion with the UVR component of sunlight has been established by inducing the 3895 bp deletion in vitro with repetitive sub-lethal doses of a UVA+UVB light source. The frequency of the 3895 bp deletion in human skin provides a potential biomarker for cumulative UV exposure in human skin and may in turn provide an early detection tool for NMSC development as well as providing a method of monitoring long-term safety of clinical UV phototherapy regimes.

Example 14

Real-Time PCR Analysis of the 3895 Mitochondrial DNA Deletion in NMSC and its Use as a Quantitative Marker for Sunlight Exposure in Human Skin Materials and Methods Human Skin Samples Tumour and matched perilesional skin samples were taken with informed consent from patients undergoing excision of a NMSC, namely Basal Cell Carcinoma (BCC) (n=5, age range 55-89 years, mean 78 years) or a Squamous Cell Carcinoma (SCC) (n=5, age range 70-87 years, mean 78 years) at the Out-Patients Clinic, Royal Victoria Infirmary, Newcastle, UK. For the sun-exposure studies, clinically normal perilesional skin was taken from body sites which are 'usually' exposed to the sun when outdoors (such as scalp, face, neck and ears) (epidermis n=30, dermis n=30, mean age±SEM=70.45±2.161) and body sites which are 'occasionally' exposed to the sun (shoulders, back and chest) (epidermis n=22, dermis n=22, mean age±SEM=63.77±3.501). There was no significant age differences between the usually and occasionally sun-exposed groups (p=0.1134): two-tailed t test (Welch correction). For all perilesional skin samples, epidermis and dermis were separated using 0.25% dispase at 4° C. overnight (Durham et al., 2003) and DNA was extracted using a Qiagen, DNeasy tissue extraction kit. None of the patients used for this study had a mtDNA defect.

PCR Analysis

The PCR was carried out in a 25 µl reaction containing 200 ng genomic DNA, 600 nM of each primer, 250 µM dNTPs, 0.6 u/reaction Amplitaq Gold DNA polymerase (Applied Biosystems), GeneAmp buffer (containing, 100 mM Tris-HCl, pH 8.3, 500 mM KCl, 15 mM MgCl and 0.01% (w/v) gelatin). The PCR primers L404 and H4676 (Table 9 and FIG. 10) were designed to anneal outside the 3895 bp deletion. During DNA amplification the short (30 s) polymerase extension time did not permit amplification of wild-type PCR products, allowing only amplification of the shorter and deleted mtDNA fragments. The PCR conditions were 94° C. for 10 minutes, 35 cycles of 94° C. for 30 s, 56° C. for 30 s, 72° C. for 30 s and a final extension of 7 minutes at 72° C. Amplification products were visualised in a 1% agarose gel stained with ethidium bromide (0.25 µg/ml).

This has been improved twice, first using Deep Vent (New England Biolabs) and then by a further improvement to sensitivity using Roche Faststart Taq. This has allowed one to move from measuring the deletion on sunexposed samples of aged patients, to being able to measure the deletion in young patients.

Real-Time PCR Analysis

A reliable TaqMan-PCR assay has been established for the quantification of the 3895 bp deletion. The quantitative TaqMan-PCR method provides real-time measurement of target input as PCR accumulation through a dual labelled probe. The probe anneals between forward and reverse primers and it is cleaved by the 5'-3' exonuclease activity of Taq polymerase during the PCR extension phase. Therefore, the 5'-terminal reporter dye FAM (6-carboxyfluorescein) or VIC and the 3'-terminal quencher dye TAMRA (6-carboxy-N,N,N',N'-tetramethylrhodamine) linked to the probe are separated, resulting in a fluorescence emission of the reporter dye. The probe is not able to serve as a primer itself because it is 3'-terminally blocked with a phosphate group. The method uses an internal standard probe (IS-Probe, Table 1 and FIG. 10) in the cytochrome b region of the genome (Koch et al., 2001), to estimate total copy number for mtDNA (i.e deleted and wild type). The level of 3895 bp deletion is determined by a probe (3895-probe, Table 9 and FIG. 10) which spans the break point of the deletion ensuring that it is only amplified if the deletion is present. Quantification of the level of deletion is determined by comparison of the ratio of the internal standard to the 3895 bp deletion.

Amplification reactions were performed as 25 ul triplicates in a 96-well microplate. Total mtDNA and deleted mtDNA reactions were amplified in separate tubes, each containing 100 ng of DNA, 1× TaqMan Universal Mastermix (ABI), 300 nM of each internal standard primer (ISF and ISR, Table 9 and FIG. 10) and 100 nM of the IS-Probe, or 300 nM of each 3895 bp deletion primer (3895F and 3895R, Table 9) and 100 nM of the 3895-probe (FIG. 10). PCR and fluorescence analysis was performed using a ABI Prism 7000 (Applied Biosystems, UK). Amplification conditions were as follows: 2 minutes at 50° C., 10 minutes at 95° C. followed by 40 cycles of 15 seconds at 95° C. and 1 minute at 60° C. The $R_n$ value is target reporter signal normalized to the passive reference, a dye included in the TaqMan reaction buffer. $\Delta R_n$ is defined as the difference between $R_n^+$ ($R_n$ of a reaction containing all the components including template) and $R_n^-$ ($R_n$ of a no template control). The cycle at which a statistically significant increase in $\Delta R_n$ is detected first is called the threshold cycle (Ct). Fluorescence signals are regarded as significant if the fluorescent intensity exceeds 10-fold the standard deviation of the background $R_n$ value to define a threshold.

The realtime PCR method is new and has not been published before. The method has an increased sensitivity and allows quantification, as compared to the semi quantitative standard PCR. This type of breakpoint specific detection is the same technique used for the prostate detection and is novel. We have shown it to be useful in the detection of mitochondrial rearrangements specifice for prostate cancer and sun exposure, but it can also be used for the detection of other rearrangements.

FIG. 10 shows the localisation of PCR primers and TaqMan probes and is a schematic representation of the mtDNA genome containing the 3895 bp deletion. Primers ISF/ISR and IS Probe, anneals to both wild-type and deleted mtDNA. Detection of the 3895 bp deletion was performed with primers 3895F/3895R and 3895 Probe. The specific 3895 probe only anneals to deleted mtDNA as it binds across the deletion junction. In addition, the occurrence of the 3895 bp deletion brings together the deletion specific primers (i.e. 3895F: 3895R and L404:H4676) close enough to allow generation of an amplicon under the given PCR conditions.

TOPO TA Cloning

Cloning of both control region and 3895 deletion were carried out using a TOPO TA Cloning kit (Invitrogen, UK) according to the manufacturers instructions. TOPO TA cloning takes advantage of the nontemplate-dependent terminal transferase activity of Taq polymerase that adds a single deoxyadenosine (A) to the 3' ends of PCR products. The linearised vector supplied with the kit has a single, overhanging 3' deoxythymidine (T) residue, allowing efficient ligation between PCR product and vector. The presence of an insert of the correct size was confirmed by EcoRI restriction fragment analysis in the vector pCR4-TOPO.

Results

Establishment of a Quantitative Real-Time PCR Assay for the 3895 bp Deletion

After determining that it was possible to reliably detect and quantify the percentage of copies of the mitochondrial genome harbouring the 3895 bp mtDNA deletion, the linearity of the two PCR reactions using either the internal standard probe (IS-probe) or the 3895 deletion probe (3895-probe) over a wide range of template concentrations was examined. In both cases, template DNA was generated by cloning the appropriate PCR product into a cloning vector (see methods). The concentration of each template was determined fluorometrically (GRI, UK), and real time PCR amplifications were performed using between 50 ng and 50 pg of template DNA for each probe (FIG. 11). The relationship between the CT value and the template concentration was linear for both the 3895 bp deletion (r=0.9952) and the internal standard (r=0.9941). In addition, the gradient for amplification of each template was the same. This confirms that each template is amplified to the same degree of efficiency. As a result, the CT values can therefore be used as a measure of template DNA and to quantify the relative amount of 3895 bp deletion to wild type mtDNA. The ability of these standard curves to accurately predict the ratio of deleted:wild type mtDNA was confirmed by using a range of the cloned deleted:wild type template mixtures (results not shown).

FIG. 11 shows the sensitivity of Realtime PCR to template copy number. Threshold cycle (i.e. CT, vertical axis) at decreasing concentrations of template DNA (dilution range from $\frac{1}{10}$-$\frac{1}{10000}$ of 1 ug/ul template) or the 3895 bp deletion (A) or wild type internal standard (B) are shown. There is a linear relationship between template concentration and the threshold cycle number (CT) for both amplifications. Each number represents the mean±SD for three independent observations.

Quantification of the 3895 bp Deletion in Tumours

The level of the 3895 bp deletion in both NMSC and histologically normal perilesional dermis and epidermis was determined by both real-time taqman PCR and a previously established standard PCR assay (FIG. 12). It was found that the levels of the 3895 bp deletion quantified by real-time PCR were generally in concordance with those estimated by the standard non-quantitative PCR analysis.

FIG. 12 shows realtime PCR quantification and standard PCR amplification of the 3895 deletion in tumours by showing ethidium bromide stained, agarose gels showing the incidence of the 3895 bp deletion in tumour (T) and histologically normal perilesional dermis (D) and epidermis (E) from both BCCs and SCCs. Below each lane is shown the level of the 3895 bp deletion illustrated as a percentage in each sample as quantified by realtime taqman PCR. Those samples marked with "ND" are determined to be zero as the CT of the realtime PCR was >36, which is the level observed in the no template control. Lane 1 in all panels=molecular weight markers (Hyperladder IV-range 1000-100 bp, Bioline Ltd, London UK). The same amount of template DNA was added to each PCR reaction.

The simple pattern of occurrence of the 3895 bp deletion in BCCs was generally similar to that observed in SCCs. In both BCCs and SCCs, the deletion was present in 3 of 5 patients (although not the same patients). In the perilesional skin the presence of the deletion was more frequent in the dermis (4 of 5 for BCCs, 3 of 5 SCCs) compared to the epidermis (2 of 5 BCCs, and 1 of 5 SCCs). However, although the absolute number of samples is small, there are differences between the BCC and the SCC results when one considers the actual level of the deletion rather than its simple pattern of occurrence. For example, for those samples where the deletion was present in both tumour and perilesional dermis, the level of the deletion was greatest in the dermis for SCC patients whereas the reverse tended to be true for the BCC patients. In addition, it was interesting to observe that BCC samples taken from 2 distinct areas of the face showed vastly different levels of the deletion (i.e. 7.14% versus 0.02%) which may reflect variation in the degree of cumulative sun-exposure. It was decided to investigate this aspect further by determining the level, as opposed to the pattern of occurrence, of the deletion in a relatively large subset of histologically normal perilesional samples taken from different sun-exposed body sites. Quantification of the 3895 bp Deletion in a Larger Subset of Histologically Normal Perilesional Skin Samples Taken from Different Sun-Exposed Body Sites Histologically normal perilesional skin, rather than tumour samples were chosen so as to avoid confounding factors other than the site of cumulative sun-exposure. Using quantitative real-time taqman PCR, the level of the 3895 bp deletion in 104 age-matched split human skin samples taken from various sun-exposed sites defined as usually exposed (n=60) and occasionally exposed (n=44) when outdoors was examined. FIG. 13 shows a typical example of an ethidium bromide stained agarose gel of the 3895 bp amplicon and the corresponding level of 3895 bp deletion as detected by realtime PCR in three pairs of usually and occasionally sun exposed samples. FIG. 13 shows the realtime PCR quantification and standard PCR amplification of the 3895 deletion in usually sun exposed and occasionally sun exposed representative ethidium bromide agarose gels showing typical examples of their corresponding level of 3895 deletion as detected by realtime PCR of three pairs of usually sun exposed and three pairs of occasionally sun exposed samples. The level of deletion is represented as a percentage. Lane 1 in both panels=molecular weight markers (Hyperladder IV-range 1000-100 bp, Bioline Ltd, London UK). The same amount of template DNA was added to each PCR reaction. The positive control in both panels is the tumour DNA from which the PCR product was cloned and sequenced to produce the template for realtime PCR. A comparison of the levels of the 3895 bp deletion detected by realtime PCR with those detected by standard PCR again showed a good correlation between the two techniques.

It was therefore decided to analyze all the samples using the quantitative Real-time PCR assay. The results from this analysis clearly showed an increased incidence of the 3895 bp deletion with increasing sun-exposure. FIG. 14 is a scatter plot showing the quantification of 3895 bp deletion in usually sun exposed and occasionally sun exposed skin. The levels of the 3895 bp deletion are expressed as a percentage in usually sun exposed and occasionally sun exposed dermis and epidermis, as determined by realtime taqman PCR. The mean level of deletion is indicated by a horizontal line for each set of samples.

In specific terms, the quantitative Real-time PCR analysis showed a significantly higher level of the deletion in the usually sun-exposed samples when compared to the occasionally sun-exposed samples (p=0.0009 for dermis, p=0.008 for epidermis; two-tailed t test). Interestingly, the dermal samples harboured a higher frequency of the deletion than the epidermis (p=0.0143 occasionally sun exposed, p=0.0007 usually sun-exposed). As the mean ages, sex ratios and tumour type from which the perilesional skin was taken were very similar between the usually sun-exposed and occasionally exposed groups (see methods), the findings are unlikely to be confounded by these factors.

TABLE 9

| Name | Dye | Position | Sequence |
|------|-----|----------|----------|
| ISF | | 16042-16066 | 5'-GAT TTG GGT ACC ACC CAA GTA TTG-3' SEQ ID NO: 148 |
| ISR | | 16125-16102 | 5'-AAT ATT CAT GGT GGC TGG CAG TA=3' SEQ ID NO: 149 |
| IS-Probe | Vic | 16069-16101 | 5'-CAC CCA TCA ACA ACC GCT ATG TAT TTC GTA CA-3'Tamra SEQ ID NO: 150 |
| 3895F | | 491-508 | 5'-CAA CCC TCG CCC ATC CTA-3' SEQ ID NO: 151 |
| 3895R | | 4516-4489 | 5'-CCT GCA AAG ATG GTA GAG TAG ATG AC-3' SEQ ID NO: 152 |
| 3895-probe | Fam | 527//4450 | 5'-TGC TAA CCC CAT ACC CCG AAA ATG TTG G-3'Tamra SEQ ID NO: 153 |
| L404 | | 404-423 | 5' CTT TTG GCG GTA TGC ACT TT 3') SEQ ID NO: 145 |
| H4676 | | 4676-4657 | 5' GAT TAT GGA TGC GGT TGC TT 3') SEQ ID NO: 146 |

Example 15

Confirmation of Biopsy Test

Previously unused needle core biopsy samples were recovered from the prostate sample archives: 62 benign, 49 malignant, 30 biopsies proximal to tumor yet containing no malignant cells. Overall, 141 total samples, as well as 7 additional samples, 6 for standard curve generation, and 1 negative control (reagent/reaction contamination) were analyzed. The complete assays were replicated three times, once each by three independent individuals.

The Artificial Neural Network (ANN) was blindly queried with benign samples adjacent to, or proximal to a tumour. In addition, some samples, determined to be distal to the tumor (mapped to this location after prostatectomy), were also included. The outcome was that 'normal' tissue in close proximity to tumor, had an elevated frequency of the 3.4 kb deletion, consistent with neighboring malignant tissue. However, distal benign, retained its benign signature (FIG. 15). This test will be able to confirm malignancy based on normal tissue obtained from a location near a tumour and is based on the 3.4 kb deletion research. It has been shown that molecular changes in mitochondrial DNA (i.e. the deletion) occur and preceed detectable morphological changes in the tissue. Hence a tissue region of a sample that may appear normal or benign to a pathologist under visual observation may have started to accumulate mutations on the path to malignancy. This capability is a great complement to the existing clinical practice of prostate biopsy and histological diagnosis by a pathologist. The use of the PSA test to screen for prostate cancer results in a large number of biopsy procedures with an estimated 70% failing to exhibit malignant cells. These biopsies are diagnosed benign and may be divided into two categories: true benigns, that is, no tumour is present in the prostate; and false benigns, where tumour is present in the prostate but the needle biopsy procedure failed to sample the malignancy. Through molecular testing of the benign tissue, one can either reassure those individuals in the true benign category that they are indeed benign such that they may be followed less closely with fewer or no follow-up biopsy procedures, or provide an earlier detection of a malignancy that is causing symptoms but is not yet detectable with the biopsy procedure, negating the need for an additional biopsy for diagnosis and providing an opportunity for the clinician to begin earlier and likely more effective treatment of the patient. This test will provide both reassurance and confirmation to the current biopsy analysis which is plagued by high numbers of false negative diagnosis.

Example 16

Prostate Tumour Mapping

An additional potential outcome of the research undertaken for the tumour behavior marker discovery is the ability to provide a three dimensional model of the location of the tumour within the prostate based upon the sextant needle biopsy specimens. The 3.4 kb deletion's capacity to reflect the presence of malignancy in neighbouring benign tissue will be critical to this mapping procedure. This map would provide the urologist and oncologist a virtual model of the prostate tumour and may assist in treatment decisions.

REFERENCES

Alonso, A. C Alves, M. P. Suarez-Mier, C Albarran, L Pereira, L Fernandez de Simon, P. Martin, O Garcia, L Gusmao, M Sancho, A Amorim 2005. J Clin Pathology 58: 83-86.
Anderson S, et al., Nature 290:457-464, 1981
Andrews R M, et al., *Nature Genetics* 23(2):147, 1999
Armstrong, B. K. & Kricker, A. (2001). The epidemiology of UV induced skin cancer. *J Photochem Photobiol B*, 63, 8-18.
Ammstrong, B. K. (2004). How sun exposure causes skin cancer: an epidemiological perspective. In *Prevention of Skin Cancer*, Hill, D., Elwood, J. M. & English, D. J. (eds), Vol. 3. pp. 89-116. Cancer Prevention—Cancer Causes. Kluwer Acedemic Publishers.
Barringer et al., *Gene*, 89:117 1990
Bassam B J, Caetano-Anolles P M, Gresshoff P M., Anal. Biochem. 196: 80-83, 1991
Berneburg, M., Gattermann, N., Stege, H., Grewe, M., Vogelsang, K., Ruzicka, T. & Krutmann, J. (1997). Chronically ultraviolet-exposed human skin shows a higher mutation frequency of mitochondrial DNA as compared to unexposed skin and the hematopoietic system. *Photochem Photobiol*, 66, 271-5.
Berneburg, M., Grether-Beck, S., Kurten, V., Ruzicka, T., Briviba, K., Sies, H. & Krutmann, J. (1999). Singlet oxygen mediates the UVA-induced generation of the photoaging-associated mitochondrial common deletion. *J Biol Chem*, 274, 15345-9.
Berneburg, M., Plettenberg, H., Medve-Konig, K., Pfahlberg, A., Gers-Barlag, H., Gefeller, O. & Krutmann, J. (2004). Induction of the photoaging-associated mitochondrial common deletion in vivo in normal human skin. *J Invest Dermatol*, 122, 1277-83.
Berthon P, Valeri A, Cohen-Akeninc A, Drelon E, Paiss T, Wohr G, Latil A et al., Am. J. Hum. Genet., 62: 1416-1424, 1998
Birch-Machin M A and Krishnan K. *Mitochondrion*, 1, p45 (2001).
Birch-Machin M A, et al., Methods in Toxicology, Volume 2, 51-69, 1993
Birch-Machin M A, Lindsey J. Lusher M and Krishnan K. *Mitochondrion*, 1 Suppl. 1, S30 (2001).
Birch-Machin M A, Online Conference Report (Sunburnt DNA), International Congress of Biochemistry and Molecular Biology, New Scientist, 2000(a)
Birch-Machin M A, Taylor R W, Cochran B, Ackrell B A C, Turnbull D M. *Ann Neurol* 48: 330-335, 2000(b)
Birch-Machin, M. A. (2000). Mitochondria and skin disease. *Clin Exp Dermatol*, 25, 141-6.
Birch-Machin, M. A., Tindall, M., Turner, R., Haldane, F. & Rees, J. L. (1998). Mitochondrial DNA deletions in human skin reflect photo-rather than chronologic aging. *J Invest Dermatol*, 110, 149-52.
Bogliolo, M, et al., Mutagenesis, 14: 77-82, 1999
Boukamp, P., Petrussevska, R. T., Breitkreutz, D., Hornung, J., Markham, A. & Fusenig, N. E. (1988). Normal keratinization in a spontaneously immortalized aneuploid human keratinocyte cell line. *J Cell Biol*, 106, 761-71.
Brierley E J, Johnson M A, Lightowlers R N, James O, Turnbull D M., Ann Neurol 43(2):217-223, 1998
Brockington, et al., *Nature Genet* 4:67-71, 1993
Brown, M. D., et al., Am J. Humn Genet, 60: 381-387, 1997
Brumley, R. L. Jr. and Smith, L. M., 1991, Rapid DNA sequencing by horizontal ultrathin gel electrophoresis, Nucleic Acids Res. 19:4121-4126 Nucleic Acids Res. 19: 4121-4126
Buttyan R, Sawczuk I S, Benson M C, Siegal J D, Olsson C A., Prostate 11:327-337, 1987
Byrne E., Curr Opin Reumatol 4(6):784-793, 1992
Cairns P, Okami K, Halachmi S, Halachmi N, Esteller M, Herman J G, Jen J et al., Cancer Res 57:4997-5000, 1997
Carew J. S. and Huang P. Molecular Cancer http://www.molecular-cancer.com (2002)
Chee, M. et al *Science* 274; 610-614, 1996
Chen J. Z. et al. *Cancer Research* (62): 6470-6474 (2002).
Chen J. Z. et al. *Carcinogenesis* (Vol 24) No. 9 1481-1487 (2003)
Chinnery P F and Turnbull D M., Lancet 354 (supplement 1): 17-21, 1999
Chinnery P F and Turnbull D M., *Lancet* 354 (supplement 1): 17-21, 2000
Chinnery P F, Howel N, Turnbull D M. *J. Med. Genet.;* 36: 425-436, 1999
Chollat-Traquet, C, Tobacco or health: a WHO programme., Eur J Cancer, 28(2-3): 311-315, 1992
Chomyn, A., Martinuzzi, A., Yoneda, M., Daga, A., Hurko, O., Johns, D., Lai, S. T., Nonaka, I., Angelini, C. & Attardi, G. (1992). MELAS mutation in mtDNA binding site for transcription termination factor causes defects in protein synthesis and in respiration but no change in levels of upstream and downstream mature transcripts. *Proc Natl Acad Sci USA*, 89, 4221-5.
Cohen D, Barton G. The cost to society of smoking cessation., Thorax. 53(2): S38-42, 1998
Corral-Debrinski et al., *Mutat Res,* 275: 169-180, 1991
Cortopassi G, Wang E., Biochim Biophys Acta 1271(1):171-176, 1995
Cortopassi G. A. and Arnheim, H. Detection of a specific mitochondiral DNA deletion in tissues of older humans, Nucleic Acids Tes. 18, 6927-6933 1990

Croteau D L, Stierum R H, Bohr V A, *Mutat Res* 434(3):137-148, 1999

Croteau, D. L. & Bohr, V. A. (1997). Repair of oxidative damage to nuclear and mitochondrial DNA in mammalian cells. *J Biol Chem*, 272, 25409-12. *Current Protocols in Molecular Biology*

Davis R M, Boyd G M, Schoenborn C A, "Common courtesy" and the elimination of passive smoking. Results of the 1987 National Health Interview Survey. JAMA 263(16): 2208-10, 1990

Degoul, F., Nelson, I., Amselem, S., Romero, N., Obermaier-Kusser, B., Ponsot, G., Marsac, C. & Lestienne, P. (1991). Different mechanisms inferred from sequences of human mitochondrial DNA deletions in ocular myopathies. *Nucleic Acids Res*, 19, 493-6.

Diffey, B. L. (2002). Sources and measurement of ultraviolet radiation. *Methods*, 28, 4-13.

Dong J T, Isaacs W B, Rinker-Schaeffer C W, Vukanovic J, Ichikawa T, Isaaca J T, Barrett J C., Science 268:884-886, 1995

Driezen P, Brown K S., Searchable database of questionnaire items from populations surveys of tobacco use in Canada: A summary report to the Ontario Tobacco Research Unit (Toronto, Ontario)

Durham, S. E., Krishnan, K. J., Betts, J. & Birch-Machin, M. A. (2003). Mitochondrial DNA damage in non-melanoma skin cancer. *Br J Cancer*, 88, 90-5.

Easton R D, Merriwether A D, Crews D E, and Ferrell R E., *Am. J. Hum. Genet.* 59:202-212, 1996

Fahn H, Wang L, Hseith R, Chang S, Kao S, Huang M, and Wei Y. *American Journal of Respiratory Critical Care Medicine*, 154:1141-1145, 1996

Fahn H J, Wang L S, Kao S H, Chang S C, Huang M H, Wei Y H., *Am. J. Respir. Cell. Mol. Biol.*, 19(6): 901-9, 1998

Finegold D., Mitochondrial Disease—Primary Care Physican's Guide. Psy-Ed. Corp D/B/A *Exceptional Parents Guide:* 12, 1997

Flanagan N, Birch-Machin M A, Rees J L., *Hum Mol Genet* 9 (17):2531-2537, 2000

Flanagan N, Ray A J, Todd C, Birch-Machin M A and Rees J L. J. Invest. Dermatol (2001) 117 (5)

Fliss M S, et al. *Science* 287: 2017-2019, 2000

Gattermann, N, Berneburg, M, Heinisch, J, Aul, C, Schneider, W., *Leukemia* 9(10): 1704-10, 1995

Green R, Reed J C., *Science* 281 (5381):1309-1312, 1998

Guatelli, et al., *Proc. Nat. Acad. Sci. U.S.A.* 87: 1874 1990

Gulavita, Sunil Dr. Northwestern Ontario Cancer Centre—Personal Communication

Habano S, Nakamura, Sugai T., *Oncogene* 17 (15):1931-1937, 1998

Harbottle et al., *The Journal of Investigative Dermatology:* 1518-1521, 2004.

Harding R M, et al., *Am. J. Hum. Genet.* 66, 1351-1361, 2000

Harman, D., *Proc Natl Acad Sci USA* 78(11): 7124-8, 1981

Hattori et al, Age-dependant increase in deleted mitochondrial DNA in the human heart: possible contributory factor to presbycardia, *AM. Heart J.*, 121, 1735-1742, 1991

Hayashi, J., Ohta, S., Kikuchi, A., Takemitsu, M., Goto, Y. & Nonaka, I. (1991). Introduction of disease-related mitochondrial DNA deletions into HeLa cells lacking mitochondrial DNA results in mitochondrial dysfunction. *Proc Natl Acad Sci*, 88, 10614-10618.

Hayward S W, Grossfeld G D, Tlsty T D, Cunha G R., *Int J Oncol* 13:35-47, 1998

Healy E, Birch-Machin M A, Rees J L. Chapter 11. *The Human Melanocortin* 1 *Receptor Gene. In the Melanocortin Receptors* (Cone R D (ed)). Humana Press Inc. New Jersey, USA, 1999

Healy E, Birch-Machin M A, Rees J I., *Lancet* 355, 1072-1073, 2000

Hearst N, Hulley S B. Using secondary data, *In Designing clinical research: an epidemiological approach*. Ed. Hulley, S. and Cummings, S., Baltimore: Williams & Wilkins, pages 53-62, 1988

Hopgood, R., et al, 1992, Strategies for automated sequencing of human mtDNA directly from PCR products, *Biotechniques* 13:82-92

Hsieh, R H and Wei, Y H, Age-dependent multiple deletions in human muscle mitochondrial DNA, in preparation 1992
Http://www.oml.gov/hgmis/project/budget.html)

Huang G M, Ng W L, Farkas J, He L, Liang H A, Gordon D, Hood R., *Genomics* 59(2):178-86, 1999

Huoponen, Kirsi, *Leber hereditary optic neuropathy: clinical and molecular genetic findings*, Neurogenetics (2001) 3: 119-125.

Ikebe et al., Increase of deleted mitochondrial DNA in the striatum in Parkinson's disease and senescence, *Biochem. Biophys. Res. Commun.* 170, 1044-1048, 1990

Innis et al PCR Protocols, *A Guide to Methods and Application*, Academic Press Inc. San Diego 1990

Kaiserman M J, *Chronic Dis Can* 18(1): 13-9, 1997

Kalra J, Chaudhary A K, Prasad K, *Int. J. Exp. Pathol.* 72(1): 1-7, 1991

Katayama et al., Deleted mitochondrial DNA in the skeletal muscle of aged individuals, *Biochem. Int.*, 25, 47-56 1991

Kleinle S, et al., *Human Genet.* 290: 457-465, 1997

Koch, H., Wittem, K. P. & Bergemann, J. (2001). In human keratinocytes the Common Deletion reflects donor variabilities rather than chronologic aging and can be induced by ultraviolet A irradiation. *J Invest Dermatol*, 117, 892-7.

Konishi N, Cho M, Yamamoto K, Hiasa Y. *Pathol. Int.* 47:735-747, 1997

Krishnan K and Birch-Machin M A. British Journal of Dermatology (2002), 146, 723

Kwoh et al. *Proc. Natl. Acad. Sci. U.S.A.*, 86: 1173 1989

Landegren et al. *Science,* 241: 1077 1988

Landis S H, Murray T, Bolden S, Wingo P A. *Cancer J. Clin.* 49:8-31

LeDoux S P, et al. *Mutat Res* 434(3):149-159, 1999

LeDoux, S. P., Patton, N. J., Avery, L. J. & Wilson, G. L. (1993). Repair of N-methylpurines in the mitochondrial DNA of xeroderma pigmentosum complementation group D cells. *Carcinogenesis*, 14, 913-7.

Lee H C, et al. *FEBS Letters* 354:79-83, 1994

Lee H C, et al. *Arch. Biochem. Biophys.* 362(2): 309-16, 1999

Lee H C, Lu C Y, Fahn H J, Wei Y Hu. *Federation of European Biochemical Societies,* 441:292-296, 1998

Leonard & Shapira 1997

Li Y, et al., In: *Oxygen Radicals and the Disease Process*, Amsterdam, The Netherlands: Harwood Academic Publishers, 237-277, 1997

Lindsey J, Lusher M, Krishnan K J and Birch-Machin M A., British Journal of Dermatology (2001), Linnane et al., 1990

Liu C S, Kao S H, Wei Y H. *Environ. Mol. Mutagen* 30(1): 47-55, 1997

Lopez, J. V. et al. (1994) Numt, a recent transfer and tandem amplification of mitochondrial DNA to the nuclear genome of the cat. J. Mol. Evol. 39, 174-190.

Lowes S, Krishnan K, Lindsey J, Lusher M and Brich-Machin M A. British Journal of Dermatology (2002, 146, 736

Luckey, J. A., et al, 1993, High speed DNA sequencing by capillary gel electrophoresis, *Methods Enzymol.* 218: 154-172

McCormack, Douglas. Website: http://cormactech.com/dna, 2001

Meibner C, von Wurmb N, Oehmichen M., *Int. J. Legal Med.* 110: 288-291, 1997

Michikawa Y, Mazzucchelli F, Bresolin N, Scarlato G, Attardi G., *Science* 286: 774-779, 1999

Miquel J, de Juan E, Sevila I. EXS 62:47-57, 1992

Mita, S., Rizzuto, R., Moraes, C. T., Shanske, S., Arnaudo, E., Fabrizi, G. M., Koga, Y., DiMauro, S. & Schon, E. A. (1990). Recombination via flanking direct repeats is a major cause of large-scale deletions of human mitochondrial DNA. *Nucleic Acids Res,* 18, 561-7.

Mitochondrial Research Society http://www.mitoresearch.org/diseases.html.

Mitomap. (2004). http://www.mitomap.org

MITOMAP: A Human Mitochondrial Genome Database. http://www.mitomap.org, 2005.

MITOMAP: A human mt genome database (www.gen.emory.edu/mitomap.html)

Moraes, C. T., Ricci, E., Petruzzella, V., Shanske, S., DiMauro, S., Schon, E. A. & Bonilla, E. (1992). Molecular analysis of the muscle pathology associated with mitochondrial DNA deletions. *Nat Genet,* 1, 359-67.

Moraes, C. T., Sciacco, M., Ricci, E., Tengan, C. H., Hao, H., Bonilla, E., Schon, E. A. & DiMauro, S. (1995). Phenotype-genotype correlations in skeletal muscle of patients with mtDNA deletions. *Muscle Nerve,* 3, S150-3.

Mullis and Faloona *Methods Enzymol* 155, 335 1987

Nachman M W, Brown W M, Stoneking M, Aquardo C F., *Genetics* 142:53-963, 1996

National Cancer Institute of Canada, Canadian cancer statistics 2000., National Cancer Institute of Canada., Toronto, Ont. 2000

Naviaux, R K., Mitochondrial Disease—Primary Care Physican's Guide. Psy-Ed. Corp DIB/A *Exceptional Parents Guide:* 3-10, 1997

Newton, C R and Graham, A., *Introduction to Biotechniques Series* 1997

Oefner P J, Underhill P A., *Current protocols in human genetics* 19, 7.10.1-12, 1998

Ozen M, et al, *Prostate* 36:264-271, 1998

Pang, C. Y., Lee, H. C., Yang, J. H. & Wei, Y. H. (1994). Human skin mitochondrial DNA deletions associated with light exposure. *Arch Biochem Biophys,* 312, 534-8.

Parsons T J, et al., *Nature Genet.* 15 (4):363-368, 1997

Pascucci, B., Versteegh, A., van Hoffen, A., van Zeeland, A. A., Mullenders, L. H. & Dogliotti, E. (1997). DNA repair of UV photoproducts and mutagenesis in human mitochondrial DNA. *J Mol Biol,* 273, 417-27.

Penta J S, Johnson F M, Wachsman J T, Copeland W C., *Mut. Res.* 488, 119-133, 2001

Polyak Y, et al., *Nature Genet.* 20 (3):291-293, 1998

Ray A J, Pickersgill L, Turner R, Nikaido O, Rees J L, Birch-Machin M A., *J. Invest. Dermatol* 115(4):674-679, 2000

Ray A J, Rees J L, Birch-Machin M A., *Brit. J. Dermatol.* 140:788, 1999

Ray A J, Rees J L, Birch-Machin M A., *J. Invest. Dermatol.* 110:692, 1998

Rees J L, Skin cancer. In: *The Genetic Basis of Human Cancer,* eds Vogelstein B, Kinzler K. New York: McGraw-Hill, pp 527-536, 1998

Rehman I, Quinn A J, Healy E, Rees J L. *Lancet* 344: 788-789, 1994

Rehman I, Takata M, Wu Y Y, Rees J L. *Oncogene* 12: 2483-2490, 1996

*SAS Enterprise Mining Users Guide*, SAS Inc., 2000

Sawyer, D. E. & Van Houten, B. (1999). Repair of DNA damage in mitochondria. *Mutat Res,* 434, 161-76.

Schon, E. A., Rizzuto, R., Moraes, C. T., Nakase, H., Zeviani, M. & DiMauro, S. (1989). A direct repeat is a hotspot for large-scale deletion of human mitochondrial DNA. *Science,* 244, 346-9.

Schurr T G, Ballinger S W, Gan Y, Hodge J A, Merriwether D A, Lawrence D N, Knowler W C, Weiss K M, and Wallace D C., *Am. J. Hum. Genet.* 46:613-623, 1990

Sciacco, M., Bonilla, E., Schon, E. A., DiMauro, S. & Moraes, C. T. (1994). Distribution of wild-type and common deletion forms of mtDNA in normal and respiration-deficient muscle fibers from patients with mitochondrial myopathy. *Hum Mol Genet,* 3, 13-9.

Seidman, M. D. et al., *Arch. Otolaryngol Head Neck Surg.,* 123: 1039-1045, 1997

Seo, Jinwook et al., *Interactively optimizing signal-to-noise ratios in expression profiling: project-specific algorithm selection and detection p-value weighting in Affymetrix microarrays,* Bioinformatics, Vol. 20, pp. 2534-2544, 2004a.

Seo, Jinwook, et al., *Interactive Color Mosaic and Dendrogram Displays for Signal/Noise Optimization in Microarray Data Analysis,* IEEE International Conference on Multimedia and Expo 2003.

Seo, Jinwook, Shneiderman, Ben, *A Rank-by-Feature Framework for Interactive Exploration of Multidimensional Data,* will appear in the journal, Information Visualization, 2005a. (pdf)

Seo, Jinwook, Shneiderman, Ben, *A Rank-by-Feature Framework for Unsupervised Multidimensional Data Exploration Using Low Dimensional Projections,* Proc. IEEE InfoVis 2004b, pp. 65-72.

Seo, Jinwook, Shneiderman, Ben, *Interactive Exploration of Multidimensional Microarray Data: Scatterplot Ordering, Gene Ontology Browser, and Profile Search,* HCIL-2003-25, CS-TR-4486, UMIACS-TR-2003-55.

Seo, Jinwook, Shneiderman, Ben, *Interactively Exploring Hierarchical Clustering Results,* IEEE Computer, Volume 35, Number 7, pp. 80-86, July 2002. [initial draft (pdf)]

Seo, Jinwook, Shneiderman, Ben, *Knowledge Integration Framework for Information Visualization,* will be published in LNCS by Springer-Verlag, Berlin Heidelberg New York, 2005b. (pdf)

Seo, Jinwook, Shneiderman, Ben, *Understanding Clusters in Multidimensional Spaces: Mading Meaning by Combining Insights from Coordinated Views of Domain Knowledge,* Technical Report, HCIL-2004-03, 2004c.

Severi, G. & English, D. J. (2004). Descriptive epidemiology of skin cancer. In *Prevention of Skin Cancer,* Hill, D., Elwood, J. M. & English, D. J. (eds), Vol. 3. pp. 73-88. Cancer Prevention—Cancer Causes. Kluwer Academic Publishers.

Shankey T V, Jin J K, Dougherty S, Flanigan R C, Graham S, Pyle J M., *Cytometry* 21:30-39, 1995

Shay J W, Werbin H., *Mutat. Res:* 186: 149, 1987

Sherrat E J, Thomas A W, Alcolado J C., *Clin. Sci.* 92:225-235, 1997

Shoffner J M, Brown M D, Torroni A, Lott M T, Cabell M F, Mirra S S, Beal M F, Yang C, Gearing M, Salvo R, Watts R L, Juncos J L, Hansen L A, Crain B J, Fayad M, Reckford C L, and Wallace D C., *Genomics* 17: 171-184, 1993

Shoffner, J. M., Lott, M. T., Voljavec, A. S., Soueidan, S. A., Costigan, D. A. & Wallace, D. C. (1989). Spontaneous Kearns-Sayre/chronic external opthalmoplegia plus syndrome associated with a mitochondrial DNA deletion: a slip-replication model and metabolic therapy. *Proc Natl Acad Sci USA,* 86, 7952-6.
Singh K. K. and Modica-Napolitano J. S. Expert reviews in molecular medicine. http://www.ermm.cbcu.ac.uk (2002)
Smith D G, Malhi R S, Eshleman J, Lorenz J G and Kaestle F A., *Am. J. Hum. Genet.* 110:271-284, 1999
Smith R, Birch-Machin M A, Rees J L. *J. Invest. Dermatol.* 111: 101-104, 1998
SpringNet—CE Connection: Screening, Diagnosis: Improving Primary Care Outcomes. Website: http://www.springnet.com/ce/j803a.htm
Stone A C and Stoneking M. Amer. J., *Phys. Anthro.* 92(4): 463-471, 1993
Tamura S, et al. *Eur. J. Cancer [A]* 35 (2):316-319, 1999
Tanaka, M. et al, 1996, Automated sequencing of mtDNA, *Methods Enzymol.* 264: 407-421
Taniike, M. et al., *BioChem BioPhys Res Comun,* 186: 47-53, 1992
Taylor R W, Birch-Machin M A, Bartlett K, Turnbull D M., *J Biol Chem,* 269, 3523-3528 1994
Tijssen, P. (ed) *Laboratory Techniques in Biochemistry and Molecular Biology,* Vol. 24: *Hybridization with Polynucleotide Probes,* Elsevier, N.Y., 1993
Tori et al., Ageing-associated deletions of human diaphragmatic mitochondrial DNA, *AM. J. Respir. Cell Mol. Biol.* in press 1992
Valnot, Isabelle, et al., A mitochondrial cytochrome b mutation but no mutations of nuclearly encoded subunits in ubiquinol cytochrome c reductase (complex III) deficiency, Human Genetics (1999) 104: 460-466.
Van De Graff, K M, Fox, S I. *Concepts of Human Anatomy and Physiology.,* Dubuque: W M. C. Brown Publishers, 1995
Van den Bosch B J C, et al., *Nucleic Acids Res.* 28: 89, 2000
von Wurmb, N, Oehmichen, M, Meissner, C., *Mutat Res.* 422:247-254, 1998
Wald and Wallace, D. C., Mitochondrial Diseases in man and Mouse. *Science,* 5(283): 1482-1497, 1999
Wald, N J, Hackshaw, A K, Cigarette Smoking: an epidemiological overview. *Br Med Bull.* 52(1): 3-11, 1996
Wallace D C. *Proc. Natl. Acad. Sci. USA* 91: 8739-8746, 1994
Wallace D C., *Annu Rev Biochem,* 61: 1175-1212, 1992
Wallace et al., Mitochondiral DNA MUtatio Assoicated with Leber's Hereditary Optic Neuropathy, *Science,* 1427-1429
Walsh P C, Partin A W. *Cancer* 80:1871-1874, 1997
Ward 1993
Ward R H, Frazier B L, Dew-Jager K, Paabo S., *Proc. Natl. Acad. Sci. USA* 88:8720-8724, 1991
Wei Y H. Proceedings of the Nat. Sci. Council of the Republic of China April 22(2):5567, 1998
Wei, Y. H., Pang, C. Y., You, B. J. & Lee, H. C. (1996). Tandem duplications and large-scale deletions of mitochondrial DNA are early molecular events of human aging process. *Ann NY Acad Sci,* 786, 82-101.
Weinstock M A: In: J J Stern R S, MacKie R M and Weinstock M A, Grob (eds) *Epidemiology,* Blackwell (UK). pp 121-128, 1998
Wesson, K. M. & Silverberg, N. B. (2003). Sun protection education in the United States: what we know and what needs to be taught. *Cutis,* 71, 71-4, 77.
Woodwell D A. National Ambulatory Medical Care Survey: 1997 Summary. Advance data from vital and health statistics; no. 305. Hyattsville, Md.: National Center for Health Statistics. 1999
Wu & Wallace *Genomics,* 4:560, 1989
Xu J, et al., *Nature Genet* 20: 175-179, 1998
Yamaguchi K T, et al., *Free Radical Res. Commun.* 16(3): 167-74, 1992
Yeh, J. J., et al., *Oncogene Journal,* 19: 2060-2066, 2000
Yen et al., Age-dependent 6 kb deletion in human liver mitochondirial DNA, *Biochem. Int.* 26, 457-468 1992
Yen et al., Ageing-associated 5 kb deletion in human liver mitochondrial DNA, *Biochem., Biophys., Res. Commun.,* 178, 124-131 1991
Zeviani M, et al. *Am. J. Hum. Genet.* 47:904-914, 1990
Zhang et al., Multiple mitochondiral DNA deletions in an elderly human individual, *FEBS Lett,* 297, 34-38 1992
Zhang, C., et al., *BioChem. BioPhys. Res. Comun.,* 195: 1104-1110, 1993
Zhao, Po et al., In vivo filtering of in vitro MyoD target data: An approach for identification of biologically relevant novel downstream targets of transcription factors, Comptes Rendus Biologies, Vol. 326, Issues 10-11, October-November 2003, pp 1049-1065.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08008008B2). An electronic copy of the "Sequence Listing" will also be available from the USPTO upon request and payment of the fee set forth in 37 CFR 1.19(b)(3).

What is claimed is:

1. A method of detecting a deletion spanning approximately nucleotides 10744 to 14124 of the human mtDNA genome, wherein said deletion is associated with prostate cancer, in a subject having mtDNA, comprising:
    (a) providing a biological sample from the subject;
    (b) extracting mtDNA from the biological sample; and
    (c) detecting the presence of the deletion in the mtDNA.

2. The method of claim 1, wherein the deletion is approximately 3379 bp.

3. The method of claim 1, wherein the deletion comprises substantially genes encoding NADH dehydrogenase subunit 4L, NADH dehydrogenase subunit 4, NADH dehydrogenase subunit 5, tRNA histidine, tRNAserine2, and tRNA leucine2.

4. The method of claim 1, wherein the step of detecting the presence of the deletion in the mtDNA comprises PCR analysis selected from the group consisting of deletion specific PCR analysis, radioactive PCR analysis, quantitative PCR and real-time PCR (RT-PCR) analysis.

5. The method of claim 4, wherein the PCR analysis is quantitative PCR or RT-PCR comprising amplification of a portion of the mtDNA using a recombinant, thermostable, Taq DNA polymerase.

6. The method of claim 4 wherein the PCR analysis comprises amplification of a portion of the mtDNA with a PCR forward primer having a sequence corresponding to SEQ ID NO: 139.

7. The method of claim 4, wherein a PCR primer that bridges the mtDNA junction formed by the deletion spanning approximately nucleotides 10744 to 14124 is used.

8. The method of claim 4, wherein the PCR analysis is quantitative PCR analysis comprising use of a primer that bridges the mtDNA junction formed by the deletion spanning approximately nucleotides 10744 to 14124.

9. The method of claim 1, wherein the method is used to detect prostate cancer, a predisposition to prostate cancer or the progression of prostate cancer.

10. The method of claim 1, wherein the step of detecting the presence of the deletion in the mtDNA comprises PCR analysis using a primer that bridges the mtDNA junction formed by the deletion spanning approximately nucleotides 10744 to 14124.

11. A method comprising detection of an mtDNA deletion spanning approximately nucleotides 10744 to 14124 of the human mtDNA genome as a biomarker for prostate cancer.

12. The method of claim 11, wherein the deletion is approximately 3379 bp.

13. The method of claim 11, wherein the deletion is detected in malignant tissue, adjacent benign tissue, distant benign tissue, precursor lesions, prostate massage fluid, urine, post-DRE urine, or blood, in a subject having prostate cancer or progressing toward prostate cancer or a subject without prostate cancer.

14. A method for confirming or refuting a prostate cancer biopsy test from a biopsy sample, comprising:
   (a) obtaining a normal tissue from a biopsy sample; and
   (b) detecting the absence or presence of a human mtDNA deletion at approximately nucleotides 10744 to 14124 of the human mtDNA genome in the normal tissue.

15. A method for three-dimensional prostate tumour mapping, comprising:
   (a) obtaining sextant needle biopsy samples;
   (b) extracting mtDNA from the biological samples; and
   (c) detecting the absence or presence of a deletion spanning approximately nucleotides 10744 to 14124 of the human mtDNA genome in each of the sextant samples.

16. A method for diagnosing prostate cancer, comprising hybridizing nucleic acids to an array, wherein the array comprises at least one nucleic acid member, and a solid substrate, wherein the at least one nucleic acid member is associated with a human mtDNA deletion at approximately nucleotides 10744 to 14124 of the human mtDNA genome, wherein the at least one nucleic acid member has a unique position on said array and is stably associated with the solid substrate.

17. A method for diagnosing prostate cancer comprising using a kit, wherein the kit comprises an array comprising at least one nucleic acid member and a solid substrate, wherein the at least one nucleic acid member is associated with a human mtDNA deletion at approximately nucleotides 10744 to 14124 of the human mtDNA genome, wherein the at least one nucleic acid member has a unique position on said array and is stably associated with the solid substrate and at least one member selected from the group consisting of: a disposable chip, means for holding the solid support, means for extraction of mitochondrial DNA, primers, reagents and instructions.

* * * * *